(12) United States Patent  
Colarusso et al.

(10) Patent No.: US 7,973,026 B2
(45) Date of Patent: Jul. 5, 2011

(54) THIENOPYRROLES AS ANTIVIRAL AGENTS

(75) Inventors: Stefania Colarusso, Rome (IT); Joerg Habermann, Pomezia (IT); Frank Narjes, Arccia (IT); Simona Ponzi, Rome (IT); Maria del Rosario Rico Ferreira, Pomezia (IT)

(73) Assignee: Istituto Di Ricerche Di Biologia Molecolare P. Angeletti SpA, Rome (IT)

( * ) Notice: Subject to any disclaimer, the term of this patent is extended or adjusted under 35 U.S.C. 154(b) by 663 days.

(21) Appl. No.: 11/920,064

(22) PCT Filed: May 3, 2006

(86) PCT No.: PCT/EP2006/004347
§ 371 (c)(1),
(2), (4) Date: Nov. 6, 2007

(87) PCT Pub. No.: WO2006/119975
PCT Pub. Date: Nov. 16, 2006

(65) Prior Publication Data
US 2009/0105227 A1    Apr. 23, 2009

(30) Foreign Application Priority Data

May 9, 2005   (GB) .................................. 0509326.5

(51) Int. Cl.
*A61K 31/33*   (2006.01)
*C07D 487/00*   (2006.01)
(52) U.S. Cl. ........................................ 514/183; 540/471
(58) Field of Classification Search .................. None
See application file for complete search history.

(56) References Cited

U.S. PATENT DOCUMENTS
7,659,263 B2 *  2/2010  Mizojiri et al. ............ 514/211.1

FOREIGN PATENT DOCUMENTS
EP         1 400 241 A1    3/2004
WO      WO 02/059321 A2    8/2002
WO     WO 2005/023819 A1   3/2005

OTHER PUBLICATIONS

Kim, Microbes and Infection, 2002, 4, 1219-25.*
"Cirrhosis-Prevention", http://www.mayoclinic.com/health/cirrhosis/DS00373/DSECTION=prevention, accessed Jul. 5, 2010.*
Licia Tomei et al., 81 Journal of General Virology 759-67 (2000).
V. Lohmann et al., 285 Science 110-13 (1999).
Volker Lohmann et al., 274(16) The Journal of Biological Chemistry 10807-15 (1999).
W. Clark Still et al., 43(14) Journal of Organic Chemistry 2923-25 (1978).

* cited by examiner

*Primary Examiner* — Noble Jarrell
(74) *Attorney, Agent, or Firm* — Julie M. Lake; Sheldon O. Heber

(57) ABSTRACT

The present invention relates to tetracyclic thienopyrrole compounds of formula (I), wherein Ar, A, D1, D2, W, X, Y and Z are defined herein, and pharmaceutically acceptable salts thereof, pharmaceutical compositions comprising them, and their use for the treatment or prevention of infection by hepatitis C virus.

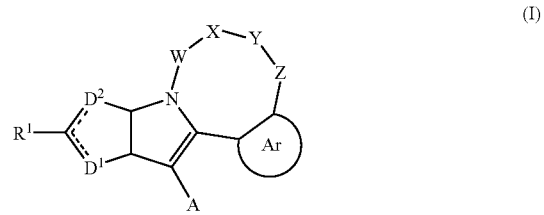

(I)

19 Claims, No Drawings

THIENOPYRROLES AS ANTIVIRAL AGENTS

CROSS-REFERENCE TO RELATED APPLLICATIONS

This application is a National Stage application of International application PCT/EP2006/004347, filed May 3, 2006. This application also claims priority to British Provisional application GB 0509326.5, filed May 9, 2005.

The present invention relates to tetracyclic thienopyrrole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit.

Published International patent application WO2005/023819 (Istituto di Ricerche di Biologia Molecolare) discloses thienopyrrole derivatives and their use in the treatment and prevention of hepatitis C infections. However, tetracyclic thienopyrrole derivatives are not disclosed.

Thus, the present invention provides the compound of the formula (I):

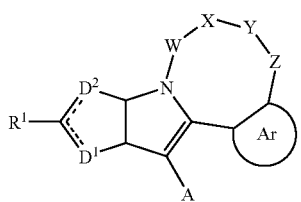

wherein

Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, aryl, heteroaryl, $CONR^cR^d$, $(CH_2)_{0-3}NR^cR^d$, $O(CH_2)_{1-3}NR^cR^d$, $O(CH_2)_{0-3}CONR^cR^d$, $O(CH_2)_{0-3}$aryl, $O(CH_2)_{0-3}$heteroaryl, $OCHR^eR^f$;

$R^c$ and $R^d$ are each independently selected from hydrogen, $C_{1-4}$ alkyl and $C(O)C_{1-4}$ alkyl;

or $R^c$, $R^d$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^e$ and $R^f$ are each independently selected from hydrogen and $C_{1-4}$alkyl;

or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is $C_{3-6}$alkyl or $C_{2-6}$alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$alkyl or $C_{1-4}$alkoxy;

one of $D^1$ and $D^2$ is S and the other is $C$—$(CH_2)_{0-3}R^2$;

$R^2$ is hydrogen, $C_{1-6}$alkyl, hydroxy, $(CH_2)_{0-3}C_{1-6}$alkoxy, $(CH_2)_{0-3}NR^aR^b$, $(CH_2)_{0-3}$aryl or $(CH_2)_{0-3}$aryloxy, optionally substituted by hydroxy or halogen;

$R^a$ and $R^b$ are each independently selected from hydrogen, $C_{1-6}$alkyl, $C_{2-6}$alkenyl, $C_{2-6}$alkynyl and $C_{3-8}$cycloalkyl;

the dotted line represents a bond between $C$—$(CH_2)_{0-3}R^2$ and $CR^1$;

$R^1$ is hydrogen, halogen, $C_{1-4}$alkyl, $C_{1-4}$alkoxy, CN, $CO_2H$, $CO_2C_{1-4}$alkyl, aryl, heteroaryl or $C(O)NR^3R^4$, where said $C_{1-4}$alkyl, $C_{1-4}$alkoxy, aryl and heteroaryl groups are optionally substituted by hydroxy or fluorine;

$R^3$ is hydrogen or $C_{1-4}$alkyl;

$R^4$ is hydrogen, $C_{1-4}$alkyl, $C_{2-4}$alkenyl, $(CH_2)_{0-3}(CR^jR^k)_{0-1}R^5$ or $SO_2R^6$;

$R^j$ and $R^k$ are independently selected from halogen, $C_{1-6}$alkyl or $C_{1-6}$alkoxy, or $R^j$ and $R^k$, together with the carbon atom to which they are joined, form a 4- to 7-membered carbocycle or heterocycle containing 1 or 2 heteroatoms selected from N, O and S;

$R^5$ is $NR^hR^i$, $OR^h$, $C(O)NR^qR^r$, aryl, heteroaryl or Het;

$R^h$ and $R^i$ are each independently selected from hydrogen and $C_{1-4}$alkyl;

$R^q$ and $R^r$ are each independently selected from hydrogen, $C_{1-6}$alkyl and aryl, optionally substituted by hydroxy, halogen, $C_{1-4}$alkyl, $C_{2-4}$alkenyl, $C_{2-4}$alkynyl, $(CH_2)_{0-3}CO_2H$, $(CH_2)_{0-3}CO_2(C_{1-6}$alkyl), $(CH=CH)CO_2H$ or $(CH=CH)CO_2(C_{1-6}$alkyl);

Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^6$ is $C_{1-4}$alkyl, $C_{2-4}$alkenyl or $(CH_2)_{0-3}R^7$;

$R^7$ is aryl, heteroaryl, $C_{1-4}$alkyl, $C_{3-8}$cycloalkyl, $CO_2R^8$, Het or $NR'''R''$, wherein Het is as hereinbefore defined, $R'''$ and $R''$ are each independently selected from hydrogen, $C_{1-4}$alkyl and $CO_2(CH_2)_{0-3}$aryl, and $R^8$ is hydrogen or $C_{1-6}$alkyl, and wherein $R^7$ is optionally substituted by halogen, $C_{1-4}$alkyl or $NR^oR^p$, wherein $R^o$ and $R^p$ are each independently selected from hydrogen and $C_{1-4}$alkyl;

and where $R^4$ is optionally substituted by hydroxy, fluorine, chlorine, $C_{1-4}$alkyl, oxo, $CO_2H$ or $CO_2C_{1-4}$alkyl;

or $R^3$, $R^4$ and the nitrogen atom to which they are attached form a heteroaliphatic ring of 4 to 7 ring atoms, where said ring is optionally substituted by halogen, hydroxy, oxo, $C_{1-4}$alkyl or $C_{1-4}$alkoxy;

W and Z are independently selected from a bond, C=O, O, S, S(O), $S(O)_2$, —$(CR^{10}R^{11})$—$(CR^{12}R^{13})_{0-1}$— and $NR^{10}$;

X and Y are independently selected from a bond, C=O, O, —$CR^{14}R^{15}$— and $NR^{14}$;

and none, one or two of W, X, Y and Z are a bond;

$R^{10}$, $R^{11}$, $R^{12}$, $R^{13}$, $R^{14}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, $(CH_2)_{0-3}$Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{0-3}NR^{16}R^{17}$, $S(O)_{0-2}(CH_2)_{0-3}R^{16}R^{17}$ and $C(O)(CH_2)_{0-3}OR^{16}$, where Het is optionally substituted by $C_{1-6}$alkyl;

$R^{16}$ and $R^{17}$ are independently selected from hydrogen, $C_{1-6}$alkyl, $(CH_2)_{0-4}NR^{18}R^{19}$ and $(CH_2)_{1-4}OR^{18}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

$R^{18}$ and $R^{19}$ are independently selected from hydrogen, C$_{1-6}$alkyl and (CH$_2$)$_{0-3}$phenyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

and pharmaceutically acceptable salts thereof.

In one embodiment, the present invention provides the compound of the formula (Io):

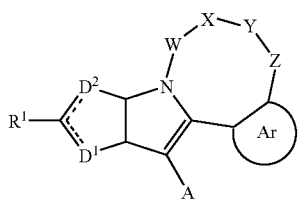

(Io)

wherein

Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, C$_{1-6}$alkyl, C$_{1-6}$alkoxy, aryl, heteroaryl, CONR$^c$R$^d$, (CH$_2$)$_{0-3}$ NR$^c$R$^d$, O(CH$_2$)$_{1-3}$NR$^c$R$^d$, O(CH$_2$)$_{0-3}$CONR$^c$R$^d$, O(CH$_2$)$_{0-3}$aryl, O(CH$_2$)$_{0-3}$heteroaryl, OCHR$^e$R$^f$;

R$^c$ and R$^d$ are each independently selected from hydrogen, C$_{1-4}$ alkyl and C(O)C$_{1-4}$ alkyl;

or R$^c$, R$^d$ and the nitrogen atom to which they are attached form a heteroaliphatic ring of 4 to 7 ring atoms, where said ring is optionally substituted by halogen, hydroxy, C$_{1-4}$alkyl or C$_{1-4}$alkoxy;

R$^e$ and R$^f$ are each independently selected from hydrogen and C$_{1-4}$alkoxy;

or R$^e$ and R$^f$ are linked by a heteroatom selected from N, O and S to form a heteroaliphatic ring of 4 to 7 ring atoms, where said ring is optionally substituted by halogen, hydroxy, C$_{1-4}$alkyl or C$_{1-4}$alkoxy;

and wherein said C$_{1-4}$alkyl, C$_{1-4}$alkoxy and aryl groups are optionally substituted by halogen or hydroxy;

$Q^2$ is halogen, hydroxy, C$_{1-4}$alkyl or C$_{1-4}$alkoxy, where said C$_{1-4}$alkyl and C$_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, C$_{1-4}$alkyl or C$_{1-4}$alkoxy;

A is C$_{3-6}$alkyl or C$_{2-6}$alkenyl, or A is a non-aromatic ring of 3 to 8 ring atoms where said ring may contain a double bond and/or may contain a O, S, SO, SO$_2$ or NH moiety, or A is a non-aromatic bicyclic moiety of 4 to 8 ring atoms, and A is optionally substituted by halogen, hydroxy, C$_{1-4}$alkyl or C$_{1-4}$alkoxy;

one of $D^1$ and $D^2$ is S and the other is C—(CH$_2$)$_{0-3}$R$^2$;

$R^2$ is hydrogen, C$_{1-6}$alkyl, hydroxy, (CH$_2$)$_{0-3}$C$_{1-6}$alkoxy, (CH$_2$)$_{0-3}$NR$^a$R$^b$, (CH$_2$)$_{0-3}$aryl or (CH$_2$)$_{0-3}$aryloxy, optionally substituted by hydroxy or halogen;

R$^a$ and R$^b$ are each independently selected from hydrogen, C$_{1-6}$alkyl, C$_{2-6}$alkenyl, C$_{2-6}$alkynyl and C$_{3-8}$cycloalkyl;

the dotted line represents a bond between C—(CH$_2$)$_{0-3}$R$^2$ and CR$^1$;

$R^1$ is hydrogen, halogen, C$_{1-4}$alkyl, C$_{1-4}$alkoxy, CN, CO$_2$H, CO$_2$C$_{1-4}$alkyl, aryl, heteroaryl or C(O)NR$^3$R$^4$, where said C$_{1-4}$alkyl, C$_{1-4}$alkoxy, aryl and heteroaryl groups are optionally substituted by hydroxy or fluorine;

$R^3$ is hydrogen or C$_{1-4}$alkyl;

$R^4$ is hydrogen, C$_{1-4}$alkyl, C$_{2-4}$alkenyl, (CH$_2$)$_{0-3}$(CR$^j$R$^k$)$_{0-1}$R$^5$ or SO$_2$R$^6$;

R$^j$ and R$^k$ are independently selected from halogen, C$_{1-6}$alkyl or C$_{1-6}$alkoxy, or R$^j$ and R$^k$, together with the carbon atom to which they are joined, form a 4- to 7-membered carbocycle or heterocycle containing 1 or 2 heteroatoms selected from N, O and S;

$R^5$ is NR$^h$R$^i$, OR$^h$, C(O)NR$^q$R$^r$, aryl, heteroaryl or Het;

R$^h$ and R$^i$ are each independently selected from hydrogen and C$_{1-4}$alkyl;

R$^q$ and R$^r$ are each independently selected from hydrogen, C$_{1-6}$alkyl and aryl, optionally substituted by hydroxy, halogen, C$_{1-4}$alkyl, C$_{2-4}$alkenyl, C$_{2-4}$alkynyl, (CH$_2$)$_{0-3}$CO$_2$H, (CH$_2$)$_{0-3}$CO$_2$(C$_{1-6}$alkyl), (CH=CH)CO$_2$H or (CH=CH)CO$_2$(C$_{1-6}$alkyl);

Het is a heteroaliphatic ring of 4 to 7 ring atoms, which ring may contain 1, 2 or 3 heteroatoms selected from N, O or S or a group S(O), S(O)$_2$, NH or NC$_{1-4}$alkyl;

$R^6$ is C$_{1-4}$alkyl, C$_{2-4}$alkenyl or (CH$_2$)$_{0-3}$R$^7$;

$R^7$ is aryl, heteroaryl, C$_{1-4}$alkyl, C$_{3-8}$cycloalkyl, CO$_2$R$^8$, Het or NR$^m$R$^n$, wherein Het is as hereinbefore defined, R$^m$ and R$^n$ are each independently selected from hydrogen, C$_{1-4}$alkyl and CO$_2$(CH$_2$)$_{0-3}$aryl, and $R^8$ is hydrogen or C$_{1-6}$alkyl, and wherein $R^7$ is optionally substituted by halogen, C$_{1-4}$alkyl or NR$^o$R$^p$, wherein R$^o$ and R$^p$ are each independently selected from hydrogen and C$_{1-4}$alkyl;

and where $R^4$ is optionally substituted by hydroxy, fluorine, chlorine, C$_{1-4}$alkyl, oxo, CO$_2$H or CO$_2$C$_{1-4}$alkyl;

or $R^3$, $R^4$ and the nitrogen atom to which they are attached form a heteroaliphatic ring of 4 to 7 ring atoms, where said ring is optionally substituted by hydroxy, oxo, C$_{1-4}$alkyl or C$_{1-4}$alkoxy;

W and Z are independently selected from a bond, C=O, O, S, S(O), S(O)$_2$, —(CR$^{10}$R$^{11}$)—(CR$^{12}$R$^{13}$)$_{0-1}$— and NR$^{10}$;

X and Y are independently selected from a bond, C=O, O, —CR$^{14}$R$^{15}$— and NR$^{14}$;

and none, one or two of W, X, Y and Z are a bond;

$R^{10}$, $R^{11}$, $R^{12}$, $R^{13}$, $R^{14}$ and $R^{15}$ are each independently selected from hydrogen, hydroxy, C$_{1-6}$alkyl, C$_{2-6}$alkenyl, C$_{1-6}$alkoxy, C(O)C$_{1-6}$alkyl, Het, (CH$_2$)$_{0-3}$NR$^{16}$R$^{17}$, C(O)(CH$_2$)$_{0-3}$NR$^{16}$R$^{17}$, NHC(O)(CH$_2$)$_{0-3}$NR$^{16}$R$^{17}$, O(CH$_2$)$_{0-3}$NR$^{16}$R$^{17}$, S(O)$_{0-2}$(CH$_2$)$_{0-3}$R$^{16}$R$^{17}$ and C(O)(CH$_2$)$_{0-3}$OR$^{16}$;

$R^{16}$ and $R^{17}$ are independently selected from hydrogen, C$_{1-6}$alkyl and (CH$_2$)$_{0-4}$NR$^{18}$R$^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

$R^{18}$ and $R^{19}$ are independently selected from hydrogen and C$_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

and pharmaceutically acceptable salts thereof.

In one embodiment of the present invention, Ar is a five- or six-membered aromatic ring optionally containing 1, 2 or 3 heteroatoms independently selected from N, O and S, and which ring is optionally substituted by groups Q$^1$ and Q$^2$ as hereinbefore defined.

Preferably, Ar is a five- or six-membered aromatic ring optionally containing 1 or 2 heteroatoms independently selected from N, O or S, such as phenyl, pyridyl, pyridazinyl, pyrimidinyl, pyrazinyl, furanyl, pyrazolyl, imidazolyl and thienyl, which ring is optionally substituted by groups Q$^1$ and Q$^2$ as hereinbefore defined. More preferably, Ar is phenyl, 2-pyridyl, 3-pyridyl, 4-pyridyl, 2-furanyl, 3-furanyl, 2-thienyl or 3-thienyl, particularly phenyl or 2-thienyl, optionally substituted by groups Q$^1$ and Q$^2$ as hereinbefore defined.

Preferably, Q$^1$ is halogen, hydroxy, C$_{1-4}$alkyl, C$_{1-4}$alkoxy, (CH$_2$)$_{0-3}$N(C$_{1-6}$alkyl)$_2$, O(CH$_2$)aryl or O(CH$_2$)heteroaryl. More preferably, Q$^1$ is fluorine, chlorine, methyl, methoxy, CH$_2$NMe$_2$, O(CH$_2$)phenyl or O(CH$_2$)pyridyl.

Preferably Q$^2$ is absent.

In a further embodiment, A is C$_{3-6}$alkyl, C$_{2-6}$alkenyl or C$_{3-8}$cycloalkyl, where A is optionally substituted by halogen, hydroxy, C$_{1-4}$alkyl or C$_{1-4}$alkoxy. Preferably, A is C$_{3-8}$cycloalkyl, more preferably cyclopentyl or cyclohexyl, more preferably cyclohexyl, optionally substituted by halogen, hydroxy, C$_{1-4}$alkyl or C$_{1-4}$alkoxy.

Preferably, A is unsubstituted or substituted by fluorine, chlorine, methyl or methoxy, particularly fluorine. More preferably, A is unsubstituted.

In a further embodiment, D$^1$ is S and D$^2$ is C—(CH$_2$)$_{0-3}$R$^2$, wherein R$^2$ is as hereinbefore defined. Preferably, R$^2$ is hydrogen, C$_{1-6}$alkyl, C$_{1-6}$alkoxy or (CH$_2$)$_{1-2}$N(C$_{1-6}$alkyl). More preferably, R$^2$ is hydrogen or C$_{1-4}$alkyl. Especially, R$^2$ is hydrogen or methyl. More especially, R$^2$ is hydrogen.

In a further embodiment, R$^1$ is CO$_2$H, heteroaryl or C(O)NR$^3$R$^4$ where said heteroaryl group is optionally substituted by hydroxy or fluorine, and wherein R$^3$ and R$^4$ are as hereinbefore defined. Preferably, R$^1$ is CO$_2$H, tetrazolyl, oxadiazolyl, C(O)NHSO$_2$R$^6$ or C(O)NH(CR$^j$R$^k$)$_{0-1}$R$^5$, where said oxadiazolyl group is optionally substituted by hydroxy, and wherein R$^5$ and R$^6$ are as hereinbefore defined. More preferably, R$^1$ is CO$_2$H or C(O)NHSO$_2$(CH$_2$)$_{0-3}$R$^7$ wherein R$^7$ is as hereinbefore defined. Most preferably, R$^1$ is CO$_2$H, C(O)NHSO$_2$CH$_2$CO$_2$R$^8$ or C(O)NHSO$_2$NR$^m$R$^n$. Especially, R$^1$ is CO$_2$H.

When R$^1$ is C(O)NR$^3$R$^4$ and R$^4$ is (CH$_2$)$_{0-3}$(CR$^j$R$^k$)$_{0-1}$R$^5$, preferably, R$^j$ and R$^k$, together with the carbon atom to which they are joined, form a 4-7 membered carbocycle, and R$^5$ is C(O)NR$^q$R$^r$ where R$^q$ and R$^r$ are as hereinbefore defined. More preferably, R$^j$ and R$^k$, together with the carbon atom to which they are joined, form a cyclobutyl, cyclopentyl or cyclohexyl ring, and R$^5$ is C(O)NHR$^r$ where R$^r$ is C$_{1-6}$alkyl or aryl, optionally substituted by hydroxy, halogen, C$_{1-4}$alkyl, (CH$_2$)$_{0-3}$CO$_2$H or (CH=CH)CO$_2$H. Most preferably, R$^j$ and R$^k$, together with the carbon atom to which they are joined, form a cyclopentyl or cyclohexyl ring, and R$^5$ is C(O)NHR$^r$ where R$^r$ is aryl, optionally substituted by hydroxy, halogen, (CH$_2$)$_{0-2}$CO$_2$H or (CH=CH)CO$_2$H. Especially, R$^1$ is:

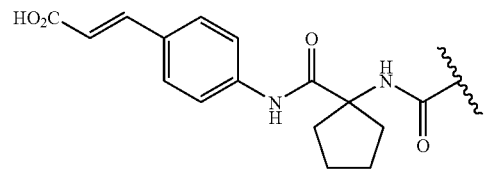

In a further embodiment, W is a bond, C=O, —(CR$^{10}$R$^{11}$)—(CR$^{12}$R$^{13}$)$_{0-1}$— or NR$^{10}$ where R$^{10}$, R$^{11}$, R$^{12}$ and R$^{13}$ are as hereinbefore defined. Preferably, W is a bond or —(CR$^{10}$R$^{11}$)—(CR$^{12}$R$^{13}$)$_{0-1}$—, such as —CH$_2$—, —CH$_2$CH$_2$—, —CH(CH$_3$)—, —CH(CH$_3$)—CH(CH$_3$)—, —C(CH$_3$)$_2$— or —C(CH$_3$)$_2$—C(CH$_3$)$_2$—. More preferably, W is a bond, —CH$_2$— or —CH$_2$CH$_2$—. Most preferably, W is a bond or —CH$_2$—.

In a further embodiment, Z is a bond, C=O, O, —(CR$^{10}$R$^{11}$)—(CR$^{12}$R$^{13}$)$_{0-1}$— or NR$^{10}$ where R$^{10}$, R$^{11}$, R$^{12}$ and R$^{13}$ are as hereinbefore defined. Preferably, Z is a bond, O, —(CR$^{10}$R$^{11}$)—(CR$^{12}$R$^{13}$)$_{0-1}$— or NR$^{10}$. More preferably, Z is a bond, O, —CH$_2$—, —CH$_2$CH$_2$— or NH. Most preferably, Z is a bond, O or —CH$_2$—.

In a further embodiment, X is C=O, —CR$^{14}$R$^{15}$— or NR$^{14}$ where R$^{14}$ and R$^{15}$ are as hereinbefore defined. Preferably, X is C=O, —CH$_2$—, —CH(C$_{1-6}$alkyl)—, —CHNHR$^{16}$, —CHN(C$_{1-4}$alkyl)$_2$ or CH—O—(CH$_2$)$_2$—NR$^{16}$R$^{17}$ where R$^{16}$ and R$^{17}$ are as hereinbefore defined. More preferably, X is C=O, —CH$_2$—, CHN(C$_2$H$_5$)$_2$, CH—O

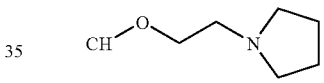

or CHNH—CH$_2$—CH$_2$—NR$^{18}$R$^{19}$ where R$^{18}$ and R$^{19}$ are as hereinbefore defined. Preferably, R$^{18}$ and R$^{19}$ are both CH$_3$, or R$^{18}$, R$^{19}$ and the nitrogen atom to which they are attached form an azetidinyl, pyrrolidinyl or piperidinyl ring.

In a further embodiment, Y is C=O, O, —CR$^{14}$R$^{15}$— or NR$^{14}$ where R$^{14}$ and R$^{15}$ are as hereinbefore defined. Preferably, Y is O, —CR$^{14}$R$^{15}$— or NR$^{14}$. More preferably, Y is O, —CH$_2$—, —CH(OH)—, —CH(O—(CH$_2$)$_2$NR$^{16}$R$^{17}$)—, NH, N(C$_{1-6}$alkyl), NCH$_2$CH$_2$N(C$_{1-6}$alkyl)$_2$, NC(O)(CH$_2$)$_{1-2}$N(C$_{1-6}$alkyl)$_2$ or N(CH$_2$)$_{1-3}$Het, optionally substituted by halogen, hydroxy, C$_{1-4}$alkyl, benzyloxy or N(C$_{1-4}$alkyl)$_2$. Examples of suitable Y groups include: O, —CH$_2$—, —CH(OH)—, NH, N—CH$_3$,

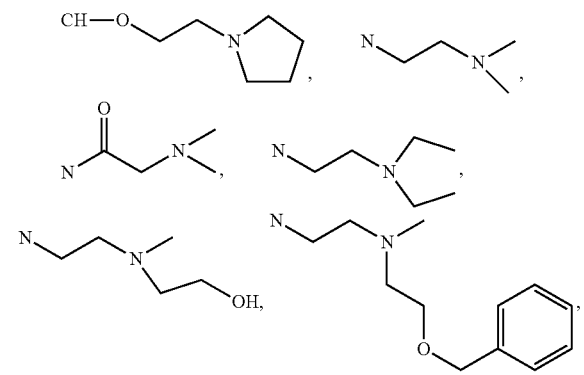

-continued

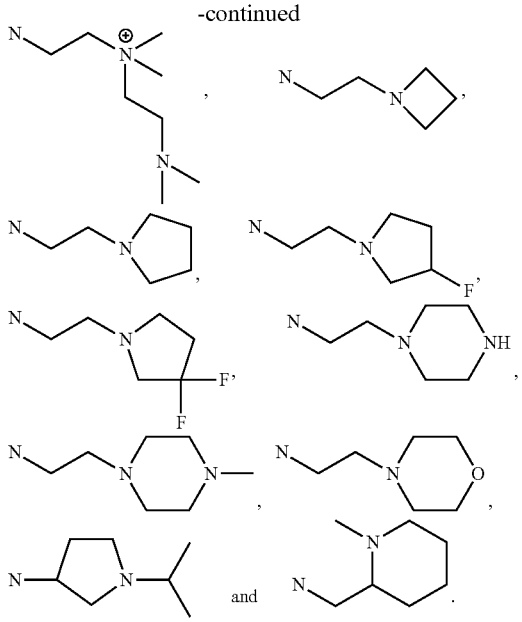

One favoured group of compounds of the present invention is of formula (Ia) and pharmaceutically acceptable salts thereof:

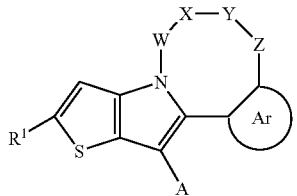
(Ia)

wherein W, X, Y, Z, $R^1$, A and Ar are as defined in relation to formula (I).

In one embodiment, the compounds of formula (Ia) have the formula (Iaa):

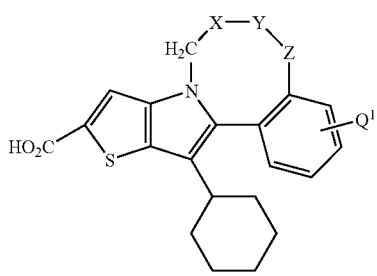
(Iaa)

wherein X, Y, Z and $Q^1$ are as defined in relation to formula (I).

Preferably, X is C=O or —$CR^{14}R^{15}$— where $R^{14}$ and $R^{15}$ are as defined in relation to formula (I). More preferably, X is C=O, —$CH_2$—, $CHOCH_2CH_2NR^{16}R^{17}$ or $CHNHR^{16}$ where $R^{16}$ and $R^{17}$ are as defined in relation to formula (I). Most preferably, X is C=O, —$CH_2$—, $CHOCH_2CH_2NR^{18}R^{19}$ or $CHNHCH_2CH_2NR^{18}R^{19}$ where $R^{18}$ and $R^{19}$ are as hereinbefore defined. Preferably, $R^{18}$ and $R^{19}$ are both $CH_3$, or $R^{18}$, $R^{19}$ and the nitrogen atom to which they are attached form an azetidinyl, pyrrolidinyl or piperidinyl ring, especially a pyrrolidinyl ring.

Preferably, Y is —$CR^{14}R^{15}$— or $NR^{14}$ where $R^{14}$ and $R^{15}$ are as defined in relation to formula (I). More preferably, Y is —$CH_2$—, —CH(OH)—, —$CH(O(CH_2)_2NR^{16}R^{17})$, NH, $N(C_{1-6}alkyl)$, $N(CH_2)_{1-2}N(C_{1-6}alkyl)_2$, $NC(O)(CH_2)_{1-2}N(C_{1-6}alkyl)_2$ or $N(CH_2)_{1-3}Het$, optionally substituted by halogen, hydroxy, $C_{1-4}alkyl$, benzyloxy or $N(C_{1-4}alkyl)_2$. Examples of suitable Y groups include: —$CH_2$—, —CH(OH)—, NH, N—$CH_3$,

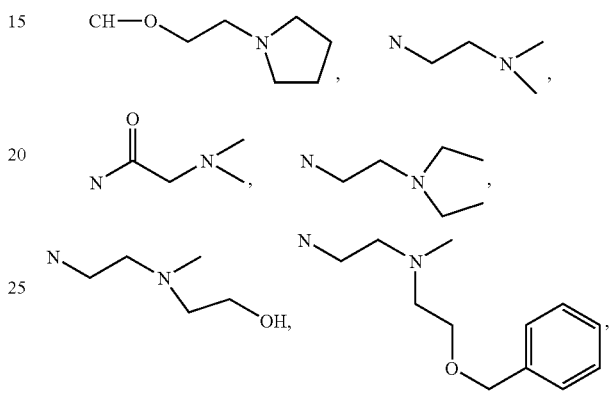

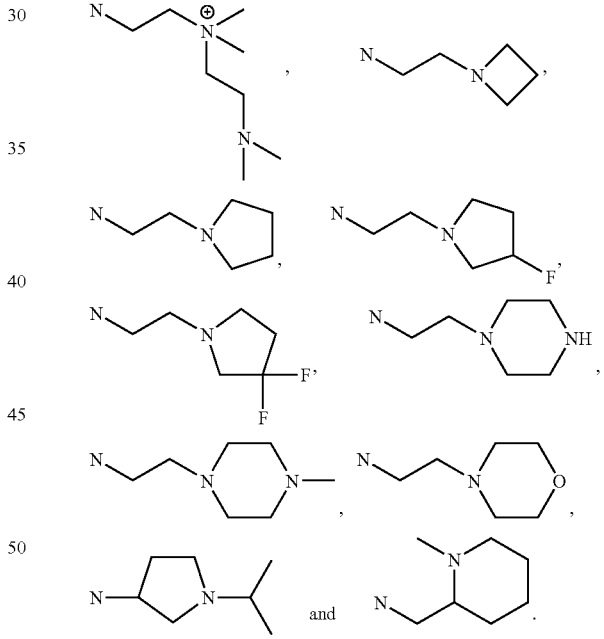

Preferably, Z is a bond, O or —$CR^{10}R^{11}$—. Most preferably, Z is a bond, O or —$CH_2$—.

Preferably, $Q^1$ is $C_{1-6}alkoxy$, $O(CH_2)_{0-3}aryl$, $O(CH_2)_{0-3}heteroaryl$, halogen or absent. More preferably, $Q^1$ is $C_{1-4}alkoxy$, $O(CH_2)_2aryl$, $O(CH_2)_2heteroaryl$, halogen or absent. Most preferably, $Q^1$ is methoxy, benzyloxy, O—$CH_2$-pyridyl, fluorine, chlorine or absent.

Another favoured group of compounds of the present invention is of formula (Ib) and pharmaceutically acceptable salts thereof:

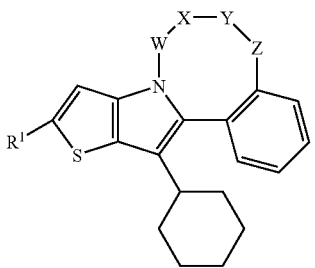

(Ib)

wherein W, X, Y, Z and $R^1$ are as defined in relation to formula (I).

Preferably, W is —$(CR^{10}R^{11})$—$(CR^{12}R^{13})_{0-1}$— where $R^{10}$, $R^{11}$, $R^{12}$ and $R^{13}$ are as defined in relation to formula (I). More preferably, W is —$(CR^{10}R^{11})$— where $R^{10}$ and $R^{11}$ are as defined in relation to formula (I). Most preferably, W is —$CH_2$—.

Preferably, X is —$CR^{14}R^{15}$— where $R^{14}$ and $R^{15}$ are as defined in relation to formula (I). More preferably X is —$CH_2$—.

Preferably, Y is —$CR^{14}R^{15}$— or $NR^{14}$ where $R^{14}$ and $R^{15}$ are as defined in relation to formula (I). More preferably, Y is $NR^{14}$ where $R^{14}$ is as defined in relation to formula (I). Most preferably, Y is NH or $N(C_{1-6}alkyl)$. Especially, Y is $N(CH_3)$.

Preferably Z is —$(CR^{10}R^{11})$—$(CR^{12}R^{13})_{0-1}$— where $R^{10}$, $R^{11}$, $R^{12}$ and $R^{13}$ are as defined in relation to formula (I). More preferably, Z is —$(CR^{10}R^{11})$— where $R^{10}$ and $R^{11}$ are as defined in relation to formula (I). Most preferably, Z is —$CH_2$—.

Preferably, $R^1$ is $C(O)NR^3R^4$ where $R^3$ and $R^4$ are as defined in relation to formula (I). More preferably, $R^1$ is $C(O)NHR^4$ where $R^4$ is $(CH_2)_{0-3}(CR^jR^k)_{0-1}R^5$ where $R^j$, $R^k$ and $R^5$ are as defined in relation to formula (I). Most preferably, $R^1$ is
$C(O)NH(CR^jR^k)C(O)NR^qR^r$ where $R^j$, $R^k$, $R^q$ and $R^r$ are as defined in relation to formula (I). Especially, $R^1$ is:

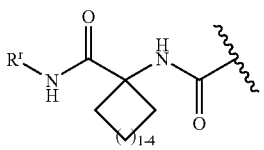

where $R^r$ is as defined in relation to formula (I). Examples of $R^1$ include:

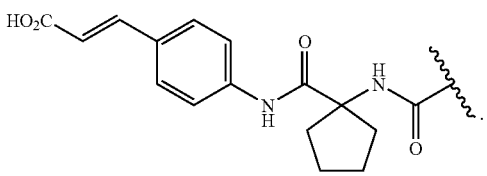

In another embodiment, the compounds of formula (Ia) have the formula (Iab):

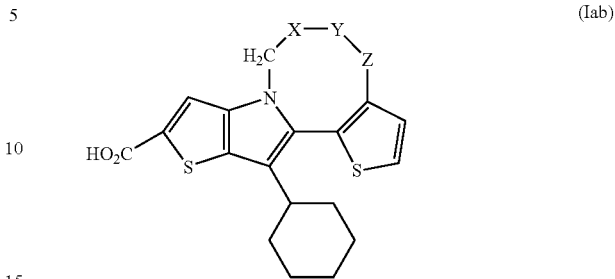

(Iab)

wherein X, Y and Z are as defined in relation to formula (I).

Preferably, X is —$CH_2$—.

Preferably, Y is $NR^{14}$, where $R^{14}$ is as defined in relation to formula (I). More preferably, Y is $N(CH_2)_{1-3}NR^{16}R^{17}$ where $R^{16}$ and $R^{17}$ are as defined in relation to formula (i). Most preferably, Y is $N(CH_2)_2N(C_{1-4}alkyl)_2$, such as $N(CH_2)_2N(CH_3)_2$ and $N(CH_2)_2N(C_2H_5)_2$.

Preferably, Z is —$CH_2$—.

In a further embodiment of the present invention, there is provided the compounds of formula (Ic):

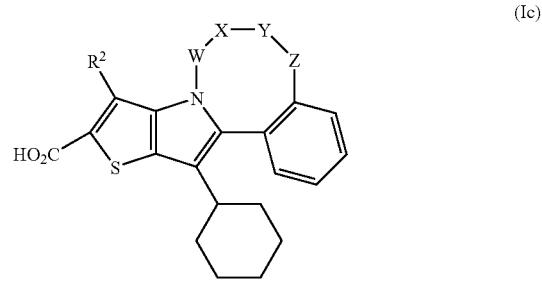

(Ic)

and pharmaceutically acceptable salts thereof,
wherein W, X, Y and Z are defined in relation to formula (I) and $R^2$ is $C_{1-4}$alkyl.

Preferably, W is a bond or —$CH_2$—.

Preferably, X is a bond, —$CH_2$— or —$CHR^{14}$—, where $R^{14}$ is as defined in relation to formula (I). More preferably, X is a bond or —$CH(NR^{16}R^{17})$—, where $R^{16}$ and $R^{17}$ are as defined in relation to formula (I). Most preferably, X is a bond or —$CH(N[C_{1-4}alkyl]_2)$—, such as —$CH(N[CH_3]_2)$—.

Preferably, Y is O or —$CH_2$—.

Preferably, Z is a bond or O.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the term "alkenyl" as a group or part of a group means that the group is straight or branched. Examples of suitable alkenyl groups include vinyl and allyl.

When used herein, the term "halogen" means fluorine, chlorine, bromine and iodine. Preferred halogens are fluorine and chlorine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolinyl and isoquinolinyl.

Where a compound or group is described as "optionally substituted" one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Table hereinbelow and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (a), compounds of formula (I) where Z is $CH_2$, X is C=O and Y is $NR^{14}$ may be prepared by the reaction of a compound of formula (II) with a compound of formula (III) followed by internal ring closure:

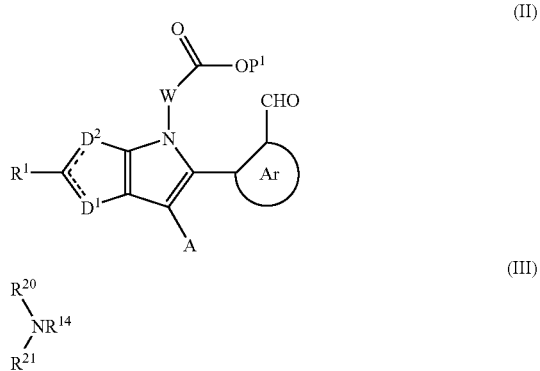

where $D^1$, $D^2$, W, A, Ar, $R^1$ and $R^{14}$ are as defined in relation to formula (I), $R^{20}$ and $R^{21}$ are independently selected from hydrogen, methyl and ethyl, and $P^1$ is a suitable protecting group. The reaction may conveniently be carried out in the presence of a mild reducing agent, such as sodium borohydride or sodium cyanoborohydride, in a suitable solvent, such as tetrahydrofuran or methanol.

According to a general process (b), compounds of formula (I) where Z is O, W and Y are $CH_2$ and X is C=O may be prepared by the internal ring closure of a compound of formula (IV) followed by oxidation:

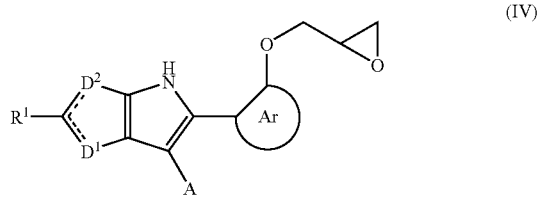

where $D^1$, $D^2$, A, Ar, $R^1$ and $R^{14}$ are as defined in relation to formula (I). The reaction may conveniently be carried out in the presence of a base, such as sodium hydride, in a suitable solvent, such as DMF.

According to a general process (c), compounds of formula (I) where X is C=O and Y is $NR^{14}$ can be prepared by internal ring closure of a compound of formula (V):

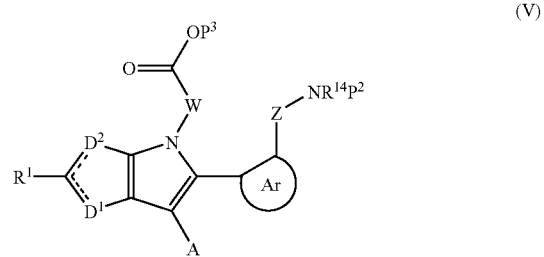

where W, Z, $D^1$, $D^2$, A, Ar, $R^1$ and $R^{14}$ are as defined in relation to formula (I), and $P^2$ and $P^3$ are suitable protecting groups. Depending on the exact nature of $P^2$ and $P^3$, deprotection can be achieved under basic or acidic conditions and the resulting acid is then coupled to the amine using a peptide coupling reagent, such as HATU or EDCI. Alternatively, if $P^3$ is an alkyl group, especially methyl, and $P^2$ is absent, cyclisation may be achieved using a suitable base, such as sodium methoxide, in a suitable solvent, such as methanol.

According to a general process (d), compounds of formula (I) where Z is $CHR^{10}$, Y is $CHR^{14}$, X is $CH_2$ and W is $-(CH_2)_{(n-1)}-$ can be prepared by ring-closure metathesis of a compound of formula (VI) followed by elaboration of the newly formed double bond:

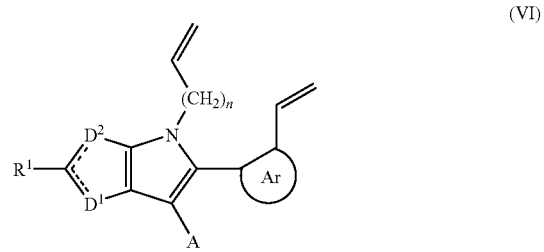

where n is 1 to 3 and $D^1$, $D^2$, A, Ar, $R^1$, $R^{10}$ and $R^{14}$ are defined as in formula (I). The reaction may be conveniently carried out in the presence of a ring-closure metathesis catalyst (e.g. a ruthenium catalyst).

Compounds of formulae (II), (III), (IV), (V) and (VI) are either known in the art or may be prepared by conventional methodology well known to one of ordinary skill in the art using, for instance, procedures described in the accompanying Schemes and Examples, or by alternative procedures which will be readily apparent.

Further details of suitable procedures will be found in the accompanying Schemes and Examples. For instance, compounds of formula (I) can be converted into other compounds of formula (I) using synthetic methodology well known in the art.

Thus, for instance, the compound of formula (I) where $R^1$ is $CO_2CH_3$ may be converted into the compound of formula (I) where $R^1$ is $CO_2H$ by conversion of the ester to the carboxylic acid, for example, by treatment with $BBr_3$ in a suitable solvent, such as dichloromethane, or with KOH or NaOH in a suitable solvent, such as dioxane, THF and/or methanol in the presence of water.

Furthermore, the compound of formula (I) where $R^1$ is $CO_2H$ may be converted into the compound of formula (I) where $R^1$ is $C(O)NR^3R^4$ by reacting the carboxylic acid with $HNR^3R^4$ in the presence of a coupling reagent, such as 1-ethyl-(3-dimethylaminopropyl)-carbodiimide, and a dehydrating agent, such as DMAP.

Alternatively, the compound of formula (I) where $R^1$ is $CO_2H$ may be converted into the compound of formula (I) where $R^1$ is $C(O)NR^3R^4$ by reacting the carboxylic acid with $R^3R^4NH_2{}^+Cl^-$ aminium chloride salt in the presence of a base, such as diisopropylethylamine, and a dehydrating agent, such as HATU.

In addition, the compound of formula (I) where X is C=O may be converted into the compound of formula (I) where X is $CH_2$ by reduction of the oxo group with, for instance, a borane reagent, such as $BH_3.Me_2S$, in a suitable solvent, such as THF.

Also, the compound of formula (I) where Y is NH may be converted into the compound of formula (I) where Y is $NR^{14}$ by reaction with $R^{14}$—Cl in the presence of a deprotonating agent, such as sodium hydride.

General Synthetic Schemes

In general, five synthetic schemes were used to obtain the compounds of formula (I).

Method A

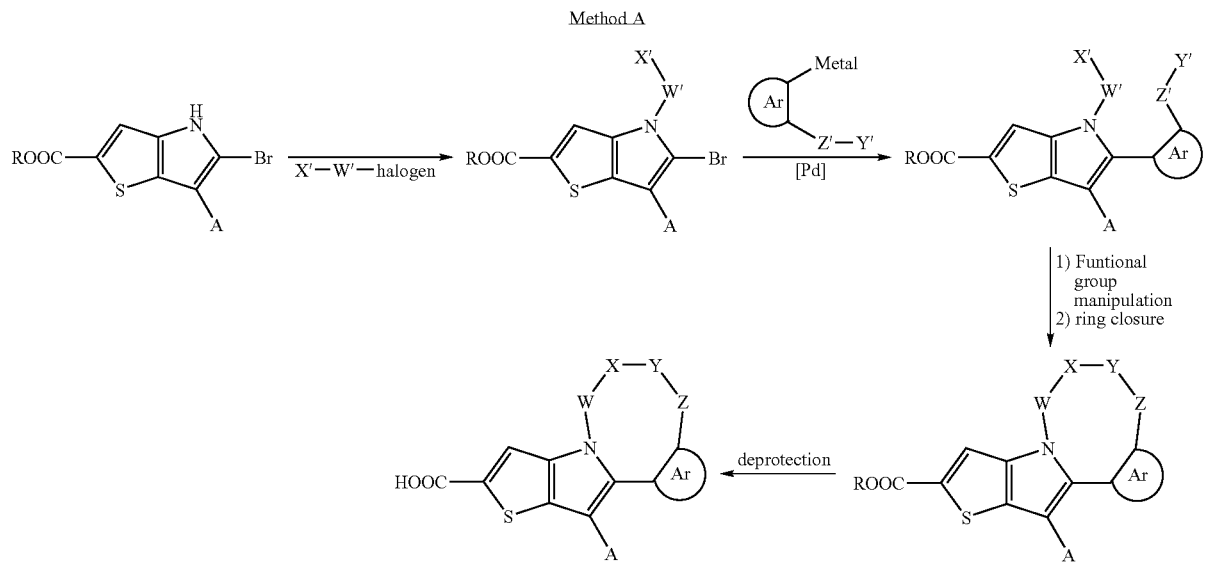

5-bromothienopyrrole intermediate (prepared as described in WO2005/023819) was functionalised on the thienopyrrole nitrogen to introduce precursor functionality W'/X' to either or both of the elements W/X of the tether. Pd mediated cross-coupling methodology (e.g., Suzuki, Stille etc) then brought in the C5 aromatic group bearing pre-cursor functionality Z'/Y' to either or both of the elements Z/Y of the tether. Functional group manipulation followed by ring closure afforded the tetracyclic system. Ester deprotection then yielded the thienopyrrole carboxylic acids.

Method B

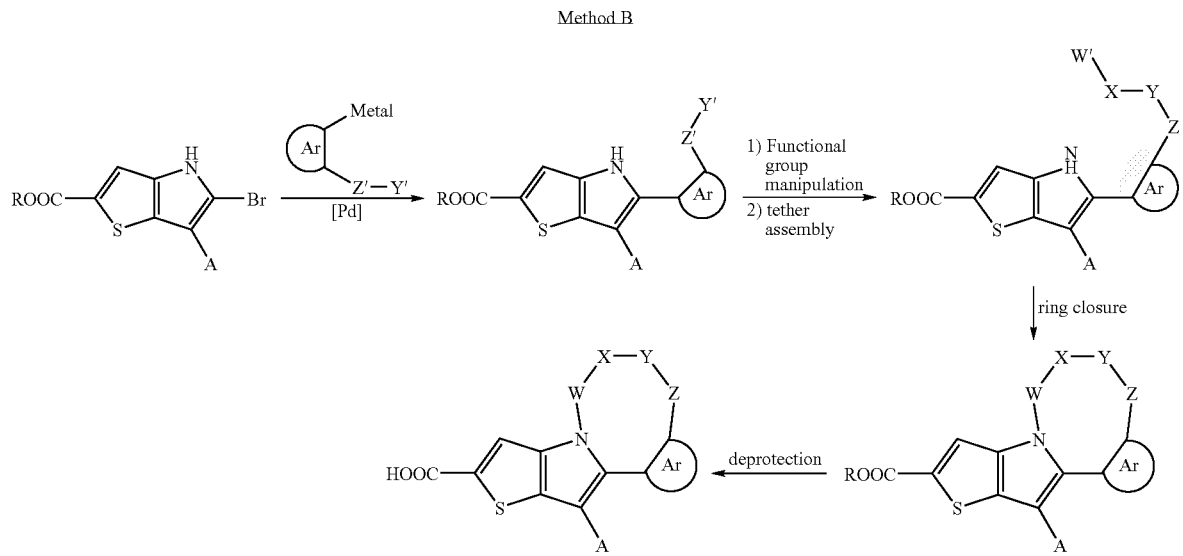

The C5 aromatic group was introduced at the outset via Pd mediated cross-coupling methodology (Suzuki, Stille etc). The tether was then built up, with cyclisation onto the thienopyrrole nitrogen finally closing the ring. Ester deprotection then yielded the thienopyrrole carboxylic acids, with the C5 aromatic group tethered to the thienopyrrole nitrogen.

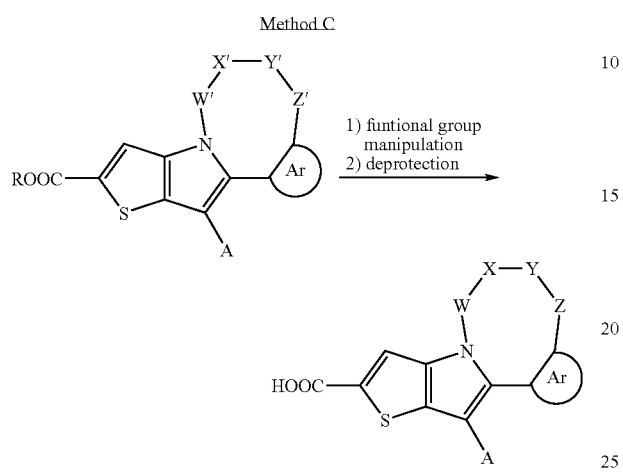

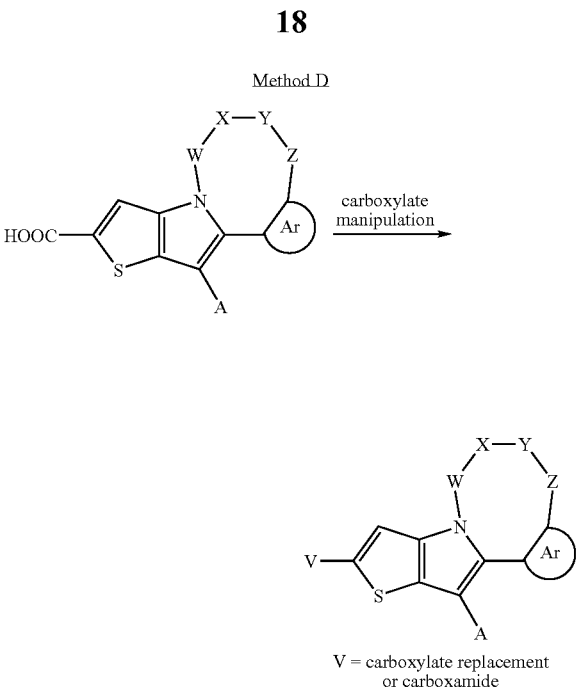

Fused tetracyclic intermediates arising from Methods A and B underwent manipulation of the functionality in the tether prior to ester deprotection to yield the C5-tethered thienopyrrole carboxylic acids.

C5-tethered thienopyrrole carboxylic acids arising from Methods A-C were further derivatised through manipulation of the carboxylate functionality to give compounds bearing a carboxylate replacement or carboxamide.

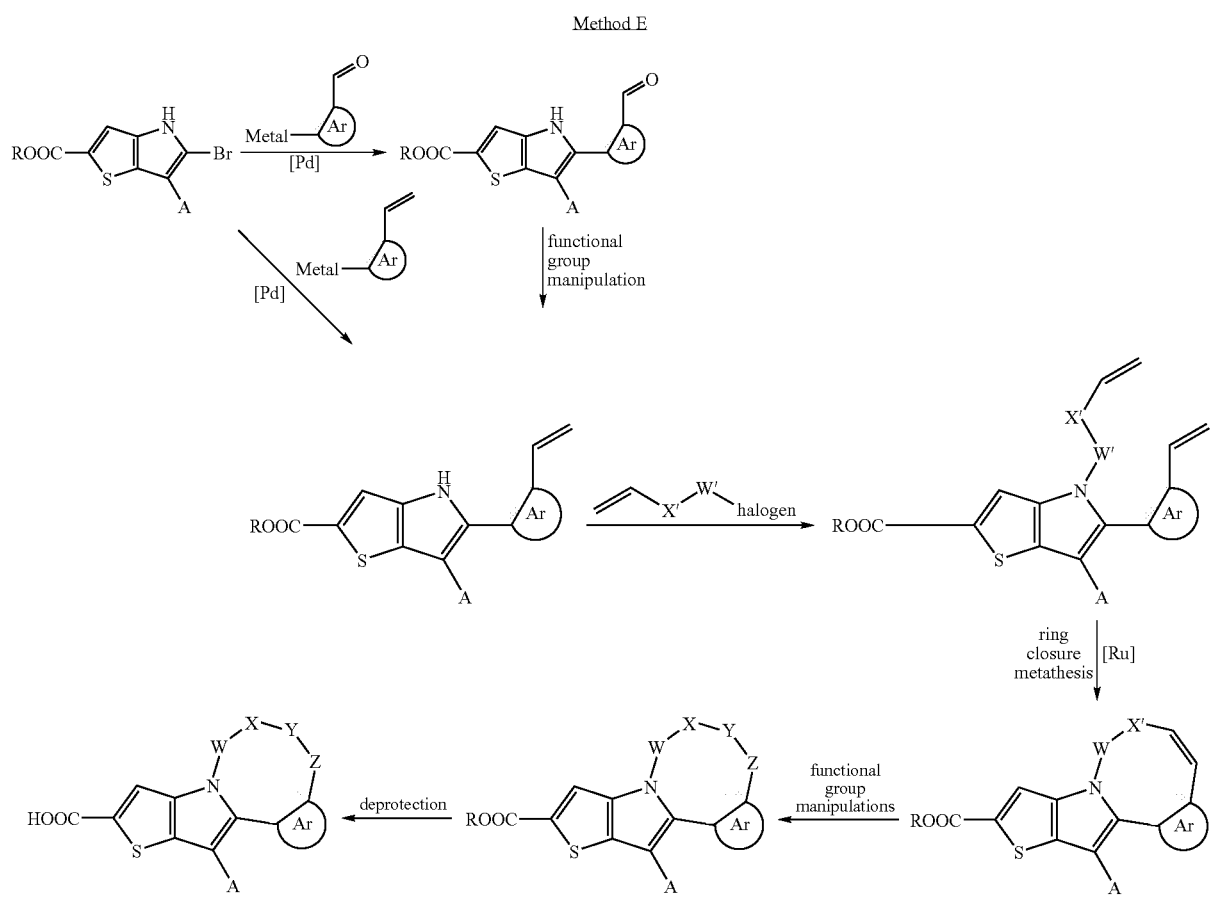

The C5 aromatic group was introduced at the outset via Pd mediated cross-coupling methodology (Suzuki, Stille, etc.). Where the vinyl arenes necessary for this coupling were not available, the corresponding formyl arenes could be used and elaborated subsequently. The thienopyrrole nitrogen was then alkylated with an ω-halogen alk-1-ene. Cyclisation in presence of a ring-closure metathesis catalyst gave the cyclic system. The newly formed double bond was then elaborated to give suitable functional groups, which in turn were then further elaborated. Ester deprotection then yielded the thienopyrrole carboxylic acids with the C5 aromatic group tethered to the thienopyrrole nitrogen.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The present invention is illustrated further by the following non-limiting examples.

The compounds of the invention were tested for inhibitory activity against the HCV RNA dependent RNA polymerase (NS5B) in an enzyme inhibition assay (example (i)) and in a cell based sub-genomic replication assay (example (ii)). The compounds generally have IC50's below 5 μM in the enzyme assay and several examples have EC50's below 2 μM in the cell based assay. Compound names in Tables and examples were generated using software from ACDLabs (version 6.0).

(i) In-Vitro HCV NS5B Enzyme Inhibition Assay

The HCV-BK cDNA sequence coding for the NS5B protein lacking of the 21 C-terminal residues (residues 1-570) was cloned in the pT7.7 vector downstream of the T7 promoter and in frame with the first ATG of the gene 10 protein of the T7 phage. A C-terminal HisTag was added to simplify purification procedure. Expression in *E. coli* BL21(DE3) was performed as described (Licia Tomei et al., 81 Journal of General Virology 759-67 (2000)). Bacteria were grown at 37° C. in standard LB medium up to an absorbance of 0.8 at 600 nm. The temperature of the culture was then lowered to 18° C. and expression induced with 0.4 mM IPTG for further 23 hrs. All the subsequent purification steps were performed at 4° C. Cells were harvested, washed with PBS (20 mM Na-phosphate [pH 7.5], 150 mM NaCl), resuspended in 100 ml of lysis buffer/liter of culture, and disrupted with a model 110S MICROFLUIDIZER. Lysis buffer contained 10 mM Tris [pH 8.0], 1 mM EDTA, 0.5 M NaCl, 50% glycerol, 10 mM β-mercaptoethanol, 0.1% n-octyl-β-D-glucopyranoside (Inalco; n-OG), COMPLETE protease inhibitor cocktail (Roche). After addition of 10 mM $MgCl_2$, the extract was incubated with 0.5 units/ml of DNaseI for 30 min. The insoluble material was pelletted by centrifugation for 60 min at 15,000 rpm in a SORVALL SS34 rotor. The clarified supernatant was incubated batchwise for 45 min with 50 ml/liter of culture of DEAE-SEPHAROSE FF resin equilibrated in lysis buffer lacking glycerol. The flow-through from the DEAE-SEPHAROSE was diluted to 0.3 M NaCl and loaded on a Ni-NTA SUPERFLOW column (Qiagen; 3 ml/liter of culture) equilibrated with A buffer+10 mM Imidazole (A buffer: 10 mM Tris [pH 8.0], 20% glycerol, 0.3 M NaCl, 0.1% n-OG, 10 mM β-mercaptoethanol) and eluted with a 50 to 500 mM imidazole gradient in A buffer. Peak fraction were collected, dialysed vs D buffer (10 mM Hepes [pH 8.0], 20% glycerol, 0.2% n-OG, 1 mM EDTA, 5 mM DTT) containing 0.15 M NaCl and loaded on HITRAP Heparin column (Amersham) equilibrated with D buffer and eluted with a 0.15 to 0.8M NaCl gradient in D buffer. The protein was stored in aliquots in liquid nitrogen.

The purified enzyme was shown to possess in vitro RNA polymerase activity using RNA as template according to a description in Journal of General Virology 81:759-767 (2000). The reference describes a polymerisation assay using poly(A) and oligo(U) as a template/primer. Incorporation of tritiated UTP is quantified by measuring acid-insoluble radioactivity. The present inventors have employed this assay to screen the various compounds described above as inhibitors of HCV RdRp.

Incorporation of radioactive UMP was measured as follows. The standard reaction (50 μl) was carried out in a buffer containing 20 mM Tris/HCl pH 7.5, 5 mM $MgCl_2$, 1 mM DTT, 10 mM NaCl, 0.01% TRITON X-100, 1 μCi [$^3$H]-UTP (40 Ci/mmol, NEN), 10 μM UTP and 10 μg/ml poly(A)/Oligo $(U)_{12}$ (1 μg/ml, Genset) as a template/primer. The final NS5B_ΔC21 enzyme concentration was 5 nM. The order of assembly was: 1) compound, 2) enzyme, 3) template/primer, 4) NTP. After 1 h. incubation at 22° C. the reaction was stopped by adding 50 μl of 20% TCA and applying samples to DE81 filters. The filters were washed thoroughly with 5% TCA containing 1M $Na_2HPO_4/NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

$$\% \text{ Residual activity} = 100/(1+[I]/IC_{50})^S$$

where [I] is the inhibitor concentration and "s" is the slope of the inhibition curve.

(ii) Cell Based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999) (EMBL-genbank No. AJ 242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International patent application WO 02/59321). Cells were seeded into 96 well plates at a density of $10^4$ cells per well in a final volume of 0.1 ml of DMEM/10% FCS. Two hours after plating, 50 μl of DMEM/10% FCS containing a 3× concentration of inhibitor were added, cells were incubated for 96 hours and then fixed for 10' with ice-cold isopropanol. Each condition was tested in duplicate and average absorbance values were used for calculations. The cells were washed twice with PBS, blocked with 5% non-fat dry milk in PBS+ 0.1% TRITON X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, $$\text{Fraction inhibition} = 1 - (A_i - b)/(A_0 - b) = [I]^n/([I]^n + IC_{50})$$

where:
- Ai=absorbance value of HBI10 cells supplemented with the indicated inhibitor concentration.
- $A_0$=absorbance value of HBI10 cells incubated without inhibitor.
- b=absorbance value of Huh-7 cells plated at the same density in the same microtiter plates and incubated without inhibitor.
- n=Hill coefficient.

(iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (Biotage corporation and Jones FLASHMASTER II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in Hertz (Hz); number of protons. Mass spectral (MS) data were obtained on a Perkin Elmer API 100, or Waters MICROMASS ZQ, operating in negative (ES$^-$) or positive (ES$^+$) ionization mode and results are reported as the ratio of mass over charge (m/z). Preparative scale HPLC separations were carried out on a Waters DELTA PREP 4000 separation module, equipped with a Waters 486 absorption detector or on a Gilson preparative system.

The following abbreviations are used in the examples, the schemes and the tables: dioxan(e): 1,4-dioxane; DIPEA: diisopropylethylamine; DMF: N,N-dimethylformamide; DMSO: dimethylsulfoxide; EtOAc: ethyl acetate; eq.: equivalent(s); h: hour(s); HATU: O-(7-azabenzotriazol-1-yl)-N,N,N',N'-tetramethyluronium hexafluorophosphate; MeCN: acetonitrile; min: minutes; MS: mass spectrum; PE: petroleum ether 30/60; quant.: quantitative; RP-HPLC: reversed phase high-pressure liquid chromatography; RP-MS-HPLC: mass-guided reversed phase high-pressure liquid chromatography; RT: room temperature; THF: tetrahydrofuran.

EXAMPLE 1

13-cyclohexyl-6-[2-(dimethylamino)ethyl]-7-oxo-5,6,7,8-tetrahydrothieno[2',3':4,5]pyrrolo[2,1-a][2,5]benzodiazocine-11-carboxylic acid Step 1: tert-butyl 6-cyclohexyl-4H-thieno[3,2-b]pyrrole-2-carboxylate A suspension of 6-cyclohexyl-4H-thieno[3,2-b]pyrrole-2-carboxylic acid (1 eq., prepared as described in WO2005/023819) in dry CH$_2$Cl$_2$ (0.19 M) was treated with tert-butyl N,N'-diisopropylimidocarbamate (2 eq.). The resulting clear solution was heated to reflux for 20 h. Addition of a further equivalent of isourea was required after 16 h to drive the reaction to complete conversion. After cooling down the solvent was evaporated in vacuo giving a residue that was purified by flash chromatography (PE:EtOAc, 10:1) affording the title compound (57%). $^1$H-NMR (400 MHz, DMSO-d$_6$, 300 K, δ) 11.12 (bs, 1H), 7.55 (s, 1H), 7.08 (s, 1H), 2.60-2.50 (m, 1H), 1.99-1.67 (m, 5H), 1.51 (s, 9H), 1.45-1.19 (m, 5H). MS (ES$^+$) m/z: 306 [M+H]$^+$.

Step 2: tert-butyl 6-cyclohexyl-4-(2-methoxy-2-oxoethyl)-4H-thieno[3,2-b]pyrrole-2-carboxylate tert-Butyl 6-cyclohexyl-4H-thieno[3,2-b]pyrrole-2-carboxylate (1 eq., from Step 1) was dissolved in anhydrous DMF (0.42 M) and sodium hydride (2 eq, 60% suspension in mineral oil) was added. The resulting suspension was stirred at RT for 30 min. Methyl bromoacetate (3 eq.) was then added and the solution was stirred at 50° C. for 1 h. After cooling down, the reaction mixture was diluted with EtOAc and washed sequentially with 1 N hydrochloric acid, saturated NaHCO$_3$ solution and brine, dried over sodium sulfate and evaporated in vacuo. Purification by flash chromatography (PE:EtOAc, 9:1) afforded the title compound (85%). $^1$H-NMR (400 MHz, DMSO-d$_6$, 300 K, δ) 7.72 (s, 1H), 7.06 (s, 1H), 5.05 (s, 2H), 3.69 (s, 3H), 2.56-2.50 (m, 1H), 1.99-1.67 (m, 5H), 1.52 (s, 9H), 1.43-1.19 (m, 5H). MS (ES$^+$) m/z: 378 [M+H]$^+$.

Step 3: tert-butyl 5-bromo-6-cyclohexyl-4-(2-methoxy-2-oxoethyl)-4H-thieno[3,2-b]pyrrole-2-carboxylate tert-Butyl 6-cyclohexyl-4-(2-methoxy-2-oxoethyl)-4H-thieno[3,2-b]pyrrole-2-carboxylate (1 eq., from Step 2) was dissolved in anhydrous CH$_2$Cl$_2$, cooled to 0° C. and treated portionwise over 40 mins with N-bromosuccinimide (1 eq.). The reaction mixture was quenched by the addition of 1 M sodium thiosulfate solution and extracted with EtOAc. The combined organic layers were washed with 1 M sodium thiosulfate solution and with brine and dried over sodium sulfate. Evaporation afforded the pure title compound (87%) as light-yellow foam. $^1$H-NMR (400 MHz, DMSO-d$_6$, 300 K, δ) 7.86 (s, 1H), 5.12 (s, 2H), 3.69 (s, 3H), 2.67-2.56 (m, 1H), 1.81-1.70 (m, 5H), 1.52 (s, 9H), 1.52-1.27 (m, 5H). MS (ES$^+$) m/z: 456, 458 [M+H]$^+$.

Step 4: tert-butyl 6-cyclohexyl-5-(2-formylphenyl)-4-(2-methoxy-2-oxoethyl)-4H-thieno[3,2-b]pyrrole-2-carboxylate tert-Butyl 5-bromo-6-cyclohexyl-4-(2-methoxy-2-oxoethyl)-4H-thieno[3,2-b]pyrrole-2-carboxylate (1 eq., from Step 3) and 2-formyl-phenylboronic acid (1.5 eq.) were dissolved in dioxane (0.1 M) and treated with 2 M Na$_2$CO$_3$ solution (2 eq.). The solution was degassed by bubbling argon through it and Pd(PPh$_3$)$_2$Cl$_2$ (0.1 eq.) was added. The reaction mixture was heated to reflux for 20 min then allowed to cool down to RT, diluted with EtOAc and washed with 1 N hydrochloric acid and with brine. The organic layer was dried over sodium sulfate, evaporated in vacuo and the residue purified by chromatography (PE:EtOAc, 9:1) to afford the pure title compound (68%) as a solid. $^1$H-NMR (400 MHz, DMSO-d$_6$, 300 K, δ) 9.70 (s, 1H), 7.96 (dd, J 7.7, 1.3, 1H), 7.91 (s, 1H), 7.84 (dt, J 7.6, 1.5, 1H), 7.80 (t, J 7.7, 1H), 7.47 (d, J 7.6, 1H), 4.93 (d, J 18.2, 1H), 4.76 (d, J 18.2, 1H), 3.48 (s, 3H), 2.15-2.08 (m, 1H), 1.73-1.02 (m, 10H), 1.52 (s, 9H). MS (ES$^+$) m/z: 482 [M+H]$^+$.

Step 5: 13-cyclohexyl-6-[2-(dimethylamino)ethyl]-7-oxo-5,6,7,8-tetrahydrothieno[2',3':4,5]pyrrolo[2,1-a][2,5]benzodiazocine-11-carboxylic acid A solution of tert-butyl 6-cyclohexyl-5-(2-formylphenyl)-4-(2-methoxy-2-oxoethyl)-4H-thieno[3,2-b]pyrrole-2-carboxylate (1 eq., from Step 4) in dry THF (0.05 M) was treated with 2-(aminoethyl)dimethylamine (1.5 eq.) at RT for 1 h. The volatile materials were evaporated in vacuo and the residue dissolved in dry methanol and treated with sodium cyanoborohydride (2 eq.) overnight at RT. The residue was diluted with EtOAc and washed with saturated NaHCO$_3$ solution and with brine, then dried over sodium sulfate and evaporated in vacuo affording tert-butyl 13-cyclohexyl-6-[2-(dimethylamino)ethyl]-7-oxo-5,6,7,8-tetrahydrothieno[2',3':4,5]pyrrolo[2,1-a][2,5]benzodiazocine-11-carboxylate. The foregoing crude compound was treated with trifluoroacetic acid/CH$_2$Cl$_2$ (1:1, 0.01 M) for 30 min at RT. The volatiles were evaporated in vacuo and the residue purified by RP-HPLC (column: Waters XTERRA PREP MS C$_{18}$, 10 μm; solvents: A: water+0.1% trifluoroacetic acid; B: MeCN+0.1% trifluoroacetic acid; 25% B in A isocratic for 3 min, linear to 20% A in B in 12 min) to afford the title compound after lyophilisation as a colourless powder (39%). $^1$H-NMR (400 MHz, DMSO-d$_6$, 300 K, δ) 9.25 (bs, 1H) 7.77-7.75 (m, 1H), 7.68 (s, 1H), 7.60-7.57 (m, 2H), 7.51-7.49 (m, 1H), 4.84 (d, J 17.3, 1H), 4.29 (d, J 14.6, 1H), 4.20 (d, J 17.3, 1H), 4.15 (d, J 14.6, 1H), 3.50-3.30 (m, 2H, hidden by the H$_2$O signal), 3.90-3.85 (m, 2H), 2.86 (s, 6H), 2.58-2.51 (m, 1H) 2.04-1.21 (m, 10H) MS (ES$^+$) m/z: 466 [M+H]$^+$.

EXAMPLE 2

13-cyclohexyl-6-[2-(dimethylamino)ethyl]-5,6,7,8-tetrahydrothieno[2',3':4,5]pyrrolo[2,1-a][2,5]benzodiazocine-11-carboxylic acid A solution of tert-butyl 13-cyclohexyl-6-[2-(dimethylamino)ethyl]-7-oxo-5,6,7,8-tetrahydrothieno[2',3':4,5]pyrrolo[2,1-a][2,5]benzodiazocine-11-carboxylate (1 eq., prepared as described in Example 1, Step 5) in dry THF (0.14 M) was treated with borane-dimethylsulfide complex (20 eq., 2 M solution in THF) overnight at RT. A solution of HCl in methanol (40 eq., 1.25 M) was added to the reaction mixture, which was then heated to reflux for 1 h. All volatiles were evaporated in vacuo and the residual material was subjected to RP-HPLC purification (column: Waters XTERRA PREP MS C$_{18}$, 10 μm; solvents: A: water+0.1% trifluoroacetic acid; B: MeCN+0.1% trifluoroacetic acid; 25% B in A isocratic for 3 min, linear to 20% A in B in 12 min) afforded the title compound after lyophilisation as a colourless powder (33%). $^1$H-NMR (500 MHz, DMSO-d$_6$, 330 K, δ) 7.91 (s, 1H), 7.63 (d, J 7.1, 1H), 7.52-7.46 (m, 2H), 7.37 (d, J 6.3, 1H), 4.40 (dd, J 15.3, 4.9, 1H), 3.86 (d, J 13.9, 1H), 3.70-3.10 (m, 4H, hidden by the H$_2$O signal), 3.05 (d, J 13.9, 1H), 3.04-2.84 (m, 2H), 2.84 (m, 6H), 2.69-2.60 (m, 1H) 2.55-2.50 (m, 1H, partially hidden by the DMSO signal), 2.02-1.09 (m, 10H). MS (ES$^+$) m/z: 452 [M+H]$^+$.

EXAMPLE 3

13-cyclohexyl-6-methyl-5,6,7,8-tetrahydrothieno[2',3':4,5]pyrrolo[2,1-a][2,5]benzodiazocine-11-carboxylic acid A solution of tert-butyl 6-cyclohexyl-5-(2-formylphenyl)-4-(2-methoxy-2-oxoethyl)-4H-thieno[3,2-b]pyrrole-2-carboxylate (1 eq., prepared as described in Example 1, Step 4) in dry methanol (0.05 M) was treated with methylamine (1.5 eq., 2 M solution in THF) at RT for 1 h. Sodium borohydride (2 eq.) was then added and the mixture stirred overnight at RT. The residue was diluted with EtOAc and washed with a saturated NaHCO$_3$ solution and with brine, then dried over sodium sulfate and evaporated in vacuo. The foregoing compound (1 eq.) was dissolved in dry THF (0.14M) was treated with borane-dimethylsulfide complex (20 eq., 2M solution in THF) overnight at RT. The reaction mixture was then treated with HCl in methanol (40 eq., 1.25 M solution) and heated to reflux for 1 h. The volatiles were evaporated in vacuo and the residue purified by RP-HPLC (column: Waters XTERRA PREP MS C$_{18}$, 10 μm; solvents: A: water+0.1% trifluoroacetic acid; B: MeCN+0.1% trifluoroacetic acid; 25% B in A isocratic for 3 min, linear to 20% A in B in 12 min) to afford the title compound after lyophilisation as a colourless powder (39%). $^1$H-NMR (400 MHz, DMSO-d$_6$, 300 K, δ) 12.83 (bs, 1H), 9.86 (bs, 1H), 8.05 (s, 1H), 7.94-7.90 (m, 1H), 7.65-7.60 (m, 2H), 7.48-7.45 (m, 1H), 4.66 (d, J 15.3, 1H), 4.39 (d, J 12.7, 1H), 3.70-3.20 (m, 4H, partially hidden by H$_2$O signal), 3.06 (s, 3H), 2.50 (m, 1H, hidden by DMSO signal), 2.03-1.36 (m, 10H). MS (ES$^+$) m/z: 395 [M+H]$^+$.

EXAMPLE 4

13-cyclohexyl-6-[2-(dimethylamino)ethyl]-3-methoxy-5,6,7,8-tetrahydrothieno[2',3':4,5]pyrrolo[2,1-a][2,5]benzodiazocine-11-carboxylic acid Step 1: tert-butyl 6-cyclohexyl-5-(2-formyl-4-methoxyphenyl)-4-(2-methoxy-2-oxoethyl)-4H-thieno[3,2-b]pyrrole-2-carboxylate tert-Butyl 5-bromo-6-cyclohexyl-4-(2-methoxy-2-oxoethyl)-4H-thieno[3,2-b]pyrrole-2-carboxylate (1 eq., prepared as described in Example 1, Step 3) and 2-formyl-4-methoxyphenylboronic acid (1.5 eq.) were dissolved in dioxane (0.1 M) and treated with 2 M Na$_2$CO$_3$ solution (2 eq.). The solution was degassed by bubbling argon through it and Pd(PPh$_3$)$_2$Cl$_2$ (0.1 eq.) was added. The reaction mixture was heated to reflux for 20 min. After cooling down to RT, the mixture was diluted with EtOAc and washed with 1 N hydrochloric acid and with brine. The organic layer was dried over sodium sulfate and evaporated in vacuo and the residue purified by chromatography (PE:EtOAc, 9:1) to afford the pure title compound (57%) as a solid. $^1$H-NMR (400 MHz, DMSO-d$_6$, 300 K, δ) 9.64 (s, 1H), 7.89 (s, 1H), 7.43 (s, 1H), 7.41-7.38 (m, 2H), 4.92 (d, J 18.0, 1H), 4.73 (d, J 18.0, 1H), 3.90 (s, 3H), 3.50 (s, 3H), 2.14-2.09 (m, 1H), 1.73-1.19 (m, 10H), 1.54 (s, 9H). MS (ES$^+$) m/z: 534 [M+Na]$^+$.

Step 2: 13-cyclohexyl-6-[2-(dimethylamino)ethyl]-3-methoxy-5,6,7,8-tetrahydrothieno[2',3':4,5]pyrrolo[2,1-a][2,5]benzodiazocine-11-carboxylic acid A solution of tert-butyl 6-cyclohexyl-5-(2-formyl-4-methoxyphenyl)-4-(2-methoxy-2-oxoethyl)-4H-thieno[3,2-b]pyrrole-2-carboxylate (1 eq., from Step 1) in dry methanol (0.05 M) was treated with 2-(aminoethyl)dimethylamine (1.5 eq.) at RT for 1 h. Sodium borohydride (2 eq.) was then added and the mixture stirred overnight at RT. The residue was diluted with EtOAc, washed with saturated NaHCO$_3$ solution and with brine, then dried over sodium sulfate and evaporated in vacuo. The foregoing compound (1 eq.) was dissolved in dry THF (0.14 M) and treated with borane-dimethylsulfide complex (20 eq., 2 M solution in THF) overnight at RT. The reaction mixture was then treated with HCl in methanol (40 eq., 1.25 M solution) and heated to reflux for 1 h. The volatiles were evaporated in vacuo and the residue purified by RP-HPLC (column: Waters XTerra Prep MS $C_{18}$, 10 μm; solvents: A: water+0.1% trifluoroacetic acid; B: MeCN+0.1% trifluoroacetic acid; 25% B in A isocratic for 3 min, linear to 20% A in B in 12 min) to afford the title compound after lyophilisation as a colourless powder (39%). $^1$H-NMR (400 MHz, DMSO-$d_6$, 300 K, δ) 7.88 (s, 1H), 7.28 (d, J 8.3, 1H), 7.16 (bs, 1H), 7.04 (d, J 8.3, 1H), 4.36 (d, J 14.1, 1H), 3.85 (s, 3H), 3.76 (d, J 12.4, 1H), 3.70-3.20 (m, 7H, partially hidden by $H_2O$ signal), 3.07-2.94 (m, 1H), 2.84 (s, 6H), 2.50 (m, 1H, hidden by the DMSO signal), 1.99-1.09 (m, 10H). MS (ES$^+$) m/z: 482 [M+H]$^+$.

EXAMPLE 5

13-cyclohexyl-6-(N,N-dimethylglycyl)-5,6,7,8-tetrahydrothieno[2',3':4,5]pyrrolo[2,1-a][2,5]benzodiazocine-11-carboxylic acid Step 1: tert-butyl 13-cyclohexyl-7-oxo-5,6,7,8-tetrahydrothieno[2',3':4,5]pyrrolo[2,1-a][2,5]benzodiazocine-11-carboxylate A solution of tert-butyl 6-cyclohexyl-5-(2-formylphenyl)-4-(2-methoxy-2-oxoethyl)-4H-thieno[3,2-b]pyrrole-2-carboxylate (1 eq., prepared as described in Example 1, Step 4) in ethanol (0.06 M) was treated with hydroxylamine hydrochloride (2 eq., 1M aqueous solution) and 2 M $Na_2CO_3$ solution (2 eq.) at RT for 1 h. The reaction mixture was extracted into EtOAc and the combined organic layers were washed with brine. Drying and evaporation afforded the oxime (0.94 eq.) as beige foam. The foregoing compound was dissolved in glacial acetic acid and hydrogenated in a Parr apparatus at 45 psi in the presence of platinum dioxide (1 eq.) for 48 h. The reaction mixture was filtered, the volatiles were evaporated in vacuo and the residue diluted with EtOAc and washed with saturated $NaHCO_3$ solution and with brine. Drying over sodium sulfate and evaporation of the solvent gave the crude primary amine which was dissolved in anhydrous methanol (0.02 M) and stirred for 1 h at RT in the presence of a catalytic amount of sodium methoxide. The volatiles were then evaporated in vacuo and the residue dissolved in EtOAc, washed with 1 M hydrochloric acid and with brine. Chromatography (PE:EtOAc, 1:1) gave the title compound (71%), as light yellow foam. $^1$H-NMR (400 MHz, DMSO-$d_6$, 300 K, δ) 8.16 (bs, 1H) 7.69 (s, 1H), 7.56-7.49 (m, 4H), 4.70 (d, J 17.8, 1H), 4.11 (d, J 17.1, 1H), 3.95-3.86 (m, 1H), 3.61-3.50 (m, 1H), 2.50 (m, 1H, hidden by DMSO signal), 2.01-1.10 (m, 10H) 1.54 (s, 9H). MS (ES$^+$) m/z: 451 [M+H]$^+$.

Step 2: 13-cyclohexyl-6-(N,N-dimethylglycyl)-5,6,7,8-tetrahydrothieno[2',3':4,5]pyrrolo[2,1-a][2,5]benzodiazocine-11-carboxylic acid A solution of tert-butyl 13-cyclohexyl-7-oxo-5,6,7,8-tetrahydrothieno[2',3':4,5]pyrrolo[2,1-a][2,5]benzodiazocine-11-carboxylate (1 eq., from Step 1) in dry THF (0.1 M) was treated with a solution of borane-dimethylsulfide complex (20 eq., 2 M solution in THF) overnight at RT. Methanol (0.1 M) was added to the reaction mixture, which was then heated to reflux for 1 h. The volatiles were evaporated in vacuo, the residue dissolved in EtOAc and washed with saturated $NaHCO_3$ solution and with brine. The amine was obtained upon evaporation as beige foam (0.62 eq.). A solution of the foregoing compound (1 eq), N,N-dimethylglycine (1.1 eq.) and N-ethyl-N-isopropylpropan-2-amine (2 eq.) in dry $CH_2Cl_2$ (0.1 M) was treated with N-[(dimethylamino)(3H-[1,2,3]triazolo[4,5-b]pyridin-3-yloxy)methylene]-N-methylmethanaminium hexafluorophosphate (1.2 eq.) and stirred at RT for 16 h. The reaction mixture was diluted with EtOAc, washed with 1 N hydrochloric acid, saturated $NaHCO_3$ solution and with brine. The crude was treated with trifluoroacetic acid/$CH_2Cl_2$ (1:1, 0.01 M) for 30 mins then evaporated in vacuo. RP-HPLC purification (column: Waters XTerra Prep MS $C_{18}$, 10 μm; solvents: A: water+0.1% trifluoroacetic acid; B: MeCN+0.1% trifluoroacetic acid; 25% B in A isocratic for 3 min, linear to 20% A in B in 12 min) afforded the title compound after lyophilisation as a greyish powder (18%). $^1$H-NMR (400 MHz, DMSO-$d_6$, 330 K, δ) 12.79 (bs, 1H), 9.55 (s, 1H), 7.94 (s, 1H), 7.81-7.74 (m, 1H), 7.63-7.39 (m, 3H), 5.16 (d, J 14.2, 1H), 4.60 (bd, J 15.1, 1H), 4.32 (d, J 16.9, 1H), 4.11 (d, J 16.9, 1H). 3.80 (bd, J 15.1, 1H), 3.64-3.53 (m, 1H), 3.53-3.35 (m, 2H, partially hidden by $H_2O$ signal), 2.86 (s, 6H), 2.50 (m, 1H, hidden by the DMSO signal), 2.08-1.07 (m, 10H). MS (ES$^+$) m/z: 466 [M+H]$^+$.

EXAMPLE 6

13-cyclohexyl-7-{[2-(dimethylamino)ethyl]amino}-7,8-dihydro-6H-thieno[2',3':4,5]pyrrolo[1,2-e][1,5]benzoxazocine-11-carboxylic acid Step 1: methyl 6-cyclohexyl-5-(2-hydroxyphenyl)-4H-thieno[3,2-b]pyrrole-2-carboxylate 4-tert-Butyl 2-methyl 5-bromo-6-cyclohexyl-4H-thieno[3,2-b]pyrrole-2,4-dicarboxylate (prepared as described in WO2005/023819) was dissolved in a mixture of $CH_2Cl_2$/trifluoroacetic acid (2:1) to give a 0.1 N solution. The solution was stirred at RT for 2 h. All volatiles were then evaporated in vacuo and the residual material was dried in vacuo overnight. The methyl 5-bromo-6-cyclohexyl-4H-thieno[3,2-b]pyrrole-2-carboxylate thus obtained was dissolved in dioxane to give a 0.1 N solution. Spray-dried potassium fluoride (3 eq.), 2-hydroxybenzene boronic acid (1.5 eq.) and bis(tri-tert-butylphosphine)palladium(0) (0.18 eq.) were added, the mixture was degassed and flushed with nitrogen. After stirring at RT for 20 min, all undissolved material was filtered off through a 0.45 μm membrane filter and the product was isolated by RP-HPLC (column: Waters XTerra Prep MS $C_{18}$, 5 μm; solvents: A: water+0.1% trifluoroacetic acid; B: MeCN+0.1% trifluoroacetic acid; 30% B in A isocratic for 3 min, linear to 1% A in B in 10 min). After lyophilisation of the product fractions, a beige residue was obtained (79%). $^1$H-NMR (400 MHz, CDCl$_3$, 300 K, δ): 8.33 (bs, 1H), 7.70 (s, 1H), 7.36-7.30 (m, 2H), 7.05-7.01 (m, 2H), 3.92 (s, 3H), 2.65-2.59 (m, 1H), 1.83-1.26 (m, 10H). MS (ES$^+$) m/z: 356 [M+H]$^+$. (ES$^-$) m/z: 354 [M−H]$^-$.

Step 2: methyl 6-cyclohexyl-5-{2-[(2S)-oxiran-2-ylmethoxy]phenyl}-4H-thieno[3,2-b]pyrrole-2-carboxylate Methyl 6-cyclohexyl-5-(2-hydroxyphenyl)-4H-thieno[3,2-b]pyrrole-2-carboxylate (from Step 1) was dissolved in DMF to give a 0.1 N solution. 2S-(+)-glycidyl-3-nitrobenzene sulfonate (1.1 eq.) and cesium fluoride (1.2 eq.) were added and the mixture was stirred at RT. After one night, additional 2S-(+)-glycidyl-3-nitrobenzene sulfonate (1.1 eq.) and cesium fluoride (1.2 eq.) were added and stirring was continued for further 8 h. All volatiles were evaporated in vacuo and the residual material was dried in vacuo overnight.

The product was isolated by chromatography (PE:EtOAc, 8:2). After evaporation of the product fractions, the product was obtained as a sticky yellow solid (67%). $^1$H-NMR (400 MHz, CDCl$_3$, 300 K, δ): 9.16 (s, 1H), 7.72 (s, 1H), 7.42-7.39 (dd, J$_{1,2}$ 7.67, J$_{1,3}$ 1.54, 1H), 7.36-7.31 (dt, J$_{1,2}$ 7.67, J$_{1,3}$ 1.75, 1H), 7.12-7.08 (m, 1H), 7.04-7.02 (d, J$_{1,2}$ 8.33, 1H), 4.40-4.36 (dd, J$_{gem}$ 11.18, J$_{vic}$ 2.20, 1H), 4.14-4.09 (m, 1H), 3.90 (s, 3H), 3.66-3.33 (m, 1H), 2.89-2.87 (t, J 4.61, 1H), 2.82-2.77 (m, 2H), 1.92-1.66 (m, 6H), 1.41-1.24 (m, 4H). MS (ES$^+$) m/z: 412 [M+H]$^+$. (ES$^-$) m/z: 410 [M−H]$^-$.

Step 3: methyl (7S)-13-cyclohexyl-7-hydroxy-7,8-dihydro-6H-thieno[2',3':4,5]pyrrolo[1,2-e][1,5]benzoxazocine-11-carboxylate Methyl 6-cyclohexyl-5-{2-[(2S)-oxiran-2-ylmethoxy]phenyl}-4H-thieno[3,2-b]pyrrole-2-carboxylate (from Step 2) was dissolved in DMF to give a 0.09 N solution. Sodium hydride (1.1 eq., 60% suspension in mineral oil) was added and the mixture was stirred at RT overnight. Acetic acid was added to quench the mixture and all volatiles were evaporated in vacuo. The residual material was co-evaporated once with toluene and then dissolved in CH$_2$Cl$_2$/methanol (1:1) to give a 0.1 N solution. Trimethylsilyl diazomethane (1 eq.) was added and the solution was stirred for 1 h. Silica gel was added into the solution to quench the reaction. The product was isolated by chromatography (PE:EtOAc, 7:3). The product was obtained as a glassy yellowish solid (48%). $^1$H-NMR (400 MHz, CDCl$_3$, 300 K, δ): 7.79 (s, 1H), 7.46-7.39 (m, 1H), 7.33-7.31 (m, 1H), 7.25-7.11 (m, 2H), 4.52-4.31 (m, 2H), 4.10-4.06 (m, 1H), 4.03-3.95 (m, 1H), 3.91 (s, 3H), 3.88-3.84 (m, 1H), 2.69-2.62 (m, 1H), 1.99-1.17 (m, 10H). MS (ES$^+$) m/z: 412 [M+H]$^+$. (ES$^-$) m/z: 410 [M−H]$^-$; 456 [M+HCOO]$^-$.

Step 4: methyl 13-cyclohexyl-7-oxo-7,8-dihydro-6H-thieno[2',3':4,5]pyrrolo[1,2-e][1,5]benzoxazocine-11-carboxylate Methyl (7S)-13-cyclohexyl-7-hydroxy-7,8-dihydro-6H-thieno[2',3':4,5]pyrrolo[1,2-e][1,5]benzoxazocine-11-carboxylate (from Step 3) was dissolved in CH$_2$Cl$_2$ to give a 0.04 N solution and Dess-Martin periodinane (1.2 eq.) was added. The solution was stirred at RT overnight. The mixture was then diluted with CH$_2$Cl$_2$, extracted with saturated NaHCO$_3$ solution, dried over sodium sulfate and evaporated in vacuo. The residual material was subjected to chromatography (PE:EtOAc, 7.5:2.5). After evaporation of the product fractions, the product was obtained as a glassy solid (67%). $^1$H-NMR (400 MHz, CDCl$_3$, 300 K, δ): 7.71 (s, 1H), 7.53-7.49 (m, 1H), 7.44-7.41 (m, 1H), 7.35-7.30 (m, 2H), 4.80-4.76 (d, J$_{gem}$ 16.93, 1H), 4.66-4.59 (2d, J$_{gem}$ 16.93, 16.17, 2H), 4.52-4.48 (d, J$_{gem}$ 16.42, 1H), 3.92 (s, 3H), 2.71-2.63 (m, 1H), 2.06-1.69 (m, 6H), 1.54-1.19 (m, 4H). MS (ES$^+$) m/z: 410 [M+H]$^+$; 428 [M+H+H$_2$O]$^+$.

Step 5: 13-cyclohexyl-7-{[2-(dimethylamino)ethyl]amino}-7,8-dihydro-6H-thieno[2',3':4,5]pyrrolo[1,2-e][1,5]benzoxazocine-11-carboxylic acid Methyl 13-cyclohexyl-7-oxo-7,8-dihydro-6H-thieno[2',3':4,5]pyrrolo[1,2-e][1,5]benzoxazocine-11-carboxylate (from Step 4) was dissolved in 1,2-dichloroethane to give a 0.01 N solution. N,N-dimethylaminoethyl amine (1.2 eq.) and sodium triacetoxyborohydride (1.2 eq.) were added and the mixture was stirred at 45° C. for 3 days. The mixture was diluted with 1,2-dichloroethane and acetic acid was added. After stirring for 10 min, all volatiles were evaporated in vacuo. The residual material was co-evaporated once with toluene, then the residue was dried in vacuo and the methyl 13-cyclohexyl-7-{[2-(dimethylamino)ethyl]amino}-7,8-dihydro-6H-thieno[2',3':4,5]pyrrolo[1,2-e][1,5]benzoxazocine-11-carboxylate thus obtained was dissolved in dioxane to give a 0.01 N solution. The solution was diluted with methanol to give a 0.0075 M solution, then 1 N KOH solution (10 eq.) was added. Water was added to dissolve the forming precipitate and the resulting solution was warmed to 50° C. overnight. The product was isolated by RP-HPLC (column: Waters XTerra Prep MS C$_{18}$, 5 µm; solvents: A: water+0.1% trifluoroacetic acid; B: MeCN+0.1% trifluoroacetic acid; 10% B in A isocratic for 3 min, linear to 1% A in B in 10 min). After lyophilisation of the product fractions, the product was obtained as a colourless amorphous solid (10%). $^1$H-NMR (500 MHz, DMSO-d$_6$+TFA, 300 K, δ): 8.00 (s, 1H), 7.51-7.48 (m, 1H), 7.32-7.30 (d, J 7.4, 1H), 7.25-7.22 (m, 2H), 4.72-4.69 (m, 1H), 4.24-4.13 (m, 2H), 3.90-3.85 (m, 1H), 3.70 (bs, 1H), 3.47-3.37 (m, 4H), 2.88 (s, 6H), 2.78-2.63 (m, 1H), 2.06-2.00 (m, 1H), 1.85-1.82 (m, 1H), 1.70-1.53 (m, 5H), 1.34-1.15 (m, 3H). MS (ES$^+$) m/z: 468 [M+H]$^+$. (ES$^-$) m/z: 466.36 [M−H]$^-$.

EXAMPLE 7

12-cyclohexyl-5-[2-(dimethylamino)ethyl]-6-oxo-6,7-dihydro-5H-thieno[2',3':4,5]pyrrolo[1,2-d][1,4]benzodiazepine-10-carboxylic acid Step 1: methyl 5-bromo-6-cyclohexyl-4H-thieno[3,2-b]pyrrole-2-carboxylate A solution (0.1 M) of methyl 5-bromo-4-(tert-butoxycarbonyl)-6-cyclohexyl-4H-thieno[3,2-b]pyrrole-2-carboxylate (prepared as described in WO2005/023819) in CH$_2$Cl$_2$ was treated with trifluoroacetic acid (1:1). The reaction mixture was stirred at RT for 1 h. All volatiles were evaporated giving a residue that was purified by flash chromatography (PE:EtOAc, 7:3) giving the title compound (79%) as solid. $^1$H-NMR (400 MHz, DMSO-d$_6$, 300 K, δ) 7.60 (s, 1H), 3.80 (s, 3H), 2.66-2.55 (m, 1H), 1.85-1.20 (m, 10H). MS (ES$^+$) m/z: 342, 344 [M+H]$^+$.

Step 2: methyl 5-bromo-4-(2-tert-butoxy-2-oxoethyl)-6-cyclohexyl-4H-thieno[3,2-b]pyrrole-2-carboxylate A solution (0.2 M) of methyl 5-bromo-6-cyclohexyl-4H-thieno[3,2-b]pyrrole-2-carboxylate (from Step 1) in dry DMF was treated with sodium hydride (2 eq., 60% suspension in mineral oil) at 0° C. The reaction mixture was stirred at RT for 30 min then tert-butyl bromoacetate (3 eq.) was added. The reaction was heated to 50° C. for 1 h. After cooling, the solution was diluted with EtOAc and 1 N hydrochloric acid was added. The organic phase was washed with 1 N hydrochloric acid, saturated NaHCO$_3$ solution and brine, dried over sodium sulfate and evaporated in vacuo to give a residue that was purified by flash chromatography (PE:EtOAc, 9:1) to afford the title compound (80%) as a solid. $^1$H-NMR (400 MHz, DMSO-d$_6$, 300 K, δ) 7.99 (s, 1H), 4.99 (s, 2H), 3.82 (s, 3H), 2.66-2.52 (m, 1H), 1.82-1.21 (m, 101H), 1.42 (s, 9H). MS (ES$^+$) m/z: 456, 458 [M+H]$^+$.

Step 3: methyl 5-{2-[(tert-butoxycarbonyl)amino]phenyl}-4-(2-tert-butoxy-2-oxoethyl)-6-cyclohexyl-4H-thieno[3,2-b]pyrrole-2-carboxylate A solution (0.15 M) of methyl 5-bromo-4-(2-tert-butoxy-2-oxoethyl)-6-cyclohexyl-4H-thieno[3,2-b]pyrrole-2-carboxylate (from Step 2) in dioxane was treated with tert-butyl-N-[2-(4,4,5,5-tetramethyl-1,3,2-dioxaborolan-2-yl)phenyl] carbamate (1.5 eq.) and 2 N Na$_2$CO$_3$ solution (6 eq.) and degassed. PdCl$_2$(PPh$_3$)$_2$ (0.2 eq.) was added and the suspension refluxed for 30 mins. After cooling, EtOAc was added and the solution was washed with water, brine, dried over sodium sulfate and evaporated in vacuo to give a residue which was purified by flash chromatography (PE:EtOAc, 95:5) to afford the title compound (89%) as a solid. $^1$H-NMR (400 MHz, DMSO-d$_6$, 300 K, δ) 8.00 (s, 1H), 7.73 (m, 2H), 7.47-7.43 (t, J 8.6, 1H), 7.27-7.23 (m, 2H), 4.73-4.49 (dd, J 20, 2H), 3.82 (s, 3H), 2.17-2.11 (m, 1H), 1.82-1.21 (m, 10H), 1.37 (s, 9H), 1.28 (s, 9H). MS (ES$^+$) m/z: 569 [M+H]$^+$.

Step 4: methyl 12-cyclohexyl-6-oxo-6,7-dihydro-5H-thieno[2',3':4,5']pyrrolo[1,2-d][1,4]benzodiazepine-10-carboxylate A solution (0.03 M) of methyl 5-{2-[(tert-butoxycarbonyl) amino]phenyl}-4-(2-tert-butoxy-2-oxoethyl)-6-cyclohexyl-4H-thieno[3,2-b]pyrrole-2-carboxylate (from Step 3) in trifluoroacetic acid/CH$_2$Cl$_2$ (1:1) was stirred at RT for 2 h and at 40° C. for 30 min. Solvents were removed in vacuo affording the title compound as a solid. $^1$H-NMR (400 MHz, DMSO-d$_6$, 300 K, δ) 10.30 (s, 1H) 8.18 (s, 1H), 7.51-7.24 (m, 4H), 5.03-4.93 (m, 1H), 4.57-4.52 (m, 1H), 3.83 (s, 3H), 2.78-2.73 (m, 1H), 1.83-1.21 (m, 10H). MS (ES$^+$) m/z: 395 [M+H]$^+$.

Step 5: methyl 12-cyclohexyl-5-[2-(dimethylamino) ethyl]-6-oxo-6,7-dihydro-5H-thieno[2',3':4,5]pyrrolo [1,2-d][1,4]benzodiazepine-10-carboxylate A solution (0.1 M) of methyl 12-cyclohexyl-6-oxo-6,7-dihydro-5H-thieno[2',3':4,5]pyrrolo[1,2-d][1,4]benzodiazepine-10-carboxylate (from Step 4) in DMF was treated with sodium hydride (1.5 eq., 60% suspension in mineral oil) at 0° C. and then stirred at RT for 30 min. 2-Chloro-N,N-dimethylethylamine (2.0 eq.) was added and the solution stirred at 45° C. for 2 h. After cooling to RT, the suspension was diluted with EtOAc and washed with water, and brine. The organic phase was dried over sodium sulfate and the solvent evaporated in vacuo to give the title compound as a solid. $^1$H-NMR (400 MHz, DMSO-d$_6$, 300 K, δ) 8.14 (s, 1H), 7.74-7.45 (m, 4H), 5.04-5.01 (d, J 12, 1H), 4.43-4.40 (d, J 12, 1H), 4.18-4.15 (m, 1H), 3.83 (s, 3H), 3.65-3.61 (m, 1H), 2.90-2.82 (m, 1H), 2.15-2.06 (m, 2H), 1.81-1.23 (m, 10H). MS (ES$^+$) m/z: 466 [M+H]$^+$.

Step 6: 12-cyclohexyl-5-[2-(dimethylamino)ethyl]-6-oxo-6,7-dihydro-5H-thieno[2',3':4,5]pyrrolo[1,2-d] [1,4]benzodiazepine-10-carboxylic acid In the preparation of methyl 12-cyclohexyl-5-[2-(dimethylamino)ethyl]-6-oxo-6,7-dihydro-5H-thieno[2',3':4,5]pyrrolo[1,2-d][1,4]benzodiazepine-10-carboxylate (see Step 5), partial hydrolysis of the methyl ester was observed in one experiment and the title compound was obtained after automated RP-MS-HPLC purification (column: Waters SYMMETRY C$_{18}$, 7 µM; solvents: A: water+0.1% trifluoroacetic acid; B: MeCN+0.1% trifluoroacetic acid; 30% B in A isocratic for 2 min, linear to 80% A in B in 14 min). The product was obtained after lyophilisation as a colourless solid (7%). $^1$H-NMR (400 MHz, DMSO-d$_6$, 300 K, δ) 9.41 (bs, 1H), 8.05 (s, 1H), 7.68-7.49 (m, 4H), 5.10-5.06 (d, J 16, 1H), 4.48-4.44 (d, J 16, 1H), 4.32-4.26 (m, 1H), 4.02-3.98 (m, 1H), 3.1 (m, 2H), 2.91-2.79 (m,1H), 2.65 (s, 6H), 2.10-1.23 (m, 10H). MS (ES$^+$) m/z: 452 [M+H]$^+$.

EXAMPLE 8

12-cyclohexyl-6-oxo-6,7-dihydro-5H-thieno[2',3':4, 5]pyrrolo[1,2-d][1,4]benzodiazepine-10-carboxylic acid In the preparation of methyl 12-cyclohexyl-5-[2-(dimethylamino)ethyl]-6-oxo-6,7-dihydro-5H-thieno[2',3':4,5]pyrrolo[1,2-d][1,4]benzodiazepine-10-carboxylate (see Example 7, Step 5), partial hydrolysis of the methyl ester was observed once and the title compound was obtained after automated RP-MS-HPLC purification (column: Waters SYMMETRY C$_{18}$, 7 µm; solvents: A: water+0.1% trifluoroacetic acid; B: MeCN+0.1% trifluoroacetic acid; 30% B in A isocratic for 2 min, linear to 80% A in B in 14 min). The product was obtained after lyophilisation as a colourless solid (38%). $^1$H-NMR (400 MHz, DMSO-d$_6$, 300 K, δ) 12.81 (bs, 1H), 10.29 (s, 1H), 8.03 (s, 1H), 7.51-7.24 (m, 4H), 4.95 (m, 1H), 4.54 (m, 1H), 2.78-2.72 (m, 1H), 2.12-1.23 (m, 10H). MS (ES$^+$) m/z: 381 [M+H]$^+$.

EXAMPLE 9

12-cyclohexyl-5-[2-(dimethylamino)ethyl]-6,7-dihydro-5H-thieno[2',3':4,5]pyrrolo[1,2-d][1,4]benzodiazepine-10-carboxylic acid Step 1: methyl 12-cyclohexyl-5-[2-(dimethylamino) ethyl]-6,7-dihydro-5H-thieno[2',3':4,5]pyrrolo[1,2-d] [1,4]benzodiazepine-10-carboxylate A solution (0.1 M) of methyl 12-cyclohexyl-5-[2-(dimethylamino)ethyl]-6-oxo-6,7-dihydro-5H-thieno[2',3':4,5] pyrrolo[1,2-d][1,4]benzodiazepine-10-carboxylate (from Example 7, Step 5) in THF was treated with borane-dimethylsulfide complex (2 M solution in THF, 20 eq.). The mixture was stirred at RT for 2 h then treated with HCl in methanol (1.25 M) and heated at 75° C. for 30 mins. The solvents were removed in vacuo and the residue taken into EtOAc and washed with saturated NaHCO$_3$ solution and brine, dried over sodium sulfate and concentrated in vacuo to give the title compound as a solid. $^1$H-NMR (400 MHz, DMSO-d$_6$, 300 K, δ) 7.99 (s, 1H), 7.40-7.36 (t, J 8, 1H), 7.29-7.27 (d, J 8, 1H), 7.23-7.21 (d, J 8, 1H), 7.14-7.10 (t, J 8, 1H), 4.17 (m, 2H), 3.82 (s, 3H), 3.43-3.39 (m, 2H), 3.20-3.17 (m, 2H), 2.70-2.67 (m, 1H), 2.32-2.23 (m, 2H), 2.01 (s, 6H), 1.81-1.23 (m, 10H). MS (ES$^+$) m/z: 452 [M+H]$^+$.

Step 2: 12-cyclohexyl-5-[2-(dimethylamino)ethyl]-6, 7-dihydro-5H-thieno[2',3':4,5]pyrrolo[1,2-d][1,4] benzodiazepine-10-carboxylic acid A solution (0.05 M) of methyl 12-cyclohexyl-5-[2-(dimethylamino)ethyl]-6,7-dihydro-5H-thieno[2',3':4,5]pyrrolo [1,2-d][1,4]benzodiazepine-10-carboxylate (from Step 1) in dioxane was treated with 1 N KOH solution (5 eq.). The mixture was stirred at 60° C. for 2 h then treated with 1 N hydrochloric acid. The solvents were removed in vacuo and the residue purified by RP-HPLC (column: Waters XTERRA PREP MS C$_{18}$, 5 µm; solvents: A: water+0.1% trifluoroacetic acid; B: MeCN+0.1% trifluoroacetic acid; 10% B in A isocratic for 1 min, linear to 50% A in B in 4 min, linear to 40% A in B in 1 min, 40% A in B isocratic for 1 min, linear to 30% A in B in 1 min) to afford the title compound (59% over two steps) after lyophilisation as a solid. $^1$H-NMR (400 MHz DMSO-d$_6$, 300K δ) 9.12 (bs, 1H), 7.93 (s, 1H), 7.48-7.23 (m, 4H), 4.18 (m, 2H), 3.46 (m, 4H), 3.13 (m, 2H), 2.67 (m, 1H), 1.78-1.27 (m, 10H). MS (ES$^+$) m/z: 438 [M+H]$^+$.

EXAMPLE 10

(2E)-3-(4-{[(1-{[(13-cyclohexyl-6-methyl-5,6,7,8-tetrahydrothieno[2',3':4,5]pyrrolo[2,1-a][2,5]benzodiazocin-11-yl)carbonyl]amino}cyclopentyl)carbonyl]amino}phenyl)acrylic acid Step 1: ethyl (2E)-3-{4-[({1-[(tert-butoxycarbonyl)amino]cyclopentyl}carbonyl)amino]phenyl}acrylate A solution (0.2 M) of ethyl 4-amino cinnamate (1 eq.) and N-tert-butyloxycarbonyl-1-aminocyclopentane carboxylic acid (1 eq.) in DMF was treated with HATU (1 eq.) followed by DIPEA (2 eq.). The mixture was heated overnight to 50° C., then all solvents were evaporated in vacuo. The residual material was dissolved in EtOAc and this solution extracted subsequently with 1N aq. HCl, sat. aq. NaHCO$_3$ and brine. The organic phase was dried over Na$_2$SO$_4$ and then treated with PE. A precipitating red oil was separated and discarded. The remaining solution was evaporated in vacuo. The residual material was dissolved in DCM and PE was added. The mixture was then slowly evaporated in vacuo until crystallisation was observed. After standing overnight, the precipitate was collected, washed with PE and dried. A pinkish-white solid was obtained (18%). $^1$H-NMR (400 MHz DMSO-d$_6$, 300 K, δ) 9.45 (s, 1H), 7.67-7.55 (m, 5H), 6.78 (bs, 1H), 6.48-6.44 (d, J 16, 1H), 4.21-4.18 (m, 2H), 2.16-2.14 (m, 2H), 1.88-1.86 (m, 2H), 1.68-1.65 (m, 4H), 1.35 (s, 9H), 1.29-1.25 (m, 2H).

Step 2: 1-[({4-[(1E)-3-ethoxy-3-oxoprop-1-en-1-yl]phenyl}amino)carbonyl]cyclopentanaminium chloride Ethyl (2E)-3-{4-[({1-[(tert-butoxycarbonyl)amino]cyclopentyl}carbonyl)amino]phenyl}acrylate (from Step 1) was dissolved in CH$_2$Cl$_2$ (0.5 M) and an excess of hydrogen chloride in diethyl ether (2.0 M) was added. The solution was left stirring overnight at RT. The precipitate formed was filtered off and dried in vacuo. A colourless solid was obtained (99%), which was used without further characterisation.

Step 3: (2E)-3-(4-{[(1-{[(13-cyclohexyl-6-methyl-5,6,7,8-tetrahydrothieno[2',3':4,5]pyrrolo[2,1-a][2,5]benzodiazocin-11-yl)carbonyl]amino}cyclopentyl)carbonyl]amino}phenyl)acrylic acid A solution of 13-cyclohexyl-6-methyl-5,6,7,8-tetrahydrothieno[2',3':4,5]pyrrolo[2,1-a][2,5]benzodiazocine-11-carboxylic acid (1 eq, from Example 3), 1-[({4-[(1E)-3-ethoxy-3-oxoprop-1-en-1-yl]phenyl}amino)carbonyl]cyclopentanaminium chloride (1.3 eq.) and DIPEA (4 eq) in anhydrous DMF (0.025 M) was treated with HATU (1.3 eq.) and stirred overnight at 40° C. The reaction mixture was then diluted with EtOAc, washed with aqueous HCl (1M solution), aqueous NaHCO$_3$ (saturated solution) and brine. The foregoing compound (1 eq.) was dissolved in THF/MeOH/H$_2$O (4:1:1, 0.025 M) and treated with LiOH.H$_2$O (2 eq) at RT for 3 h. The acidified (1N HCl) reaction mixture was purified by RP-HPLC (Conditions: Column: Waters X-TERRA MS C18, 10 micron, 19×150 mm; flow: 20 mL/min; Gradient: A: H$_2$O+0.1% TFA; B: MeCN+0.1% TFA; 75% A isocratic for 3 min, linear to 20% A in 12 min) to afford, after freeze-drying, the title compound (0.16 eq) as a colourless powder. $^1$H NMR (400 MHz, DMSO, 300 K, δ) 12.36 (bs, 1H), 10.02 (bs, 1H), 9.68 (s, 1H), 8.31 (s, 1H), 8.06 (s, 1H), 7.92-7.47 (m, 9H), 6.40 (d, J 15.8, 1H), 4.47-4.39 (m, 2H), 4.02-3.15 (m, 4H, partially hidden by H$_2$O signal), 3.07 (s, 3H), 2.50 (m, 1H, hidden by the DMSO signal), 2.38-1.05 (m, 18H); MS (ES$^+$) m/z 651 (M)$^+$.

EXAMPLE 11

Preparation of 12-cyclohexyl-5-(2-pyrrolidin-1-ylethoxy)-6,7-dihydro-5H-thieno[2',3':4,5]pyrrolo[2,1-a][2]benzazepine-10-carboxylic acid and 12-cyclohexyl-6-(2-pyrrolidin-1-ylethoxy)-6,7-dihydro-5H-thieno[2',3':4,5]pyrrolo[2,1-a][2]benzazepine-10-carboxylic acid Step 1: methyl 6-cyclohexyl-5-(2-vinylphenyl)-4H-thieno[3,2-b]pyrrole-2-carboxylate Methyl 5-bromo-6-cyclohexyl-4H-thieno[3,2-b]pyrrole-2-carboxylate (prepared as described in Example 7, Step 1) and (2-vinylphenyl)boronic acid (1.5 eq.) were dissolved in dioxane (0.06 M) and 2M aq. Na$_2$CO$_3$ (6 eq.) was added. The solution was degassed by bubbling argon, Pd(PPh$_3$)$_2$Cl$_2$ (0.2 eq.) was added, and the reaction mixture was placed in an oil bath preheated to 110° C. and stirred for 1 h; after removing all volatiles the title compound was isolated by chromatography (PE/EtOAc 10:1). Yield: 71%. $^1$H-NMR (400 MHz, CDCl$_3$, 300 K, δ) 8.16 (bs, 1H), 7.69 (d, 1H, J 7.9), 7.68 (s, 1H), 7.45-7.35 (m, 3H), 6.67 (dd, 1H, J 17.5, 11.0), 5.74 (d, 1H, J 17.5), 5.25 (d, 1H, J 11.0), 3.91 (s, 3H), 2.54-2.47 (m, 1H), 1.81-1.23 (m, 10H); MS (ES$^+$) m/z 366 (M+H)$^+$.

Step 2: methyl 4-allyl-6-cyclohexyl-5-(2-vinylphenyl)-4H-thieno[3,2-b]pyrrole-2-carboxylate To a 0.1M solution of methyl 6-cyclohexyl-5-(2-vinylphenyl)-4H-thieno[3,2-b]pyrrole-2-carboxylate in dry DMF, 60% NaH (1.2 eq.) in mineral oil was added; when gas evolution had ceased, allyl bromide (1.3 eq.) was added, and the suspension was stirred at RT for 1 h. All volatiles were evaporated and the title compound was isolated by chromatography (PE/Et$_2$O 20:1). Yield: 98%. $^1$H-NMR (400 MHz, CDCl$_3$, 300 K, δ) 7.73 (d, 1H, J 7.6), 7.70 (s, 1H), 7.47 (t, 1H, J 7.6), 7.36 (t, 1H, J 7.6), 7.25 (d, 1H, J 7.6), 6.48 (dd, 1H, J 17.8, 11.4), 5.72 (d, 1H, J 17.8), 5.80-5.69 (m, 1H), 5.20 (d, 1H, J 11.4), 5.09 (dd, 1H, J 10.3, 1.1), 4.97 (dd, 1H, J 17.1, 1.1), 4.36 (dd, 1H, J 16.2, 5.6), 4.23 (dd, 1H, J 16.2, 5.6), 3.92 (s, 3H), 2.35-2.24 (m, 1H), 1.75-1.16 (m, 10H).

Step 3: Methyl 12-cyclohexyl-7H-thieno[2',3':4,5]pyrrolo[2,1-a][2]benzazepine-10-carboxylate Methyl 4-allyl-6-cyclohexyl-5-(2-vinylphenyl)-4H-thieno[3,2-b]pyrrole-2-carboxylate was dissolved in DCM (0.02M) and treated with Zhan catalyst (dichloro(5-chloro-2-isopropoxybenzylidene)(1,3-dimesityl-1,3-dihydro-2H-imidazol-2-ylidene)ruthenium; RC-301; 0.3 eq.) at 35° C. for 2 h. After removal of the solvent the residue was purified by chromatography (PE/EtOAc 14:1) to afford the title compound in 83% yield. $^1$H-NMR (400 MHz, CDCl$_3$, 300 K, δ) 7.74 (s, 1H), 7.57-7.56 (m, 1H), 7.45-7.35 (m, 3H), 6.82 (d, 1H, J 10.4), 6.30-6.25 (m, 1H), 4.47 (bs, 2Hs), 3.93 (s, 3H), 2.83-2.76 (m, 1H), 1.85-1.29 (m, 10H); MS (ES$^+$) m/z 378 (M+H)$^+$.

Step 4: 12-cyclohexyl-5-(2-pyrrolidin-1-ylethoxy)-6, 7-dihydro-5H-thieno[2',3':4,5]pyrrolo[2,1-a][2]benzazepine-10-carboxylic acid and 12-cyclohexyl-6-(2-pyrrolidin-1-ylethoxy)-6,7-dihydro-5H-thieno[2',3': 4,5]pyrrolo[2,1-a][2]benzazepine-10-carboxylic acid Borane dimethylsulfide complex (1.6 eq., 2M solution in THF) was added to a 0.1M solution of methyl 12-cyclohexyl-7H-thieno[2',3':4,5]pyrrolo[2,1-a][2]benzazepine-10-carboxylate in THF, and the mixture was stirred for 3 h at RT; 3M aq NaOH (3 eq.) and 35% $H_2O_2$ (3.5 eq.) were added at 0° C., and stirring was continued overnight at RT. After diluting with sat. $NaHCO_3$ the aq. phase was extracted with EtOAc, the organic phase was washed with water and brine, dried over $Na_2SO_4$ and concentrated to give a 4:1 mixture of methyl 12-cyclohexyl-5-hydroxy-6,7-dihydro-5H-thieno[2',3':4,5] pyrrolo[2,1-a][2]benzazepine-10-carboxylate and methyl 12-cyclohexyl-6-hydroxy-6,7-dihydro-5H-thieno[2',3':4,5] pyrrolo[2,1-a][2]benzazepine-10-carboxylate. The foregoing crude material was dissolved in toluene (0.05M), 40% aq. NaOH (15 eq.) and tetrabutyl ammonium bromide (0.25 eq.) were added, and the mixture was stirred for 30 min; 1-(2-chloroethyl)pyrrolidine hydrochloride (3 eq.) was added and the resulting mixture heated at 70° C. for 2 days, with addition of further 5 eq. 40% aq. NaOH twice; evaporation to dryness gave a residue from which the two regioisomers were separated by RP-HPLC (combined overall yield 26%).

12-Cyclohexyl-5-(2-pyrrolidin-1-ylethoxy)-6,7-dihydro-5H-thieno[2',3':4,5]pyrrolo[2,1-a][2]benzazepine-10-carboxylic acid (major): $^1$H-NMR (400 MHz, DMSO-$d_6$, 300 K, δ) 9.45 (bs, 1H), 7.87 (s, 1H), 7.57-7.44 (m, 4H), 4.40-1.22 (m, 28H); MS (ES$^+$) m/z 479 (M+H)$^+$.

12-Cyclohexyl-6-(2-pyrrolidin-1-ylethoxy)-6,7-dihydro-5H-thieno[2',3':4,5]pyrrolo[2,1-a][2]benzazepine-10-carboxylic acid (minor): $^1$H-NMR (400 MHz, DMSO-$d_6$, 300 K, some signals obscured by water signal, δ) 7.95 (s, 1H), 7.46-7.35 (m, 4H), 6.56-6.53 (m, 1H), 4.61-4.58 (m, 1H), 4.15-4.06 (m, 1H), 3.93-3.55 (m, 3H), 3.16-3.01 (m, 2H), 2.74-2.67 (m, 1H), 2.21-1.50 (m, 10H), 1.38-1.04 (m, 3H); MS (ES$^+$) m/z 479 (M+H)$^+$.

Step 5: (+)-12-Cyclohexyl-5-(2-pyrrolidin-1-ylethoxy)-6,7-dihydro-5H-thieno[2',3':4,5]pyrrolo[2, 1-a][2]benzazepine-10-carboxylic acid and (−)-12-Cyclohexyl-5-(2-pyrrolidin-1-ylethoxy)-6,7-dihydro-5H-thieno[2',3':4,5]pyrrolo[2,1-a][2]benzazepine-10-carboxylic acid 12-Cyclohexyl-5-(2-pyrrolidin-1-ylethoxy)-6,7-dihydro-5H-thieno[2',3':4,5]pyrrolo[2,1-a][2]benzazepine-10-carboxylic acid was subjected to chiral HPLC (CHIRALPAK AD, 0.2% TFA in hexane/0.2% TFA in EtOH+3% MeOH, 9:1). The fractions containing the enantiomers were evaporated separately i. vac. to give the two title compounds. (+)-enantiomer: 92% ee; (−)-enantiomer: 95% ee.

EXAMPLE 12

Preparation of 12-cyclohexyl-5-[2-(diethylamino) ethyl]-4,5,6,7-tetrahydrothieno[2,3-f]thieno[2',3':4,5] pyrrolo[1,2-d][1,4]diazocine-10-carboxylic acid Step 1: Methyl 6-cyclohexyl-5-(3-formyl-2-thienyl)-4-(2-methoxy-2-oxoethyl)-4H-thieno[3,2-b]pyrrole-2-carboxylate Methyl 5-bromo-6-cyclohexyl-4-(2-methoxy-2-oxoethyl)-4H-thieno[3,2-b]pyrrole-2-carboxylate (prepared in analogy to Example 7, Step 2, substituting tert-butyl bromoacetate with methyl bromo acetate) and (3-formyl-2-thienyl)boronic acid (1.2 eq.) were dissolved in dioxane (0.1 M) and treated with spray-dried KF (3.3 eq.). The solution was degassed by bubbling argon and Pd(t-Bu$_3$P)$_2$ (0.24 eq.) was added, and the reaction mixture was left stirring overnight; the mixture was then absorbed on silica gel and the title compound isolated by chromatography (PE/EtOAc 9:1). Yield: 65%. $^1$H-NMR (400 MHz, CDCl$_3$, 300 K, δ) 9.62 (s, 1H), 7.63 (s, 1H), 7.61 (d, 1H, J 5.5), 7.50 (d, 1H, J 5.5), 4.62 (s, 2H), 3.91 (s, 3H), 3.67 (s, 3H), 2.46-2.37 (m, 1H), 1.80-0.80 (m, 10H); MS (ES$^+$) m/z 446 (M+H)$^+$.

Step 2: 12-cyclohexyl-5-[2-(diethylamino)ethyl]-4,5, 6,7-tetrahydrothieno[2,3-f]thieno[2',3':4,5]pyrrolo[1, 2-d][1,4]diazocine-10-carboxylic acid Methyl 6-cyclohexyl-5-(3-formyl-2-thienyl)-4-(2-methoxy-2-oxoethyl)-4H-thieno[3,2-b]pyrrole-2-carboxylate and N,N-diethylaminoethylamine (10 eq.) were dissolved in THF (0.08 M) and the pH adjusted with AcOH to 6; the solution was left stirring for 4 h, then all volatiles were evaporated i. vac. The residual oil was dissolved in MeOH (0.08M), NaCNBH$_3$ (4 eq.) was added, and the mixture was stirred overnight at RT to give methyl 6-cyclohexyl-5-[3-({[2-(diethylamino)ethyl]amino}methyl)-2-thienyl]-4-(2-methoxy-2-oxoethyl)-4H-thieno[3,2-b]pyrrole-2-carboxylate. Under the reaction conditions the latter partially closed to afford methyl 12-cyclohexyl-5-[2-(diethylamino)ethyl]-6-oxo-4,5,6,7-tetrahydrothieno[2,3-f]thieno[2',3':4,5]pyrrolo[1,2-d][1,4]diazocine-10-carboxylate; to drive this reaction to completion a catalytic amount of NaOMe was added and stirring was continued at 40° C. for 4 days. To a 0.05M solution of the foregoing amide in dry THF a 2M solution of borane-dimethylsulfide complex (13 eq.) in THF was added and the mixture was stirred for 1 h; after evaporation of all volatiles the residue containing (methyl 12-cyclohexyl-5-[2-(diethylamino) ethyl]-4,5,6,7-tetrahydrothieno[2,3-f]thieno[2',3':4,5]pyrrolo[1,2-d][1,4]diazocine-10-carboxylate) was suspended in MeOH (0.03M) and water. The pH was adjusted with LiOH to 9. The solution was left stirring at RT. Then an excess of 1N KOH-solution was added and the mixture was warmed to 50° C. and stirred for 2 h; the title compound (24%) was isolated by prep RP-HPLC. $^1$H-NMR (400 MHz, DMSO-$d_6$, 330 K, δ) 7.67 (d, 1H, J 5.1), 7.18 (d, 1H, J 5.1), 3.15-3.12 (m, 2H), 3.09-3.05 (m, 5H), 2.87-2.81 (m, 2H), 1.79-1.63 (m, 8H), 1.30-1.10 (m, 14H); MS (ES$^+$) m/z 486 (M+H)$^+$.

EXAMPLE 13

Preparation of 13-cyclohexyl-6-[(3S)-1-isopropylpyrrolidin-3-yl]-5,6,7,8-tetrahydrothieno[2',3':4,5] pyrrolo[2,1-a][2,5]benzodiazocine-11-carboxylic acid Step 1: methyl 6-cyclohexyl-5-(2-formylphenyl)-4-(2-methoxy-2-oxoethyl)-4H-thieno[3,2-b]pyrrole-2-carboxylate Methyl 5-bromo-6-cyclohexyl-4-(2-methoxy-2-oxoethyl)-4H-thieno[3,2-b]pyrrole-2-carboxylate (prepared by analogy to Example 7, Step 2, substituting tert-butyl bromoacetate with methyl bromo acetate), 2-formyl benzene boronic acid (1.3 eq.), KF (3.2 eq.) and Pd(t-Bu$_3$P)$_2$ (0.2 eq.) were mixed in dioxane (0.1M). The mixture was degassed, flushed with nitrogen and left stirring for 5 h at RT. Then all volatiles were evaporated i. vac. and the residual material was isolated by chromatography (PE:EtOAc, 9:1). The product was obtained as a yellowish solid (80%). MS (ES$^+$) m/z 440 (M+H)$^+$.

Step 2: methyl 6-cyclohexyl-5-[2-({[(3S)-1-isopropylpyrrolidin-3-yl]amino}methyl)phenyl]-4-(2-methoxy-2-oxoethyl)-4H-thieno[3,2-b]pyrrole-2-carboxylate Methyl 6-cyclohexyl-5-(2-formylphenyl)-4-(2-methoxy-2-oxoethyl)-4H-thieno[3,2-b]pyrrole-2-carboxylate was dissolved in MeOH (0.05M) and (3S)-1-isopropylpyrrolidin-3-amine dihydrochloride (1.2 eq.; prepared in two steps from commercial (S)-3-(tert.-butyloxycarbonylamino)pyrrolidine by reductive amination with acetone and acidic cleavage of the protecting group) in MeOH was added. The pH was adjusted with sodium triacetoxyborohydride and NEt$_3$ to 5. The mixture was left stirring for 2 h, then NaCNBH$_3$ (2 eq.) was added and stirring was continued for 3 h. All volatiles were evaporated i. vac, the residual material was purified by chromatography (EtOAc+1% NEt$_3$, then EtOAc+1% NEt$_3$+10% MeOH). After evaporation of the solvents a glassy solid was obtained (84%). $^1$H-NMR (400 MHz, CDCl$_3$, 300 K, δ) 7.62 (s, 1H), 7.55 (dd 1H, J$_2$ 7.23, J$_3$ 2.85), 7.45 (dt, 1H, J$_2$ 7.45, J$_3$ 0.87), 7.33 (t, 1H, J 7.46), 7.21 (d, 1H, J 7.45), 4.48 (2d, 2H, J 3.95, J 2.85), 3.90 (s, 3H), 3.67 (s, 3H), 3.53-3.51 (m, 2H), 3.20-3.18 (m, 1H), 2.80-2.76 (m, 1H), 2.57-2.52 (m, 2H), 2.30-2.19 (m, 2H), 2.13-1.10 (m, 14H), 1.05-1.01 (m, 6H); MS (ES$^+$) m/z 552 (M+H)$^+$;

Step 3: 13-cyclohexyl-6-[(3S)-1-isopropylpyrrolidin-3-yl]-5,6,7,8-tetrahydrothieno[2',3':4,5]pyrrolo[2,1-a][2,5]benzodiazocine-11-carboxylic acid Methyl 6-cyclohexyl-5-[2-({[(3S)-1-isopropylpyrrolidin-3-yl]amino}methyl)phenyl]-4-(2-methoxy-2-oxoethyl)-4H-thieno[3,2-b]pyrrole-2-carboxylate was dissolved in MeOH/THF/water and LiOH monohydrate (1.04 eq.) was added to the solution. The mixture was left stirring at RT for 5 h. All volatiles were evaporated i. vac. and the residual material was dried i. vac. The crude material was redissolved in DMF, HATU (1.2 eq.) and DIPEA (3.6 eq.) were added and the mixture was left stirring overnight. All volatiles were evaporated i. vac. and the residual material was filtered with EtOAc/PE+1% NEt$_3$ through silica gel. After evaporation of the solvents the crude product was dissolved in THF and 2M borane dimethylsulfide complex in THF (20 eq.) was added. After 1 h all volatiles were evaporated i. vac. and the residual material was dissolved in an excess of 1.25M HCl in MeOH. The solution was warmed to 70° C. and evaporated slowly to dryness. The crude residue was dissolved in dioxane and an excess of 1N aq. KOH-solution was added. The mixture was left stirring over night and then warmed for 2 h to 50° C. The product was then isolated by prep. RP-HPLC. After lyophilisation of the product fractions a colourless solid was obtained (42%). $^1$H-NMR (400 MHz, DMSO-d$_6$, 330 K, mixture of atropisomers, δ) 7.90-7.88 (2s, 1H); 7.53-7.47 (m, 3H), 7.39-7.37 (2s, 1H), 4.59-4.48 (m, 1H), 3.91-3.42 (m, 5H), 3.30-3.18 (m, 1H), 3.10-2.67 (m, 2H), 2.60-2.51 (m, 3H), 2.33-2.15 (m, 2H), 2.03-2.00 (m, 1H), 1.85-1.82 (m, 1H), 1.74-1.65 (m, 3H), 1.59-1.43 (m, 2H), 1.36-1.10 (m, 10H); MS (ES$^+$) m/z 492 (M+H)$^+$; [α]$_D^{20}$ –4.8° (c=1.0 in MeCN).

EXAMPLE 14

Preparation of 6-[2-(dimethylamino)ethyl]-13-(2-fluorocyclohexyl)-5,6,7,8-tetrahydrothieno[2',3':4,5]pyrrolo[2,1-a][2,5]benzodiazocine-11-carboxylic acid Step 1: methyl 5-methyl-4-nitrothiophene-2-carboxylate Fuming nitric acid (3 eq.) was added dropwise to Ac$_2$O (5 eq.) at –20° C., then 5-methyl-2-thiophenecarboxylic acid (1 eq.) was added portion-wise and the mixture placed in an ice bath. After stirring at 0° C. for 1.5 h the reaction mixture was poured into ice, and when the ice was molten the precipitate was filtered off (66%). To a 1M solution of the latter in MeOH, conc. H$_2$SO$_4$ (1.4 eq.) was added at RT. The mixture was stirred overnight at reflux. All volatiles were evaporated i. vac., then the residual material was mixed with water and the resulting solution extracted with EtOAc; the organic layer was washed with sat. NaHCO$_3$ and brine, dried over Na$_2$SO$_4$ and concentrated (98%). $^1$H-NMR (400 MHz, CDCl$_3$, 300 K, δ) 8.21 (1H, s), 3.93 (s, 3H), 2.85 (s, 3H).

Step 2: Methyl 5-[(E)-2-(dimethylamino)ethenyl]-4-nitrothiophene-2-carboxylate

A 0.3M solution of methyl 5-methyl-4-nitrothiophene-2-carboxylate in dry DMF was treated with N,N-dimethylformamide dimethoxy acetal (10 eq.) overnight at 110° C. Evaporation to dryness gave a residue that was used as such. $^1$H-NMR (300 MHz, CDCl$_3$, 300 K, δ) 8.32 (s, 1H), 7.53 (d, 1H, J 13.4), 6.77 (d, 1H, J 13.4), 4.08 (s, 3H), 3.29 (s, 6H); MS (ES$^+$) m/z 257 (M+H)$^+$.

Step 3: methyl 4H-thieno[3,2-b]pyrrole-2-carboxylate

10% Pd/C (0.4 eq.) and ammonium formate (6 eq.) were added to a 0.1M solution of methyl 5-[(E)-2-(dimethylamino)ethenyl]-4-nitrothiophene-2-carboxylate in MeOH/EtOAc 1:1, and the mixture was heated to reflux for 30 min; after cooling to RT the flask was flushed with nitrogen a few times, then the reaction mixture was filtered and the solution evaporated i. vac. The residue was dissolved in EtOAc and washed with water and brine, dried over Na$_2$SO$_4$, and concentrated i. vac. The crude product (50% over two steps) was used as such. $^1$H-NMR (400 MHz, CDCl$_3$, 300 K, δ) 8.44 (bs, 1H), 7.72 (s, 1H), 7.21 (bs, 1H), 6.50 (bs, 1H), 3.91 (s, 3H); MS (ES$^+$) m/z 182 (M+H)$^+$.

Step 4: methyl 6-cyclohex-1-en-1-yl-4H-thieno[3,2-b]pyrrole-2-carboxylate

NaOMe (3 eq.) and cyclohexanone (3 eq.) were added at RT to a 0.2M solution of methyl 4H-thieno[3,2-b]pyrrole-2-carboxylate in MeOH, and the mixture was refluxed for two days (1 additional eq. of each reagent was added twice). The reaction mixture was concentrated to half the volume, and poured into 6N HCl with ice; a mixture of the title compound and the corresponding carboxylic acid was obtained by filtration. 2M TMS-diazomethane in hexanes was slowly added at RT to a 0.15M suspension of the foregoing precipitate in toluene:MeOH 6:1; a water bath was used to prevent excessive warming of the reaction mixture. Evaporation to dryness after 10 min yielded the title compound, which was purified by precipitation in PE containing some Et$_2$O. Yield: (82%).

¹H-NMR (300 MHz, CDCl₃, 300 K, δ) 8.28 (bs, 1H), 7.69 (s, 1H), 7.14 (bs, 1H), 6.03 (bs, 1H), 3.90 (s, 3H), 2.41 (bs, 2H), 2.27 (bs, 2H), 1.84-1.76 (m, 2H), 1.73-1.65 (m, 2H); MS (ES⁺) m/z 262 (M+H)⁺.

Step 5: methyl 6-(2-hydroxycyclohexyl)-4H-thieno[3,2-b]pyrrole-2-carboxylate

A 2M solution in THF of borane dimethylsulfide complex (1.5 eq.) was added at 0° C. to a 0.1M solution of methyl 6-cyclohex-1-en-1-yl-4H-thieno[3,2-b]pyrrole-2-carboxylate in dry THF, and the mixture was stirred at RT for 7 h. After cooling to 0° C., the mixture was treated with 3M aq. NaOH (3 eq.) and 35% hydrogen peroxide (4 eq.). The mixture was allowed to warm to RT overnight. Aq. NaHCO₃-solution was added and the mixture was extracted with EtOAc; the organic layer was washed with water and brine, dried over Na₂SO₄ and concentrated. Chromatography (PE/EtOAc) afforded the title compound (56%). ¹H-NMR (300 MHz, CDCl₃, 300 K, δ) 8.30 (bs, 1H), 7.68 (s, 1H), 7.08 (d, 1H, J 2.0), 3.89 (s, 3H), 3.70-3.65 (m, 1H), 2.58-2.49 (m, 1H), 2.16-2.12 (m, 1H), 1.98-1.65 (m, 4H), 1.47-1.23 (m, 3H); MS (ES⁺) m/z 280 (M+H)⁺.

Step 6: methyl 6-(2-fluorocyclohexyl)-4H-thieno[3,2-b]pyrrole-2-carboxylate

Diethylaminosulfur trifluoride (1.2 eq.) was added at −60° C. to a 0.1M solution of methyl 6-(2-hydroxycyclohexyl)-4H-thieno[3,2-b]pyrrole-2-carboxylate in dry EtOAc, and the mixture was stirred at this temperature for 1 h, then allowed to warm slowly to RT. Aq. NaHCO₃-solution was added and the mixture was extracted with EtOAc; the organic layer was washed with water and brine, dried on Na₂SO₄ and concentrated. Chromatography (PE/EtOAc) afforded the title compound (73%). ¹H-NMR (300 MHz, CDCl₃, 300 K, δ) 8.31 (bs, 1H), 7.67 (s, 1H), 7.06 (s, 1H), 4.53 (dtd, 1H, J 48.6, 10.1, 4.5), 3.88 (s, 3H), 2.88-2.77 (m, 1H), 2.41-1.17 (m, 8H); MS (ES⁺) m/z 282 (M+H)⁺.

Step 7: methyl 6-(2-fluorocyclohexyl)-4-(2-methoxy-2-oxoethyl)-4H-thieno[3,2-b]pyrrole-2-carboxylate 60% NaH in mineral oil (2 eq.) was added at RT to a 0.25M solution of methyl 6-(2-fluorocyclohexyl)-4H-thieno[3,2-b]pyrrole-2-carboxylate in dry DMF, after few min methyl bromoacetate (3 eq.) was added and the mixture was stirred at 60° C. for 1 h and left overnight at RT. After dilution with EtOAc, the organic layer was washed with 1N HCl, sat. NaHCO₃ and brine, dried over Na₂SO₄ and concentrated. Chromatography (PE/EtOAc) afforded the title compound (53%). ¹H-NMR (400 MHz, CDCl₃, 300K, δ) 7.60 (s, 1H), 6.92 (s, 1H), 4.74 (s, 2H), 4.50 (dtd, 1H, J 48.9, 10.3, 4.5), 3.88 (s, 3H), 3.77 (s, 3H), 2.85-2.76 (m, 1H), 2.25-2.11 (m, 2H), 1.90-1.74 (m, 2H), 1.68-1.54 (m, 2H), 1.44-1.33 (m, 2H); MS (ES⁺) m/z 354 (M+H)⁺.

Step 8: methyl 5-bromo-6-(2-fluorocyclohexyl)-4-(2-methoxy-2-oxoethyl)-4H-thieno[3,2-b]pyrrole-2-carboxylate N-bromo succinimide (1.5 eq.) was added at 0° C. to a 0.1M solution of methyl 6-(2-fluorocyclohexyl)-4-(2-methoxy-2-oxoethyl)-4H-thieno[3,2-b]pyrrole-2-carboxylate in dry DCM, and the mixture was stirred for 1 h. After dilution with EtOAc, the organic layer was washed with aq. Na₂S₂O₃-solution and brine, dried over Na₂SO₄ and concentrated i. vac. Yield: 100%. ¹H-NMR (300 MHz, CDCl₃, 300 K, δ) 7.58 (s, 1H), 4.88 (d, 1H, J 17.9), 4.79 (d, 1H, J 17.9), 4.64 (dtd, 1H, J 49.3, 10.6, 4.4), 3.88 (s, 3H), 3.78 (s, 3H), 2.94-2.83 (m, 1H), 2.28-2.24 (m, 1H), 1.99-1.33 (m, 7H); MS (ES⁺) m/z 432, 434 (M+H)⁺.

Step 9: methyl 6-(2-fluorocyclohexyl)-5-(2-formylphenyl)-4-(2-methoxy-2-oxoethyl)-4H-thieno[3,2-b]pyrrole-2-carboxylate A solution (0.1 M) of methyl 5-bromo-6-(2-fluorocyclohexyl)-4-(2-methoxy-2-oxoethyl)-4H-thieno[3,2-b]pyrrole-2-carboxylate in dioxane was treated with (2-formylphenyl)boronic acid (1.5 eq.); aq. Na₂CO₃-solution (2 N, 8.5 eq.) was added and the solution was degassed, and then treated with Pd(PPh₃)₄ (0.1 eq.). A balloon with argon was installed, the mixture was placed in an oil bath preheated at 115° C. and stirred for 30 min, then cooled and diluted with EtOAc and brine. The organic phase was separated, washed with 1N HCl and brine, dried and concentrated. The residue was purified by chromatography (PE/EtOAc) to give the title compound (56%); some starting material (21%) was recovered. ¹H-NMR (400 MHz, CDCl₃, 300K, δ) 9.78&9.85* (bs, 1H.), 8.06 (dd, 1H, J 7.7, 1.3), 7.67 (s, 1H), 7.73-7.60 (m, 2H), 7.44 (bd, 1H, J 7.5), 4.50&4.55* (d, 1H, J 17.8&17.6), 4.44&4.48* (d, 1H, J 17.8&17.6), 4.73-4.49 (m, 1H), 3.91 (s, 3H), 3.62&3.63* (s, 3H), 2.42-2.34 (m, 1H), 2.18-2.12 (m, 1H), 1.83-1.07 (m, 7H); MS (ES⁺) m/z 458 (M+H)⁺. * Refers to two different conformers.

Step 10: 6-[2-(dimethylamino)ethyl]-13-(2-fluorocyclohexyl)-5,6,7,8-tetrahydrothieno[2',3':4,5]pyrrolo[2,1-a][2,5]benzodiazocine-11-carboxylic acid A solution (0.1 M) of methyl 6-(2-fluorocyclohexyl)-5-(2-formylphenyl)-4-(2-methoxy-2-oxoethyl)-4H-thieno[3,2-b]pyrrole-2-carboxylate and dimethylethylenediamine (1.5 eq.) in MeOH was stirred at RT for 3 h, then NaCNBH₃ (excess) was added and the mixture was stirred for 3 days; evaporation to dryness gave a residue that was taken into EtOAc and washed with sat. NaHCO₃-solution and brine, dried and concentrated i. vac. to obtain methyl 6-[2-(dimethylamino)ethyl]-13-[(1R,2S)-2-fluorocyclohexyl]-7-oxo-5,6,7,8-tetrahydrothieno[2',3':4,5]pyrrolo[2,1-a][2,5]benzodiazocine-11-carboxylate that was used without further purification. The latter was dissolved in dry THF (0.1M) and treated with 2M borane dimethylsulfide complex in THF (excess), and the mixture was stirred overnight at RT. 1.25M HCl in MeOH was added dropwise, the flask was opened and the mixture was stirred for 3 h at 85° C. Evaporation to dryness gave a residue that was hydrolised with 1M aq. KOH (3 eq.) in dioxane (85° C., 2 h); after quenching with 6M aq. HCl and removal of all volatiles the title compound was isolated by RP-HPLC. Yield: 60%. ¹H-NMR (400 MHz, DMSO-d₆, 300K, δ) 8.04 (d, 1H, J 2.2) 7.85-7.46 (m, 4H), 4.74-4.69 (m, 1H), 4.86-4.45 (m, 1H), 4.40 (bt, 1H, J 12.5), 3.74-3.42 (m, 8H), 2.88 (s, 3H), 2.87 (s, 3H), 2.74-2.61 (m, 1H), 2.26-1.03 (m, 8H); MS (ES⁺) m/z 470 (M+H)⁺.

EXAMPLE 15

Preparation of (7R)-13-cyclohexyl-7-(dimethylamino)-10-methyl-7,8-dihydro-6H-thieno[2',3':4,5]pyrrolo[1,2-e][1,5]benzoxazocine-11-carboxylic acid Step 1: methyl 5-bromo-6-cyclohexyl-4-(methoxymethyl)-4H-thieno[3,2-b]pyrrole-2-carboxylate Methyl 5-bromo-6-cyclohexyl-4H-thieno[3,2-b]pyrrole-2-carboxylate (prepared as in Example 7, Step 1) was dissolved in DMF and sodium hydride (1.4 eq.) was added. The mixture was stirred at RT until evolution of gas had ceased, then chloromethyl methyl ether (excess) was added and stirring was continued. After 5 h all volatiles were evaporated i. vac. and the residual material was filtered through silica gel (PE:Et$_2$O, 12:1). The product was obtained as a colourless solid (66%). $^1$H-NMR (400 MHz, CDCl$_3$, 300 K, δ): 7.73 (s, 1H), 5.41 (s, 2H), 3.90 (s, 3H), 3.32 (s, 3H), 2.73-2.67 (m, 1H), 1.90-1.76 (m, 5H), 1.65-1.58 (m, 2H), 1.47-1.29 (m, 3H).

Step 2: methyl 5-[2-(benzyloxy)phenyl]-6-cyclohexyl-3-formyl-4-(methoxymethyl)-4H-thieno[3,2-b]pyrrole-2-carboxylate Methyl 5-bromo-6-cyclohexyl-4-(methoxymethyl)-4H-thieno[3,2-b]pyrrole-2-carboxylate, 2-benzyloxyphenyl boronic acid (1.8 eq.) and Pd(PPh$_3$)$_2$Cl$_2$ (0.3 eq.) were dissolved in dioxane (0.09M). 2M Na$_2$CO$_3$-solution (8.5 eq.) was added and after degassing the mixture was heated for 5 h to 110° C. All volatiles were evaporated i. vac. and the residual material was subjected to chromatography (PE:EtOAc, 4:1). The product fractions were evaporated and the sticky solid obtained was dissolved in MeOH/THF (1:1, 0.15 M) and 1M KOH-solution (excess) was added. The mixture was left stirring for 3 days at 40° C. All volatiles were evaporated i. vac. and the residual material was dissolved in water. The solution was acidified with 1N aq. HCl. The resulting suspension was extracted DCM. The organic phase was washed with brine and dried over Na$_2$SO$_4$. All volatiles were evaporated and the remaining solid was dissolved in THF (0.2M). This solution was added slowly at −78° C. to a mixture of TMEDA (5 eq.) and 1.6M n-butyl lithium (5 eq.) in THF, followed by the addition of an excess of DMF. After stirring for 30 min at −78° C. an excess of sat. aq. NH$_4$Cl-solution was added and the mixture was left standing for 90 min at −78° C. Then the mixture was transferred into an excess of 0.2N aq. HCl. The mixture was extracted with DCM, the organic phase was washed with brine, dried over Na$_2$SO$_4$ and all volatiles were evaporated i. vac. The residual material was dissolved in DMF (0.5M) and an excess of K$_2$CO$_3$ was added, followed by an excess of methyl iodide. The mixture was left stirring over night, then all volatiles were evaporated. The residual material was purified by chromatography (PE:EtOAc, 8.5:1.5) to give a yellow solid (28%). MS (ES$^+$) m/z 518 (M+H)$^+$.

Step 3: methyl 6-cyclohexyl-5-(2-hydroxyphenyl)-4-(methoxymethyl)-3-methyl-4H-thieno[3,2-b]pyrrole-2-carboxylate Methyl 5-[2-(benzyloxy)phenyl]-6-cyclohexyl-3-formyl-4-(methoxymethyl)-4H-thieno[3,2-b]pyrrole-2-carboxylate was dissolved in EtOAc and the solution was degassed. Pd/C was added and after degassing again hydrogen atmosphere (60 psi) was applied. After hydrogenating for 2 days the catalyst was filtered off and all volatiles were evaporated i. vac. An off-white solid was obtained (89%). MS (ES$^+$) m/z 414 (M+H)$^+$.

Step 4: Methyl 5-{2-[((2R)-2-{[(benzyloxy)carbonyl]amino}-3-hydroxypropyl)oxy]phenyl}-6-cyclohexyl-3-methyl-4H-thieno[3,2-b]pyrrole-2-carboxylate Methyl 6-cyclohexyl-5-(2-hydroxyphenyl)-4-(methoxymethyl)-3-methyl-4H-thieno[3,2-b]pyrrole-2-carboxylate was dissolved in dioxane (0.036M) and the same volume of 6N HCl was added. The mixture was subjected to microwave irradiation (10 min @ 130° C.). All volatiles were evaporated and the product was enriched by prep. RP-HPLC. The product-containing fractions were lyophilised to give a green glassy solid. This material was dissolved in DMF (0.16M) and benzyl (4R)-2,2-dimethyl-4-({[(4-nitrophenyl)sulfonyl]oxy}methyl)-1,3-oxazolidine-3-carboxylate (excess, prepared according to *Synthesis* 1996, 189 in analogy to benzyl (4R)-2,2-dimethyl-4-({[(4-methylphenyl)sulfonyl]oxy}methyl)-1,3-oxazolidine-3-carboxylate from benzyl (4S)-4-(hydroxymethyl)-2,2-dimethyl-1,3-oxazolidine-3-carboxylate and substituting tosyl chloride with 4-nitrobenzenesulfonyl chloride) was added. The suspension was heated to 50° C. overnight. All volatiles were evaporated i. vac. and the residual material was purified by prep. RP-HPLC. The product fractions were evaporated and the residual material lyophilised from MeCN/water. A beige solid was obtained, which was dissolved dry MeOH (0.2M) and 1.25M HCl in MeOH (excess) was added. The solution was left stirring at RT. After 3 h all volatiles were evaporated and the residual material was subjected to purification by chromatography (PE:EtOAc, 6:4). After evaporation of the product fractions the product was obtained as a yellow powder (31%). MS (ES$^+$) m/z 577 (M+H)$^+$.

Step 5: methyl 5-{2-[((2S)-2-{[(benzyloxy)carbonyl]amino}-3-bromopropyl)oxy]phenyl}-6-cyclohexyl-3-methyl-4H-thieno[3,2-b]pyrrole-2-carboxylate Methyl 5-{2-[((2R)-2-{[(benzyloxy)carbonyl]amino}-3-hydroxypropyl)oxy]phenyl}-6-cyclohexyl-3-methyl-4H-thieno[3,2-b]pyrrole-2-carboxylate and triphenylphosphine (2.27 eq.) were dissolved in DCM (0.02M) and K$_2$CO$_3$ (4.31 eq.) was added. To the stirred mixture CBr$_4$ (2.22 eq.) was added and the yellowish reaction mixture was left stirring at RT for 3 h. All volatiles were evaporated i. vac. and the residual material was subjected to chromatography (PE:EtOAc, 8.5:1.5). The product was obtained as a yellowish sticky solid (86%). MS (ES$^+$) m/z 639, 641 (M+H)$^+$.

Step 6: Methyl (7R)-7-{[(benzyloxy)carbonyl]amino}-13-cyclohexyl-10-methyl-7,8-dihydro-6H-thieno[2',3':4,5]pyrrolo[1,2-e][1,5]benzoxazocine-11-carboxylate Methyl 5-{2-[((2S)-2-{[(benzyloxy)carbonyl]amino}-3-bromopropyl)oxy]phenyl}-6-cyclohexyl-3-methyl-4H-thieno[3,2-b]pyrrole-2-carboxylate was dissolved in DMF (0.034M) and NaH (1.1 eq., 60% in mineral oil) was added. The mixture was left stirring at RT. After 30 min all volatiles were evaporated i. vac. The residual material was purified by chromatography (PE:EtOAc, 8.5:1.5). The product was obtained as a colourless solid (45%). MS (ES$^+$) m/z 559 (M+H)$^+$.

Step 7: (7R)-13-cyclohexyl-7-(dimethylamino)-10-methyl-7,8-dihydro-6H-thieno[2',3':4,5]pyrrolo[1,2-e][1,5]benzoxazocine-11-carboxylic acid Methyl (7R)-7-{[(benzyloxy)carbonyl]amino}-13-cyclohexyl-10-methyl-7,8-dihydro-6H-thieno[2',3':4,5]pyrrolo[1,2-e][1,5]benzoxazocine-11-carboxylate was dissolved EtOAc/MeOH and the solution (0.014M) was degassed. Pd/C was added and hydrogen atmosphere was applied. The mixture was left stirring under hydrogen atmosphere for 4 h. The mixture was filtered and evaporated i. vac. The residual material was lyophilised from MeCN/water to give a colourless powder. This material was dissolved in DCM (0.05M) and the pH was adjusted with AcOH to 4. A solution of formaldehyde (16 eq.) in water was added and the mixture was left stirring for 10 min at RT. Then NaCNBH$_3$ (12 eq.) was added and stirring was continued for 6 h. The mixture was diluted with DCM and extracted with sat. aq. NaHCO$_3$-solution. The organic phase was dried over Na$_2$SO$_4$ and evaporated i. vac. This material was dissolved in MeOH and THF was added (0.02M). To the solution 1M aq. KOH solution (excess) was added and the resulting mixture was warmed to 40° C. overnight. The product was isolated by prep. RP-HPLC. After lyophilisation, the product was obtained as a colourless powder (68%). $^1$H-NMR (TFA-salt, 400 MHz, DMSO-d$_6$, 300K, δ): 12.77 (bs, 1H); 10.40 (bs, 1H), 7.46-7.42 (m, 1H), 7.23-7.09 (m, 3H), 5.03-5.00 (m, 1H), 4.44-4.41 (m, 1H), 4.10-4.03 (m, 1H), 3.82-3.58 (m, 2H), 2.97 (bs, 6H) 2.83 (s, 3H), 2.67-2.52 (m, 1H), 1.99-1.55 (m, 7H), 1.38-1.12 (m, 3H); MS (ES$^+$) m/z 439 (M+H)$^+$.

The following table contains further examples:

TABLE

| Example | Name | Synthesised according to Example | ES+ (m/z) |
|---|---|---|---|
| 16 | 2-(10-carboxy-12-cyclohexyl-6,7-dihydro-5H-thieno[2',3':4,5]pyrrolo[1,2-d][1,4]benzodiazepin-5-yl)-N-[2-(dimethylamino)ethyl]-N,N-dimethylethanaminium trifluoroacetate | 9 | 509 |
| 17 | 13-cyclohexyl-6-(2-morpholin-4-ylethyl)-5,6,7,8-tetrahydrothieno[2',3':4,5]pyrrolo[2,1-a][2,5]benzodiazocine-11-carboxylic acid | 2 | 494 |
| 18 | 6-(2-azetidin-1-ylethyl)-13-cyclohexyl-5,6,7,8-tetrahydrothieno[2',3':4,5]pyrrolo[2,1-a][2,5]benzodiazocine-11-carboxylic acid | 2 | 462 (ES−) |
| 19 | 13-cyclohexyl-6-[2-(3,3-difluoropyrrolidin-1-yl)ethyl]-5,6,7,8-tetrahydrothieno[2',3':4,5]pyrrolo[2,1-a][2,5]benzodiazocine-11-carboxylic acid | 2 | 514 |
| 20 | 13-cyclohexyl-6-{2-[(3R)-3-fluoropyrrolidin-1-yl]ethyl}-5,6,7,8-tetrahydrothieno[2',3':4,5]pyrrolo[2,1-a][2,5]benzodiazocine-11-carboxylic acid | 2 | 496 |
| 21 | 12-cyclohexyl-5-[2-(dimethylamino)ethyl]-4,5,6,7-tetrahydrothieno[2,3-f]thieno[2',3':4,5]pyrrolo[1,2-d][1,4]diazocine-10-carboxylic acid | 12 | 458 |
| 22 | 13-cyclohexyl-6-[2-(diethylamino)ethyl]-5,6,7,8-tetrahydrothieno[2',3':4,5]pyrrolo[2,1-a][2,5]benzodiazocine-11-carboxylic acid | 2 | 480 |
| 23 | 13-cyclohexyl-6-(2-piperazin-1-ylethyl)-5,6,7,8-tetrahydrothieno[2',3':4,5]pyrrolo[2,1-a][2,5]benzodiazocine-11-carboxylic acid | 2 | 493 |
| 24 | 13-cyclohexyl-6-[2-(4-methylpiperazin-1-yl)ethyl]-5,6,7,8-tetrahydrothieno[2',3':4,5]pyrrolo[2,1-a][2,5]benzodiazocine-11-carboxylic acid | 2 | 507 |
| 25 | 13-cyclohexyl-6-{2-[(2-hydroxyethyl)(methyl)amino]ethyl}-5,6,7,8-tetrahydrothieno[2',3':4,5]pyrrolo[2,1-a][2,5]benzodiazocine-11-carboxylic acid | 2 | 482 |
| 26 | 6-{2-[[2-(benzyloxy)ethyl](methyl)amino]ethyl}-13-cyclohexyl-5,6,7,8-tetrahydrothieno[2',3':4,5]pyrrolo[2,1-a][2,5]benzodiazocine-11-carboxylic acid | 2 | 572 |
| 27 | 13-cyclohexyl-6-[(1-methylpiperidin-2-yl)methyl]-5,6,7,8-tetrahydrothieno[2',3':4,5]pyrrolo[2,1-a][2,5]benzodiazocine-11-carboxylic acid | 2 | 492 |
| 28 | 13-cyclohexyl-6-(2-pyrrolidin-1-ylethyl)-5,6,7,8-tetrahydrothieno[2',3':4,5] pyrrolo[2,1-a][2,5]benzodiazocine-11-carboxylic acid | 2 | 478 |
| 29 | 13-cyclohexyl-6-(1-isopropylpyrrolidin-3-yl)-5,6,7,8-tetrahydrothieno[2',3':4,5]pyrrolo[2,1-a][2,5]benzodiazocine-11-carboxylic acid | 13 | 492 |
| 30 | 13-cyclohexyl-6-(N,N-dimethylglycyl)-3-fluoro-5,6,7,8-tetrahydrothieno[2',3':4,5]pyrrolo[2,1-a][2,5]benzodiazocine-11-carboxylic acid | 5 | 484 |
| 31 | 13-cyclohexyl-6-[2-(dimethylamino)ethyl]-3-fluoro-5,6,7,8-tetrahydrothieno[2',3':4,5]pyrrolo[2,1-a][2,5]benzodiazocine-11-carboxylic acid | 2 | 470 |
| 32 | 3-(benzyloxy)-13-cyclohexyl-6-(1-isopropylpyrrolidin-3-yl)-5,6,7,8-tetrahydrothieno[2',3':4,5]pyrrolo[2,1-a][2,5]benzodiazocine-11-carboxylic acid | 13 | 598 |
| 33 | 3-chloro-13-cyclohexyl-6-(1-isopropylpyrrolidin-3-yl)-5,6,7,8-tetrahydrothieno[2',3':4,5]pyrrolo[2,1-a][2,5]benzodiazocine-11-carboxylic acid | 13 | 526 |
| 34 | 3-chloro-13-cyclohexyl-6-[2-(diethylamino)ethyl]-5,6,7,8-tetrahydrothieno[2',3':4,5]pyrrolo[2,1-a][2,5]benzodiazocine-11-carboxylic acid | 2 | 514 |
| 35 | 13-cyclohexyl-6-[2-(diethylamino)ethyl]-3-(pyridin-3-ylmethoxy)-5,6,7,8-tetrahydrothieno[2',3':4,5]pyrrolo[2,1-a][2,5]benzodiazocine-11-carboxylic acid | 2 | 587 |
| 36 | 13-cyclohexyl-6-[(3R)-1-isopropylpyrrolidin-3-yl]-5,6,7,8-tetrahydrothieno[2',3':4,5]pyrrolo[2,1-a][2,5]benzodiazocine-11-carboxylic acid | 13 | 492 |
| 37 | 13-cyclohexyl-3-fluoro-6-[(3S)-1-isopropylpyrrolidin-3-yl]-5,6,7,8-tetrahydrothieno[2',3':4,5]pyrrolo[2,1-a][2,5]benzodiazocine-11-carboxylic acid | 13 | 510 |

TABLE-continued

| Example | Name | Synthesised according to Example | ES+ (m/z) |
|---|---|---|---|
| 38 | 13-cyclohexyl-3-fluoro-6-[(3R)-1-isopropylpyrrolidin-3-yl]-5,6,7,8-tetrahydrothieno[2',3':4,5]pyrrolo[2,1-a][2,5]benzodiazocine-11-carboxylic acid | 13 | 510 |
| 39 | 12-cyclohexyl-5-hydroxy-6,7-dihydro-5H-thieno[2',3':4,5]pyrrolo[2,1-a][2]benzazepine-10-carboxylic acid | 11 | 382 |
| 40 | 12-cyclohexyl-6,7-dihydro-5H-thieno[2',3':4,5]pyrrolo[2,1-a][2]benzazepine-10-carboxylic acid | 11, Step 4 (byproduct) | 366 |
| 41 | 11-cyclohexyl-8-methylthieno[2',3':4,5]pyrrolo[1,2-c][1,3]benzoxazine-9-carboxylic acid | 15, Step 4 (byproduct) | 368 |

The invention claimed is:

1. A compound of formula (I):

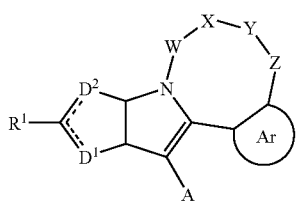

wherein

Ar is a moiety containing at least one aromatic ring and possesses 5, 6, 9 or 10 ring atoms optionally containing 1, 2 or 3 heteroatoms independently selected from the group consisting of N, O and S, which ring is optionally substituted by groups $Q^1$ and $Q^2$;

$Q^1$ is selected from the group consisting of halogen, hydroxy, $C_{1-6}$alkyl, $C_{1-6}$alkoxy, aryl, heteroaryl, CONR$^c$R$^d$, $(CH_2)_{0-3}$NR$^c$R$^d$, $O(CH_2)_{1-3}$NR$^c$R$^d$, $O(CH_2)_{0-3}$CONR$^c$R$^d$, $O(CH_2)_{0-3}$aryl, $O(CH_2)_{0-3}$heteroaryl, and OCHR$^e$R$^f$;

R$^c$ and R$^d$ are each independently selected from the group consisting of hydrogen, $C_{1-4}$ alkyl and C(O)$C_{1-4}$ alkyl, or R$^c$, R$^d$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

R$^e$ and R$^f$ are each independently selected from the group consisting of hydrogen and $C_{1-4}$alkoxy; or R$^e$ and R$^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$Q^2$ is selected from the group consisting of halogen, hydroxy, $C_{1-4}$alkyl and $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is selected from the group consisting of:
(i) $C_{3-6}$alkyl,
(ii) $C_{2-6}$alkenyl,
(iii) a non-aromatic ring of 3 to 8 ring atoms where said ring optionally contains a double bond and/or optionally contains a moiety selected from the group consisting of O, S, SO, $SO_2$ and NH, and
(iv) a non-aromatic bicyclic moiety of 4 to 8 ring atoms, and A is optionally substituted by halogen, hydroxy, $C_{1-4}$alkyl or $C_{1-4}$alkoxy;

one of $D^1$ and $D^2$ is S and the other is C—$(CH_2)_{0-3}R^2$;

$R^2$ is selected from the group consisting of hydrogen, $C_{1-6}$alkyl, hydroxy, $(CH_2)_{0-3}C_{1-6}$alkoxy, $(CH_2)_{0-3}$NR$^a$R$^b$, $(CH_2)_{0-3}$aryl and $(CH_2)_{0-3}$aryloxy, optionally substituted by hydroxy or halogen;

R$^a$ and R$^b$ are each independently selected from the group consisting of hydrogen, $C_{1-6}$alkyl, $C_{2-6}$alkenyl, $C_{2-6}$alkynyl and $C_{3-8}$cycloalkyl;

══════ represents a bond selected from the group consisting of a single and a double bond, wherein ══════ represents a single bond between CR$^1$ and S and ══════ represents a double bond between CR$^1$ and C—$(CH_2)_{0-3}R^2$;

$R^1$ is selected from the group consisting of hydrogen, halogen, $C_{1-4}$alkyl, $C_{1-4}$alkoxy, CN, $CO_2H$, $CO_2C_{1-4}$alkyl, aryl, heteroaryl and C(O)NR$^3$R$^4$, where said $C_{1-4}$alkyl, $C_{1-4}$alkoxy, aryl and heteroaryl groups are optionally substituted by hydroxy or fluorine;

$R^3$ is selected from the group consisting of hydrogen and $C_{1-4}$alkyl;

$R^4$ is selected from the group consisting of hydrogen, $C_{1-4}$alkyl, $C_{2-4}$alkenyl, $(CH_2)_{0-3}(CR^jR^k)_{0-1}R^5$ and $SO_2R^6$;

R$^j$ and R$^k$ are independently selected from the group consisting of halogen, $C_{1-6}$alkyl and $C_{1-6}$alkoxy, or R$^j$ and R$^k$, together with the carbon atom to which they are joined, form a 4- to 7-membered carbocycle or heterocycle containing 1 or 2 heteroatoms selected from the group consisting of N, O and S;

$R^5$ is selected from the group consisting of NR$^h$R$^i$, OR$^h$, C(O)NR$^q$R$^r$, aryl, heteroaryl and Het;

R$^h$ and R$^i$ are each independently selected from the group consisting of hydrogen and $C_{1-4}$alkyl;

R$^q$ and R$^r$ are each independently selected from the group consisting of hydrogen, $C_{1-6}$alkyl and aryl, optionally substituted by hydroxy, halogen, $C_{1-4}$alkyl, $C_{2-4}$alkenyl, $C_{2-4}$alkynyl, $(CH_2)_{0-3}CO_2H$, $(CH_2)_{0-3}CO_2(C_{1-6}$alkyl), (CH═CH)$CO_2H$ or (CH═CH)$CO_2(C_{1-6}$alkyl);

Het is a heteroaliphatic ring of 4 to 7 ring atoms, which ring may contain 1, 2 or 3 heteroatoms selected from the group consisting of N, O and S or a group selected from the group consisting of S(O), $S(O)_2$, NH and NC$_{1-4}$alkyl;

$R^6$ is selected from the group consisting of $C_{1-4}$alkyl, $C_{2-4}$alkenyl and $(CH_2)_{0-3}R^7$;

R$^7$ is selected from the group consisting of aryl, heteroaryl, C$_{1-4}$alkyl, C$_{3-8}$cycloalkyl, CO$_2$R$^8$, Het and NR$^m$R$^n$, wherein Het is as hereinbefore defined, R$^m$ and R$^n$ are each independently selected from the group consisting of hydrogen, C$_{1-4}$alkyl and CO$_2$(CH$_2$)$_{0-3}$aryl, and R$^8$ is selected from the group consisting of hydrogen and C$_{1-6}$alkyl, and wherein R$^7$ is optionally substituted by halogen, C$_{1-4}$alkyl or NR$^o$R$^p$, wherein R$^o$ and R$^p$ are each independently selected from the group consisting of hydrogen and C$_{1-4}$alkyl;

and where R$^4$ is optionally substituted by hydroxy, fluorine, chlorine, C$_{1-4}$alkyl, oxo, CO$_2$H or CO$_2$C$_{1-4}$alkyl;

or R$^3$, R$^4$ and the nitrogen atom to which they are attached form a heteroaliphatic ring of 4 to 7 ring atoms, where said ring is optionally substituted by halogen, hydroxy, oxo, C$_{1-4}$alkyl or C$_{1-4}$alkoxy;

W and Z are independently selected from the group consisting of a bond, CO=O, O, S, S(O), S(O)$_2$, —(CR$^{10}$R$^{11}$)—(CR$^{12}$R$^{13}$)$_{0-1}$— and NR$^{10}$;

X and Y are independently selected from the group consisting of a bond, C=O, O, —CR$^{14}$R$^{15}$— and NR$^{14}$;

and none, one or two of W, X, Y and Z are a bond;

R$^{10}$, R$^{11}$, R$^{12}$, R$^{13}$, R$^{14}$, and R$^{15}$ are each independently selected from the group consisting of hydrogen, hydroxy, C$_{1-6}$alkyl, C$_{2-6}$alkenyl, C$_{1-6}$alkoxy, C(O)C$_{1-6}$alkyl, (CH$_2$)$_{0-3}$Het, (CH$_2$)$_{0-3}$NR$^{16}$R$^{17}$, C(O)(CH$_2$)$_{0-3}$NR$^{16}$R$^{17}$, NHC(O)(CH$_2$)$_{0-3}$NR$^{16}$R$^{17}$, O(CH$_2$)$_{0-3}$NR$^{16}$R$^{17}$, S(O)$_{0-2}$(CH$_2$)$_{0-3}$R$^{16}$R$^{17}$ and C(O)(CH$_2$)$_{0-3}$OR$^{16}$, where Het is as hereinbefore defined optionally substituted by C$_{1-6}$alkyl;

R$^{16}$ and R$^{17}$ are independently selected from hydrogen, C$_{1-6}$alkyl, (CH$_2$)$_{0-4}$NR$^{18}$R$^{19}$ and (CH$_2$)$_{1-4}$OR$^{18}$, or R$^{16}$, R$^{17}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$alkyl, and which ring is optionally substituted by halogen, hydroxy, C$_{1-4}$alkyl or C$_{1-4}$alkoxy; and R$^{18}$ and R$^{19}$ are independently selected from the group consisting of hydrogen, C$_{1-6}$alkyl and (CH$_2$)$_{0-3}$phenyl, or R$^{18}$, R$^{19}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$alkyl, and which ring is optionally substituted by halogen, hydroxy, C$_{1-4}$alkyl or C$_{1-4}$alkoxy;

or a pharmaceutically acceptable salt thereof.

2. The compound as claimed in claim 1, wherein

R$^{10}$, R$^{11}$, R$^{12}$, R$^{13}$, R$^{14}$ and R$^{15}$ are each independently selected from the group consisting of hydrogen, hydroxy, C$_{1-6}$alkyl, C$_{2-6}$alkenyl, C$_{1-6}$alkoxy, C(O)C$_{1-6}$alkyl, Het, (CH$_2$)$_{0-3}$NR$^{16}$R$^{17}$, C(O)(CH$_2$)$_{0-3}$NR$^{16}$R$^{17}$, NHC(O)(CH$_2$)$_{0-3}$NR$^{16}$R$^{17}$, O(CH$_2$)$_{0-3}$NR$^{16}$R$^{17}$, S(O)$_{0-2}$(CH$_2$)$_{0-3}$R$^{16}$R$^{17}$ and C(O)(CH$_2$)$_{0-3}$OR$^{16}$;

R$^{16}$ and R$^{17}$ are independently selected from the group consisting of hydrogen, C$_{1-6}$alkyl and (CH$_2$)$_{0-4}$NR$^{18}$R$^{19}$, or R$^{16}$, R$^{17}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$alkyl, and which ring is optionally substituted by halogen, hydroxy, C$_{1-4}$alkyl or C$_{1-4}$alkoxy; and R$^{18}$ and R$^{19}$ are independently selected from the group consisting of hydrogen and C$_{1-6}$alkyl, or R$^{18}$, R$^{19}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$ alkyl, and which ring is optionally substituted by halogen, hydroxy, C$_{1-4}$alkyl or C$_{1-4}$alkoxy;

or a pharmaceutically acceptable salt thereof.

3. The compound as claimed in claim 1, wherein Ar is a 5- or 6-membered aromatic ring optionally containing 1, 2 or 3 heteroatoms independently selected from the group consisting of N, O and S.

4. The compound as claimed in claim 1, wherein A is selected from the group consisting of C$_{3-6}$alkyl, C$_{2-6}$alkenyl or C$_{3-8}$cycloalkyl, where A is optionally substituted by halogen, hydroxy, C$_{1-4}$alkyl or C$_{1-4}$alkoxy.

5. The compound as claimed in claim 1, wherein D$^1$ is S and D$^2$ is C—(CH$_2$)$_{0-3}$R$^2$.

6. The compound as claimed in claim 1, wherein R$^1$ is selected from the group consisting of CO$_2$H, heteroaryl and C(O)NR$^3$R$^4$ where said heteroaryl group is optionally substituted by hydroxy or fluorine.

7. The compound as claimed in claim 1, wherein W is selected from the group consisting of a bond, CO=O, —(CR$^{10}$R$^{11}$)—(CR$^{12}$R$^{13}$)$_{0-1}$— and NR$^{10}$.

8. The compound as claimed in claim 1, wherein Z is selected from the group consisting of a bond, C=O, O, —(CR$^{10}$R$^{11}$)—(CR$^{12}$R$^{13}$)$_{0-1}$— and NR$^{10}$.

9. The compound as claimed in claim 1, wherein X is selected from the group consisting of C=O, —CR$^{14}$R$^{15}$— and NR$^{14}$.

10. The compound as claimed in claim 1, wherein Y is selected from the group consisting of C=O, O, —CR$^{14}$R$^{15}$— and NR$^{14}$.

11. The compound as claimed in claim 1, wherein the compound of formula (I) is a compound of formula (Ia) or a pharmaceutically acceptable salt thereof:

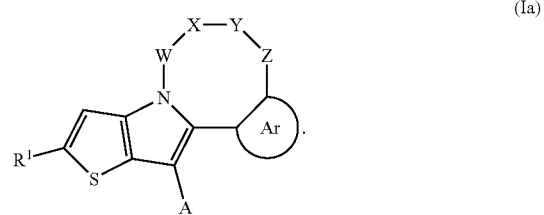

12. The compound as claimed in claim 1, wherein the compound of formula (I) is a compound selected from the group consisting of:

(i) compounds of formula (Iaa):

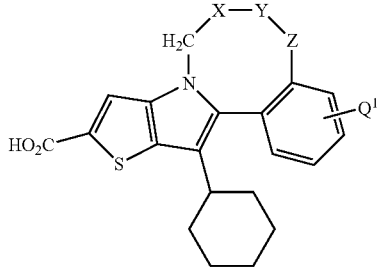

(Iaa)

or a pharmaceutically acceptable salt thereof;

(ii) compounds of formula (Ib):

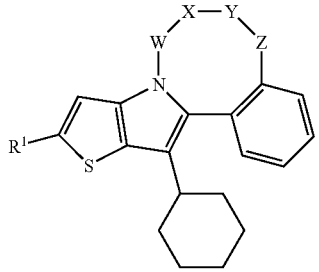

(Ib)

or a pharmaceutically acceptable salt thereof;

(iii) compounds of formula (Iab):

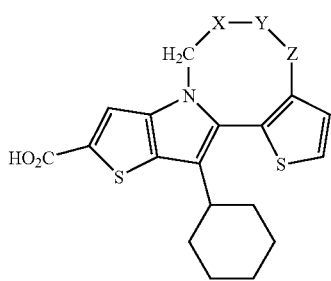

(Iab)

or a pharmaceutically acceptable salt thereof; and (iv) compounds of formula (Ic):

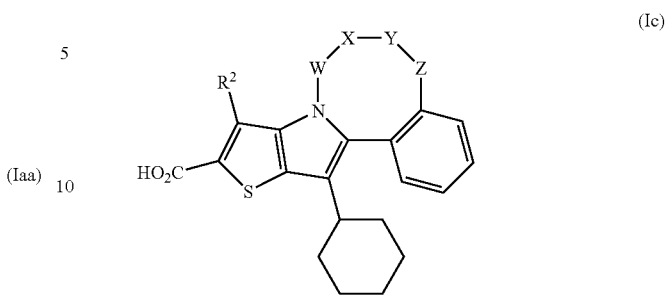

(Ic)

in which $R^2$ is $C_{1-4}$alkyl, or a pharmaceutically acceptable salt thereof.

13. A compound as claimed in claim 1, wherein the compound is selected from the group consisting of:

13-cyclohexyl-6-[2-(dimethylamino)ethyl]-7-oxo-5,6,7,8-tetrahydrothieno[2',3':4,5]pyrrolo[2,1-α][2,5]benzodiazocine-11-carboxylic acid;

13-cyclohexyl-6-[2-(dimethylamino)ethyl]-5,6,7,8-tetrahydrothieno[2',3':4,5]pyrrolo[2,1-α][2,5]benzodiazocine-11-carboxylic acid;

13-cyclohexyl-6-methyl-5,6,7,8-tetrahydrothieno[2',3':4,5]pyrrolo[2,1-α][2,5]benzodiazocine-11-carboxylic acid;

13-cyclohexyl-6-[2-(dimethylamino)ethyl]-3-methoxy-5,6,7,8-tetrahydrothieno[2',3':4,5]pyrrolo[2,1-α][2,5]benzodiazocine-11-carboxylic acid;

13-cyclohexyl-6-(N,N-dimethylglycyl)-5,6,7,8-tetrahydrothieno[2',3':4,5]pyrrolo[2,1-α][2,5]benzodiazocine-11-carboxylic acid;

13-cyclohexyl-7-{[2-(dimethylamino)ethyl]amino}-7,8-dihydro-6H-thieno[2',3':4,5]pyrrolo[1,2-e][1,5]benzoxazocine-11-carboxylic acid;

12-cyclohexyl-5-[2-(dimethylamino)ethyl]-6-oxo-6,7-dihydro-5H-thieno[2',3':4,5]pyrrolo[1,2-d][1,4]benzodiazepine-10-carboxylic acid;

12-cyclohexyl-6-oxo-6,7-dihydro-5H-thieno[2',3':4,5]pyrrolo[1,2-d][1,4]benzodiazepine-10-carboxylic acid;

12-cyclohexyl-5-[2-(dimethylamino)ethyl]-6,7-dihydro-5H-thieno[2',3':4,5]pyrrolo[1,2-d][1,4]benzodiazepine-10-carboxylic acid;

(2E)-3-(4-{[(1-{[(13-cyclohexyl-6-methyl-5,6,7,8-tetrahydrothieno[2',3':4,5]pyrrolo[2,1-α][2,5]benzodiazocin-11-yl)carbonyl]amino}cyclopentyl) carbonyl]amino}phenyl)acrylic acid;

12-cyclohexyl-5-(2-pyrrolidin-1-ylethoxy)-6,7-dihydro-5H-thieno[2',3':4,5]pyrrolo[2,1-α][2]benzazepine-10-carboxylic acid;

12-cyclohexyl-6-(2-pyrrolidin-1-ylethoxy)-6,7-dihydro-5H-thieno[2',3':4,5]pyrrolo[2,1-α][2]benzazepine-10-carboxylic acid;

12-cyclohexyl-5-[2-(diethylamino)ethyl]-4,5,6,7-tetrahydrothieno[2,3-f]thieno[2',3':4,5]pyrrolo[1,2-d][1,4]diazocine-10-carboxylic acid;

13-cyclohexyl-6-[(3S)-1-isopropylpyrrolidin-3-yl]-5,6,7,8-tetrahydrothieno[2',3':4,5]pyrrolo[2,1-α][2,5]benzodiazocine-11-carboxylic acid;

6-[2-(dimethylamino)ethyl]-13-(2-fluorocyclohexyl)-5,6,7,8-tetrahydrothieno[2',3':4,5]pyrrolo[2,1-α][2,5]benzodiazocine-11-carboxylic acid;

(7R)-13-cyclohexyl-7-(dimethylamino)-10-methyl-7,8-dihydro-6H-thieno[2',3':4,5]pyrrolo[1,2-e][1,5]benzoxazocine-11-carboxylic acid;

2-(10-carboxy-12-cyclohexyl-6,7-dihydro-5H-thieno[2',3':4,5]pyrrolo[1,2-d][1,4]benzodiazepin-5-yl)-N-[2-(dimethylamino) ethyl]-N,N-dimethylethanaminium trifluoroacetate;

13-cyclohexyl-6-(2-morpholin-4-ylethyl)-5,6,7,8-tetrahydrothieno[2',3':4,5]pyrrolo[2,1-α][2,5]benzodiazocine-11-carboxylic acid;

6-(2-azetidin-1-ylethyl)-13-cyclohexyl-5,6,7,8-tetrahydrothieno[2',3':4,5]pyrrolo[2,1-α][2,5]benzodiazocine-11-carboxylic acid;

13-cyclohexyl-6-[2-(3,3-difluoropyrrolidin-1-yl)ethyl]-5,6,7,8-tetrahydrothieno[2',3':4,5]pyrrolo[2,1-α][2,5]benzodiazocine-11-carboxylic acid;

13-cyclohexyl-6-{2-[(3R)-3-fluoropyrrolidin-1-yl]ethyl}-5,6,7,8-tetrahydrothieno[2',3':4,5]pyrrolo[2,1-α][2,5]benzodiazocine-11-carboxylic acid;

12-cyclohexyl-5-[2-(dimethylamino)ethyl]-4,5,6,7-tetrahydrothieno[2,3-f]thieno[2',3':4,5]pyrrolo[1,2-d][1,4]diazocine-10-carboxylic acid;

13-cyclohexyl-6-[2-(diethylamino)ethyl]-5,6,7,8-tetrahydrothieno[2',3':4,5]pyrrolo[2,1-α][2,5]benzodiazocine-11-carboxylic acid;

13-cyclohexyl-6-(2-piperazin-1-ylethyl)-5,6,7,8-tetrahydrothieno[2',3':4,5]pyrrolo[2,1-α][2,5]benzodiazocine-11-carboxylic acid;

13-cyclohexyl-6-[2-(4-methylpiperazin-1-yl)ethyl]-5,6,7,8-tetrahydrothieno[2',3':4,5]pyrrolo[2,1-α][2,5]benzodiazocine-11-carboxylic acid;

13-cyclohexyl-6-{2-[(2-hydroxyethyl)(methyl)amino]ethyl}-5,6,7,8-tetrahydrothieno[2',3':4,5]pyrrolo [2,1-α][2,5]benzodiazocine-11-carboxylic acid;

6-{2-[[2-(benzyloxy)ethyl](methyl)amino]ethyl}-13-cyclohexyl-5,6,7,8-tetrahydrothieno[2',3':4,5]pyrrolo[2,1-α][2,5]benzodiazocine-11-carboxylic acid;

13-cyclohexyl-6-[(1-methylpiperidin-2-yl)methyl]-5,6,7,8-tetrahydrothieno[2',3':4,5]pyrrolo[2,1-α][2,5]benzodiazocine-11-carboxylic acid;

13-cyclohexyl-6-(2-pyrrolidin-1-ylethyl)-5,6,7,8-tetrahydrothieno[2',3':4,5]pyrrolo[2,1-α][2,5]benzodiazocine-11-carboxylic acid;

13-cyclohexyl-6-(1-isopropylpyrrolidin-3-yl)-5,6,7,8-tetrahydrothieno[2',3':4,5]pyrrolo [2,1-α][2,5]benzodiazocine-11-carboxylic acid;

13-cyclohexyl-6-(N,N-dimethylglycyl)-3-fluoro-5,6,7,8-tetrahydrothieno[2',3':4,5]pyrrolo[2,1-α][2,5]benzodiazocine-11-carboxylic acid;

13-cyclohexyl-6-[2-(dimethylamino)ethyl]-3-fluoro-5,6,7,8-tetrahydrothieno[2',3':4,5]pyrrolo [2,1-α][2,5]benzodiazocine-11-carboxylic acid;

3-(benzyloxy)-13-cyclohexyl-6-(1-isopropylpyrrolidin-3-yl)-5,6,7,8-tetrahydrothieno[2',3':4,5]pyrrolo[2,1-α][2,5]benzodiazocine-11-carboxylic acid;

3-chloro-13-cyclohexyl-6-(1-isopropylpyrrolidin-3-yl)-5,6,7,8-tetrahydrothieno[2',3':4,5]pyrrolo[2,1-α][2,5]benzodiazocine-11-carboxylic acid;

3-chloro-13-cyclohexyl-6-[2-(diethylamino)ethyl]-5,6,7,8-tetrahydrothieno[2',3':4,5]pyrrolo[2,1-α][2,5]benzodiazocine-11-carboxylic acid;

13-cyclohexyl-6-[2-(diethylamino)ethyl]-3-(pyridin-3-ylmethoxy)-5,6,7,8-tetrahydrothieno[2',3':4,5]pyrrolo[2,1-α][2,5]benzodiazocine-11-carboxylic acid;

13-cyclohexyl-6-[(3R)-1-isopropylpyrrolidin-3-yl]-5,6,7,8-tetrahydrothieno[2',3':4,5]pyrrolo[2,1-α][2,5]benzodiazocine-11-carboxylic acid;

13-cyclohexyl-3-fluoro-6-[(3S)-1-isopropylpyrrolidin-3-yl]-5,6,7,8-tetrahydrothieno[2',3':4,5]pyrrolo[2,1-α][2,5]benzodiazocine-11-carboxylic acid;

13-cyclohexyl-3-fluoro-6-[(3R)-1-isopropylpyrrolidin-3-yl]-5,6,7,8-tetrahydrothieno[2',3':4,5]pyrrolo[2,1-α][2,5]benzodiazocine-11-carboxylic acid;

12-cyclohexyl-5-hydroxy-6,7-dihydro-5H-thieno[2',3':4,5]pyrrolo[2,1-α][2]benzazepine-10-carboxylic acid;

12-cyclohexyl-6,7-dihydro-5H-thieno[2',3':4,5]pyrrolo[2,1-α][2]benzazepine-10-carboxylic acid;

11-cyclohexyl-8-methylthieno[2',3':4,5]pyrrolo[1,2-c][1,3]benzoxazine-9-carboxylic acid; and pharmaceutically acceptable salts thereof.

14. A pharmaceutical composition comprising a compound of claim 1, or a pharmaceutically acceptable salt thereof, in association with a pharmaceutically acceptable carrier.

15. The pharmaceutical composition as claimed in claim 14, further comprising one or more other agents for the treatment of viral infections.

16. A method of inhibiting hepatitis C virus polymerase and/or of treating a hepatitis C viral infection, the method comprising administering to a human or animal subject suffering from the infection a therapeutically effective amount of a compound of formula (I):

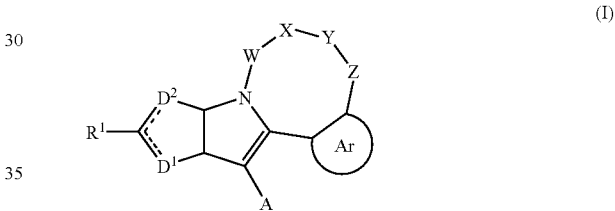

wherein

Ar is a moiety containing at least one aromatic ring and possesses 5, 6, 9 or 10 ring atoms optionally containing 1, 2 or 3 heteroatoms independently selected from the group consisting of N, O and S, which ring is optionally substituted by groups $Q^1$ and $Q^2$;

$Q^1$ is selected from the group consisting of halogen, hydroxy, $C_{1-6}$alkyl, $C_{1-6}$alkoxy, aryl, heteroaryl, CONR$^c$R$^d$, (CH$_2$)$_{0-3}$NR$^c$R$^d$, O(CH$_2$)$_{1-3}$NR$^c$R$^d$, O(CH$_2$)$_{0-3}$CONR$^c$R$^d$, O(CH$_2$)$_{0-3}$aryl, O(CH$_2$)$_{0-3}$heteroaryl, and OCHR$^e$R$^f$;

R$^c$ and R$^d$ are each independently selected from the group consisting of hydrogen, $C_{1-4}$ alkyl and C(O)$C_{1-4}$ alkyl, or R$^c$, R$^d$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

R$^e$ and R$^f$ are each independently selected from the group consisting of hydrogen and $C_{1-4}$alkoxy; or R$^e$ and R$^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$Q^2$ is selected from the group consisting of halogen, hydroxy, $C_{1-4}$alkyl and $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is selected from the group consisting of:
(i) $C_{3-6}$alkyl,
(ii) $C_{2-6}$alkenyl,
(iii) a non-aromatic ring of 3 to 8 ring atoms where said ring optionally contains a double bond and/or optionally contains a moiety selected from the group consisting of O, S, SO, $SO_2$ and NH, and
(iv) a non-aromatic bicyclic moiety of 4 to 8 ring atoms, and A is optionally substituted by halogen, hydroxy, $C_{1-4}$alkyl or $C_{1-4}$alkoxy;

one of $D^1$ and $D^2$ is S and the other is $C-(CH_2)_{0-3}R^2$;
$R^2$ is selected from the group consisting of hydrogen, $C_{1-6}$alkyl, hydroxy, $(CH_2)_{0-3}C_{1-6}$alkoxy, $(CH_2)_{0-3}NR^aR^b$, $(CH_2)_{0-3}$aryl and $(CH_2)_{0-3}$aryloxy, optionally substituted by hydroxy or halogen;
$R^a$ and $R^b$ are each independently selected from the group consisting of hydrogen, $C_{1-6}$alkyl, $C_{2-6}$alkenyl, $C_{2-6}$alkynyl and $C_{3-8}$cycloalkyl;
‾‾‾‾‾‾ represents a bond selected from the group consisting of a single and a double bond, wherein ‾‾‾‾‾‾ represents a single bond between $CR^1$ and S and ‾‾‾‾‾‾ represents a double bond between $CR^1$ and $C-(CH_2)_{0-3}R^2$;
$R^1$ is selected from the group consisting of hydrogen, halogen, $C_{1-4}$alkyl, $C_{1-4}$alkoxy, CN, $CO_2H$, $CO_2C_{1-4}$alkyl, aryl, heteroaryl and $C(O)NR^3R^4$, where said $C_{1-4}$alkly, alkoxy, aryl and heteroaryl groups are optionally substituted by hydroxy or fluorine;
$R^3$ is selected from the group consisting of hydrogen and $C_{1-4}$alkyl;
$R^4$ is selected from the group consisting of hydrogen, $C_{1-4}$alkyl, $C_{2-4}$alkenyl, $(CH_2)_{0-3}(CR^jR^k)_{0-1}R^5$ and $SO_2R^6$;
$R^j$ and $R^k$ are independently selected from the group consisting of halogen, $C_{1-6}$alkyl and $C_{1-6}$alkoxy, or $R^j$ and $R^k$, together with the carbon atom to which they are joined, form a 4- to 7-membered carbocycle or heterocycle containing 1 or 2 heteroatoms selected from the group consisting of N, O and S;
$R^5$ is selected from the group consisting of $NR^hR^i$, $OR^h$, $C(O)NR^qR^r$, aryl, heteroaryl and Het;
$R^h$ and $R^i$ are each independently selected from the group consisting of hydrogen and $C_{1-4}$alkyl;
$R^q$ and $R^r$ are each independently selected from the group consisting of hydrogen, $C_{1-6}$alkyl and aryl, optionally substituted by hydroxy, halogen, $C_{1-4}$alkyl, $C_{2-4}$alkenyl, $C_{2-4}$alkynyl, $(CH_2)_{0-3}CO_2H$, $(CH_2)_{0-3}CO_2(C_{1-6}$alkyl), $(CH=CH)CO_2H$ or $(CH=CH)CO_2(C_{1-6}$alkyl);
Het is a heteroaliphatic ring of 4 to 7 ring atoms, which ring may contain 1, 2 or 3 heteroatoms selected from the group consisting of N, O and S or a group selected from the group consisting of S(O), $S(O)_2$, NH and $NC_{1-4}$alkyl;
$R^6$ is selected from the group consisting of $C_{1-4}$alkyl, $C_{2-4}$alkenyl and $(CH_2)_{0-3}R^7$;
$R^7$ is selected from the group consisting of aryl, heteroaryl, $C_{1-4}$alkyl, $C_{3-8}$cycloalkyl, $CO_2R^8$, Het and $NR^mR^n$, wherein
Het is as hereinbefore defined,
$R^m$ and $R^n$ are each independently selected from the group consisting of hydrogen, $C_{1-4}$alkyl and $CO_2(CH_2)_{0-3}$aryl, and $R^8$ is selected from the group consisting of hydrogen and $C_{1-6}$alkyl,
and wherein $R^7$ is optionally substituted by halogen, $C_{1-4}$alkyl or $NR^oR^p$,
wherein $R^o$ and $R^p$ are each independently selected from the group consisting of hydrogen and $C_{1-4}$alkyl;
and where $R^4$ is optionally substituted by hydroxy, fluorine, chlorine, $C_{1-4}$alkyl, oxo, $CO_2H$ or $CO_2C_{1-4}$alkyl;
or $R^3$, $R^4$ and the nitrogen atom to which they are attached form a heteroaliphatic ring of 4 to 7 ring atoms, where said ring is optionally substituted by halogen, hydroxy, oxo, $C_{1-4}$alkyl or $C_{1-4}$alkoxy;
W and Z are independently selected from the group consisting of a bond, C=O, O, S, S(O), $S(O)_2$, $-(CR^{10}R^{11})-(CR^{12}R^{13})_{0-1}-$ and $NR^{10}$;
X and Y are independently selected from the group consisting of a bond, C=O, O, $-CR^{14}R^{15}-$ and $NR^{14}$;
and none, one or two of W, X, Y and Z are a bond;
$R^{10}$, $R^{11}$, $R^{12}$, $R^{13}$, $R^{14}$ and $R^{15}$ are each independently selected from the group consisting of hydrogen, hydroxy, $C_{1-6}$alkyl, $C_{2-6}$alkenyl, $C_{1-6}$alkoxy, $C(O)C_{1-6}$alkyl, $(CH_2)_{0-3}$Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{0-3}NR^{16}R^{17}$, $S(O)_{0-2}(CH_2)_{0-3}R^{16}R^{17}$ and $C(O)(CH_2)_{0-3}OR^{16}$, where Het is as hereinbefore defined optionally substituted by $C_{1-6}$alkyl;
$R^{16}$ and $R^{17}$ are independently selected from hydrogen, $C_{1-6}$alkyl, $(CH_2)_{0-4}NR^{18}R^{19}$ and $(CH_2)_{1-4}OR^{18}$, or $R^{16}$, $R^{17}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), $S(O)_2$, NH and $NC_{1-4}$alkyl, and which ring is optionally substituted by halogen, hydroxy, $C_{1-4}$alkyl or $C_{1-4}$alkoxy; and
$R^{18}$ and $R^{19}$ are independently selected from the group consisting of hydrogen, $C_{1-6}$alkyl and $(CH_2)_{0-3}$phenyl, or $R^{18}$, $R^{19}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), $S(O)_2$, NH and $NC_{1-4}$alkyl, and which ring is optionally substituted by halogen, hydroxy, $C_{1-4}$alkyl or $C_{1-4}$alkoxy;

or a pharmaceutically acceptable salt thereof.

17. A method of preparation of a pharmaceutical composition, comprising admixing at least one compound of formula (I) or a pharmaceutically acceptable salt thereof, with one or more pharmaceutically acceptable adjuvants, diluents or carriers, said compound of formula (I):

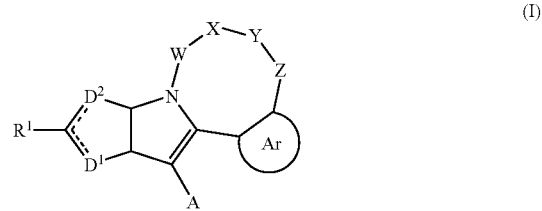

(I)

wherein
- Ar is a moiety containing at least one aromatic ring and possesses 5, 6, 9 or 10 ring atoms optionally containing 1, 2 or 3 heteroatoms independently selected from the group consisting of N, O and S, which ring is optionally substituted by groups $Q^1$ and $Q^2$;
- $Q^1$ is selected from the group consisting of halogen, hydroxy, $C_{1-6}$alkyl, $C_{1-6}$alkoxy, aryl, heteroaryl, $CONR^cR^d$, $(CH_2)_{0-3}NR^cR^d$, $O(CH_2)_{1-3}NR^cR^d$, $O(CH_2)_{0-3}CONR^cR^d$, $O(CH_2)_{0-3}$aryl, $O(CH_2)_{0-3}$heteroaryl, and $OCHR^eR^f$;
  - $R^c$ and $R^d$ are each independently selected from the group consisting of hydrogen, $C_{1-4}$ alkyl and $C(O)C_{1-4}$ alkyl, or $R^c$, $R^d$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;
  - $R^e$ and $R^f$ are each independently selected from the group consisting of hydrogen and $C_{1-4}$alkoxy; or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;
  - and wherein said $C_{1-4}$alkyl, $C_{1-4}$alkoxy and aryl groups are optionally substituted by halogen or hydroxy;
- $Q^2$ is selected from the group consisting of halogen, hydroxy, $C_{1-4}$alkyl and $C_{1-4}$alkoxy, where said $C_{1-4}$alkyl and $C_{1-4}$alkoxy groups are optionally substituted by halogen or hydroxy;
- or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;
- A is selected from the group consisting of:
  - (i) $C_{3-6}$alkyl,
  - (ii) $C_{2-6}$alkenyl,
  - (iii) a non-aromatic ring of 3 to 8 ring atoms where said ring optionally contains a double bond and/or optionally contains a moiety selected from the group consisting of O, S, SO, $SO_2$ and NH, and
  - (iv) a non-aromatic bicyclic moiety of 4 to 8 ring atoms, and A is optionally substituted by halogen, hydroxy, $C_{1-4}$alkyl or $C_{1-4}$alkoxy;
- one of $D^1$ and $D^2$ is S and the other is $C—(CH_2)_{0-3}R^2$;
  - $R^2$ is selected from the group consisting of hydrogen, $C_{1-6}$alkyl, hydroxy, $(CH_2)_{0-3}C_{1-6}$alkoxy, $(CH_2)_{0-3}NR^aR^b$, $(CH_2)_{0-3}$aryl and $(CH_2)_{0-3}$aryloxy, optionally substituted by hydroxy or halogen;
    - $R^a$ and $R^b$ are each independently selected from the group consisting of hydrogen, $C_{1-6}$alkyl, $C_{2-6}$alkenyl, $C_{2-6}$alkynyl and $C_{3-8}$cycloalkyl;
- ══════ represents a bond selected from the group consisting of a single and a double bond, wherein ══════ represents a single bond between $Cr^1$ and S and ══════ represents a double bond between $CR^1$ and $C—(CH_2)_{0-3}R^2$;
- $R^1$ is selected from the group consisting of hydrogen, halogen, $C_{1-4}$alkyl, $C_{1-4}$alkoxy, CN, $CO_2H$, $CO_2C_{1-4}$alkyl, aryl, heteroaryl and $C(O)NR^3R^4$, where said $C_{1-4}$alkyl, $C_{1-4}$alkoxy, aryl and heteroaryl groups are optionally substituted by hydroxy or fluorine;
- $R^3$ is selected from the group consisting of hydrogen and $C_{1-4}$alkyl;
- $R^4$ is selected from the group consisting of hydrogen, $C_{1-4}$alkyl, $C_{2-4}$ alkenyl, $(CH_2)_{0-3}(CR^jR^k)_{0-1}R^5$ and $SO_2R^6$;
  - $R^j$ and $R^k$ are independently selected from the group consisting of halogen, $C_{1-6}$alkyl and $C_{1-6}$alkoxy, or $R^j$ and $R^k$, together with the carbon atom to which they are joined, form a 4- to 7-membered carbocycle or heterocycle containing 1 or 2 heteroatoms selected from the group consisting of N, O and S;
  - $R^5$ is selected from the group consisting of $NR^hR^i$, $OR^h$, $C(O)NR^qR^r$, aryl, heteroaryl and Het;
    - $R^h$ and $R^i$ are each independently selected from the group consisting of hydrogen and $C_{1-4}$alkyl;
    - $R^q$ and $R^r$ are each independently selected from the group consisting of hydrogen, $C_{1-6}$alkyl and aryl, optionally substituted by hydroxy, halogen, $C_{1-4}$alkyl, $C_{2-4}$alkenyl, $C_{2-4}$alkynyl, $(CH_2)_{0-3}CO_2H$, $(CH_2)_{0-3}CO_2(C_{1-6}$alkyl), $(CH=CH)CO_2H$ or $(CH=CH)CO_2(C_{1-6}$alkyl);
    - Het is a heteroaliphatic ring of 4 to 7 ring atoms, which ring may contain 1, 2 or 3 heteroatoms selected from the group consisting of N, O and S or a group selected from the group consisting of S(O), $S(O)_2$, NH and $NC_{1-4}$alkyl;
  - $R^6$ is selected from the group consisting of $C_{1-4}$alkyl, $C_{2-4}$alkenyl and $(CH_2)_{0-3}R^7$;
    - $R^7$ is selected from the group consisting of aryl, heteroaryl, $C_{1-4}$alkyl, $C_{3-8}$cycloalkyl, $CO_2R^8$, Het and $NR'''R''$, wherein
      - Het is as hereinbefore defined,
      - $R'''$ and $R''$ are each independently selected from the group consisting of hydrogen, $C_{1-4}$alkyl and $CO_2(CH_2)_{0-3}$aryl, and
      - $R^8$ is selected from the group consisting of hydrogen and $C_{1-6}$alkyl,
      - and wherein $R^7$ is optionally substituted by halogen, $C_{1-4}$alkyl or $NR^oR^p$,
        - wherein $R^o$ and $R^p$ are each independently selected from the group consisting of hydrogen and $C_{1-4}$alkyl;
  - and where $R^4$ is optionally substituted by hydroxy, fluorine, chlorine, $C_{1-4}$alkyl, oxo, $CO_2H$ or $CO_2C_{1-4}$alkyl;
- or $R^3$, $R^4$ and the nitrogen atom to which they are attached form a heteroaliphatic ring of 4 to 7 ring atoms, where said ring is optionally substituted by halogen, hydroxy, oxo, $C_{1-4}$alkyl or $C_{1-4}$alkoxy;
- W and Z are independently selected from the group consisting of a bond, CO=O, O, S, S(O), $S(O)_2$, $—(CR^{10}R^{11})—(CR^{12}R^{13})_{0-3}—$ and $NR^{10}$;
- X and Y are independently selected from the group consisting of a bond, C=O, O, $—CR^{14}R^{15}—$ and $NR^{14}$;
- and none, one or two of W, X, Y and Z are a bond;
- $R^{10}$, $R^{11}$, $R^{12}$, $R^{13}$, $R^{14}$ and $R^{15}$ are each independently selected from the group consisting of hydrogen, hydroxy, $C_{1-6}$alkyl, $C_{2-6}$alkenyl, $C_{1-6}$alkoxy, $C(O)C_{1-6}$alkyl, $(CH_2)_{0-3}$Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{0-3}NR^{16}R^{17}$, $S(O)_{0-2}(CH_2)_{0-3}R^{16}R^{17}$ and $C(O)(CH_2)_{0-3}OR^{16}$, where Het is as hereinbefore defined optionally substituted by $C_{1-6}$alkyl;
- $R^{16}$ and $R^{17}$ are independently selected from hydrogen, $C_{1-6}$alkyl, $(CH_2)_{0-4}NR^{18}R^{19}$ and $(CH_2)_{1-4}OR^{18}$, or $R^{16}$, $R^{17}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), $S(O)_2$, NH and $NC_{1-4}$alkyl, and which ring is optionally substituted by halogen, hydroxy, $C_{1-4}$alkyl or $C_{1-4}$alkoxy; and $R^{18}$ and $R^{19}$ are independently selected from the group consisting of hydrogen, $C_{1-6}$alkyl and $(CH_2)_{0-3}$phenyl, or $R^{18}$, $R^{19}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$alkyl, and which ring is optionally substituted by halogen, hydroxy, $C_{1-4}$alkyl or $C_{1-4}$alkoxy;

or a pharmaceutically acceptable salt thereof.

18. A process for the preparation of a compound of formula (I):

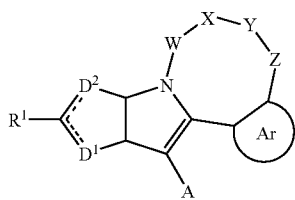

wherein
- Ar is a moiety containing at least one aromatic ring and possesses 5, 6, 9 or 10 ring atoms optionally containing 1, 2 or 3 heteroatoms independently selected from the group consisting of N, O and S, which ring is optionally substituted by groups $Q^1$ and $Q^2$;
- $Q^1$ is selected from the group consisting of halogen, hydroxy, $C_{1-6}$alkyl, $C_{1-6}$alkoxy, aryl, heteroaryl, CONR$^c$R$^d$, $(CH_2)_{0-3}$NR$^c$R$^d$, $O(CH_2)_{1-3}$NR$^c$R$^d$, $O(CH_2)_{0-3}$CONR$^c$R$^d$, $O(CH_2)_{0-3}$aryl, $O(CH_2)_{0-3}$heteroaryl, and OCHR$^e$R$^f$;
  - R$^c$ and R$^d$ are each independently selected from the group consisting of hydrogen, $C_{1-4}$ alkyl and C(O)$C_{1-4}$ alkyl, or R$^c$, R$^d$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;
  - R$^e$ and R$^f$ are each independently selected from the group consisting of hydrogen and $C_{1-4}$alkoxy; or R$^e$ and R$^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;
  - and wherein said $C_{1-4}$alkyl, $C_{1-4}$alkoxy and aryl groups are optionally substituted by halogen or hydroxy;
- $Q^2$ is selected from the group consisting of halogen, hydroxy, $C_{1-4}$alkyl and $C_{1-4}$alkoxy, where said $C_{1-4}$alkyl and $C_{1-4}$alkoxy groups are optionally substituted by halogen or hydroxy;
- or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;
- A is selected from the group consisting of:
  - (i) $C_{3-6}$alkyl,
  - (ii) $C_{2-6}$alkenyl,
  - (iii) a non-aromatic ring of 3 to 8 ring atoms where said ring optionally contains a double bond and/or optionally contains a moiety selected from the group consisting of O, S, SO, SO$_2$ and NH, and
  - (iv) a non-aromatic bicyclic moiety of 4 to 8 ring atoms, and A is optionally substituted by halogen, hydroxy, $C_{1-4}$alkyl or $C_{1-4}$alkoxy;
- one of $D^1$ and $D^2$ is S and the other is C—$(CH_2)_{0-3}R^2$;
- $R^2$ is selected from the group consisting of hydrogen, $C_{1-6}$alkyl, hydroxy, $(CH_2)_{0-3}C_{1-6}$alkoxy, $(CH_2)_{0-3}$NR$^a$R$^b$, $(CH_2)_{0-3}$aryl and $(CH_2)_{0-3}$aryloxy, optionally substituted by hydroxy or halogen;
  - R$^a$ and R$^b$ are each independently selected from the group consisting of hydrogen, $C_{1-6}$alkyl, $C_{2-6}$alkenyl, $C_{2-6}$alkynyl and $C_{3-8}$cycloalkyl;
- ====== represents a bond selected from the group consisting of a single and a double bond, wherein ====== represents a single bond between CR$^1$ and S and ====== represents a double bond between CR$^1$ and C—$(CH_2)_{0-3}R^2$;
- $R^1$ is selected from the group consisting of hydrogen, halogen, $C_{1-4}$alkyl, $C_{1-4}$alkoxy, CN, CO$_2$H, CO$_2C_{1-4}$alkyl, aryl, heteroaryl and C(O)NR$^3$R$^4$, where said $C_{1-4}$alkyl, $C_{1-4}$alkoxy, aryl and heteroaryl groups are optionally substituted by hydroxy or fluorine;
- $R^3$ is selected from the group consisting of hydrogen and $C_{1-4}$alkyl;
- $R^4$ is selected from the group consisting of hydrogen, $C_{1-4}$alkyl, $C_{2-4}$alkenyl, $(CH_2)_{0-3}(CR^jR^k)_{0-1}R^5$ and SO$_2R^6$;
  - R$^j$ and R$^k$ are independently selected from the group consisting of halogen, $C_{1-6}$alkyl and $C_{1-6}$alkoxy, or R$^j$ and R$^k$, together with the carbon atom to which they are joined, form a 4- to 7-membered carbocycle or heterocycle containing 1 or 2 heteroatoms selected from the group consisting of N, O and S;
  - $R^5$ is selected from the group consisting of NR$^h$R$^i$, OR$^h$, C(O)NR$^q$R$^r$, aryl, heteroaryl and Het;
    - R$^h$ and R$^i$ are each independently selected from the group consisting of hydrogen and $C_{1-4}$alkyl;
    - R$^q$ and R$^r$ are each independently selected from the group consisting of hydrogen, $C_{1-6}$alkyl and aryl, optionally substituted by hydroxy, halogen, $C_{1-4}$alkyl, $C_{2-4}$alkenyl, $C_{2-4}$alkynyl, $(CH_2)_{0-3}$CO$_2$H, $(CH_2)_{0-3}$CO$_2(C_{1-6}$alkyl), (CH=CH)CO$_2$H or (CH=CH)CO$_2(C_{1-6}$alkyl);
    - Het is a heteroaliphatic ring of 4 to 7 ring atoms, which ring may contain 1, 2 or 3 heteroatoms selected from the group consisting of N, O and S or a group selected from the group consisting of S(O), S(O)$_2$, NH and NC$_{1-4}$alkyl;
  - $R^6$ is selected from the group consisting of $C_{1-4}$alkyl, $C_{2-4}$alkenyl and $(CH_2)_{0-3}R^7$;
    - $R^7$ is selected from the group consisting of aryl, heteroaryl, $C_{1-4}$alkyl, $C_{3-8}$cycloalkyl, CO$_2R^8$, Het and NR$^m$R$^n$, wherein
      - Het is as hereinbefore defined,
      - R$^m$ and R$^n$ are each independently selected from the group consisting of hydrogen, $C_{1-4}$alkyl and CO$_2(CH_2)_{0-3}$aryl, and
      - $R^8$ is selected from the group consisting of hydrogen and $C_{1-6}$alkyl,
      - and wherein $R^7$ is optionally substituted by halogen, $C_{1-4}$alkyl or NR$^o$R$^p$,
        - wherein R$^o$ and R$^p$ are each independently selected from the group consisting of hydrogen and $C_{1-4}$alkyl;
  - and where $R^4$ is optionally substituted by hydroxy, fluorine, chlorine, $C_{1-4}$alkyl, oxo, CO$_2$H or CO$_2C_{1-4}$alkyl;
- or $R^3$, $R^4$ and the nitrogen atom to which they are attached form a heteroaliphatic ring of 4 to 7 ring atoms, where said ring is optionally substituted by halogen, hydroxy, oxo, $C_{1-4}$alkyl or $C_{1-4}$alkoxy;

W and Z are independently selected from the group consisting of a bond, C=O, O, S, S(O), S(O)$_2$, —(CR$^{10}$R$^{11}$)—(CR$^{12}$R$^{13}$)$_{0-1}$— and NR$^{10}$;

X and Y are independently selected from the group consisting of a bond, C=O, O, —CR$^{14}$R$^{15}$— and NR$^{14}$;

and none, one or two of W, X, Y and Z are a bond;

R$^{10}$, R$^{11}$, R$^{12}$, R$^{13}$, R$^{14}$ and R$^{15}$ are each independently selected from the group consisting of hydrogen, hydroxy, $C_{1-6}$alkyl, $C_{2-6}$alkenyl, $C_{1-6}$alkoxy, C(O)$C_{1-6}$alkyl, (CH$_2$)$_{0-3}$Het, (CH$_2$)$_{0-3}$NR$^{16}$R$^{17}$, C(O)(CH$_2$)$_{0-3}$NR$^{16}$R$^{17}$, NHC(O)(CH$_2$)$_{0-3}$NR$^{16}$R$^{17}$, O(CH$_2$)$_{0-3}$NR$^{16}$R$^{17}$, S(O)$_{0-2}$(CH$_2$)$_{0-3}$R$^{16}$R$^{17}$ and C(O)(CH$_2$)$_{0-3}$OR$^{16}$, where Het is as hereinbefore defined optionally substituted by $C_{1-6}$alkyl;

R$^{16}$ and R$^{17}$ are independently selected from hydrogen, $C_{1-6}$alkyl, (CH$_2$)$_{0-4}$NR$^{18}$R$^{19}$ and (CH$_2$)$_{1-4}$OR$^{18}$, or R$^{16}$, R$^{17}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$alkyl, and which ring is optionally substituted by halogen, hydroxy, $C_{1-4}$alkyl or $C_{1-4}$alkoxy; and R$^{18}$ and R$^{19}$ are independently selected from the group consisting of hydrogen, $C_{1-6}$alkyl and (CH$_2$)$_{0-3}$phenyl, or R$^{18}$, R$^{19}$ and the nitrogen atom to which they are attached form a heteroaliphatic ring of 4 to 7 ring atoms, which ring may optionally contain 1 or 2 more heteroatoms selected from the group consisting of O and S or a group selected from the group consisting of S(O), S(O)$_2$, NH and NC$_{1-4}$alkyl, and which ring is optionally substituted by halogen, hydroxy, $C_{1-4}$alkyl or $C_{1-4}$alkoxy;

or a pharmaceutically acceptable salt thereof;

said process comprising:

(a) where Z is CH$_2$, X is C=O and Y is NR$^{14}$, by the reaction of a compound of formula (II) with a compound of formula (III) followed by internal ring closure:

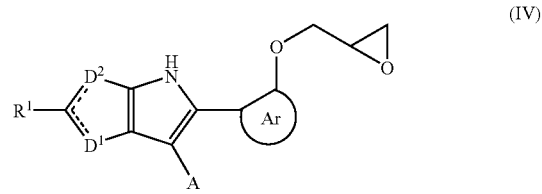

(II)

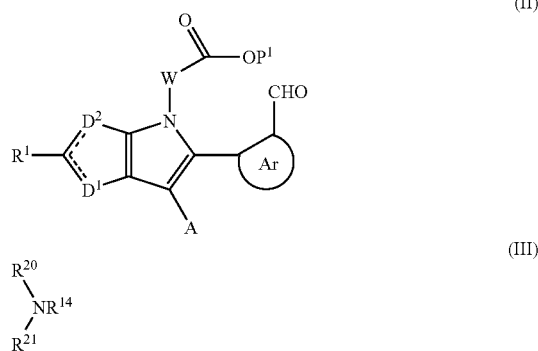

(III)

where D$^1$, D$^2$, W, A, Ar, R$^1$ and R$^{14}$ are as defined above with respect to formula (I), R$^{20}$ and R$^{21}$ are independently selected from the group consisting of hydrogen, methyl and ethyl, and P$^1$ is a suitable protecting group;

(b) where Z is O, W and Y are CH$_2$ and X is C=O, by the internal ring closure of a compound of formula (IV) followed by oxidation:

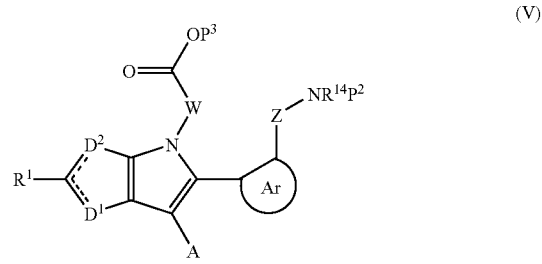

(IV)

where D$^1$, D$^2$, A, Ar, R$^1$ and R$^{14}$ are as defined above with respect to formula (I);

(c) where X is C=O and Y is NR$^{14}$, by internal ring closure of a compound of formula (V):

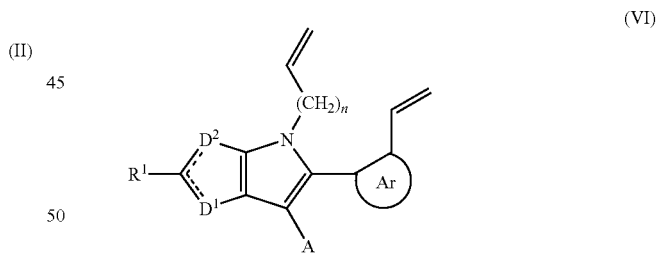

(V)

where W, Z, D$^1$, D$^2$, A, Ar, R$^1$ and R$^{14}$ are as defined above with respect to formula (I), and P$^2$ and P$^3$ are suitable protecting groups;

(d) where Z is CHR$^{10}$, Y is CHR$^{14}$, X is CH$_2$ and W is —(CH$_2$)$_{(n-1)}$—, by ring-closure metathesis of a compound of formula (VI) followed by elaboration of the newly formed double bond:

(VI)

where n is 1 to 3 and D$^1$, D$^2$, A, Ar, R$^1$, R$^{10}$ and R$^{14}$ are defined as above with respect to formula (I).

19. The pharmaceutical composition as claimed in claim 15, wherein said other agents are selected from the group consisting of antiviral agents and immunomodulatory agents.

* * * * *